US012723265B2

United States Patent
Hudecek et al.

(10) Patent No.: US 12,723,265 B2
(45) Date of Patent: Sep. 1, 2026

(54) METHOD FOR HIGH LEVEL AND STABLE GENE TRANSFER IN LYMPHOCYTES

(71) Applicant: Julius-Maximilians-Universität Würzburg, Würzburg (DE)

(72) Inventors: Michael Hudecek, Höchberg (DE); Zoltan Ivics, Berlin (DE)

(73) Assignee: Julius-Maximilians-Universität Würzburg, Würzburg (DE)

(*) Notice: Subject to any disclaimer, the term of this patent is extended or adjusted under 35 U.S.C. 154(b) by 0 days.

(21) Appl. No.: 15/761,783

(22) PCT Filed: Sep. 22, 2016

(86) PCT No.: PCT/EP2016/072524

§ 371 (c)(1),
(2) Date: Mar. 20, 2018

(87) PCT Pub. No.: WO2017/050884

PCT Pub. Date: Mar. 30, 2017

(65) Prior Publication Data

US 2019/0169637 A1 Jun. 6, 2019

(30) Foreign Application Priority Data

Sep. 22, 2015 (EP) .................................... 15002732
Jan. 29, 2016 (EP) .................................... 16153490

(51) Int. Cl.

| | |
|---|---|
| ***C12N 15/00*** | (2006.01) |
| ***A61K 40/11*** | (2025.01) |
| ***A61K 40/31*** | (2025.01) |
| ***A61K 40/42*** | (2025.01) |
| ***A61K 48/00*** | (2006.01) |
| ***C07K 14/705*** | (2006.01) |
| ***C07K 14/71*** | (2006.01) |
| ***C07K 16/28*** | (2006.01) |
| ***C12N 5/0783*** | (2010.01) |
| ***C12N 7/00*** | (2006.01) |
| ***C12N 9/12*** | (2006.01) |
| ***C12N 15/90*** | (2006.01) |

(52) U.S. Cl.

CPC .............. *C12N 15/90* (2013.01); *A61K 40/11* (2025.01); *A61K 40/31* (2025.01); *A61K 40/4204* (2025.01); *A61K 40/4211* (2025.01); *A61K 48/005* (2013.01); *C07K 14/70503* (2013.01); *C07K 14/7051* (2013.01); *C07K 14/70578* (2013.01); *C07K 14/71* (2013.01); *C07K 16/2803* (2013.01); *C12N 5/0636* (2013.01); *C12N 7/00* (2013.01); *C12N 9/1241* (2013.01); *C12Y 207/07* (2013.01); *A61K 2239/31* (2023.05); *A61K 2239/38* (2023.05); *A61K 2239/48* (2023.05); *C07K 2317/622* (2013.01); *C07K 2319/02* (2013.01); *C07K 2319/30* (2013.01); *C12N 2740/15043* (2013.01); *C12N 2800/50* (2013.01); *C12N 2800/90* (2013.01)

(58) Field of Classification Search

CPC .... C12N 5/0636; C12N 9/1241; C12N 15/00; C12N 15/09; C12N 15/87; C12N 15/90; C12N 15/907; C12N 2310/00; C12N 2800/90

See application file for complete search history.

(56) References Cited

U.S. PATENT DOCUMENTS

2005/0066376 A1* 3/2005 Craig ....................... C12N 9/22 435/455
2009/0131272 A1* 5/2009 Parinov ............. C12N 15/8509 536/23.6
2011/0047635 A1* 2/2011 Moisyadi ........... A01K 67/0275 800/25

(Continued)

FOREIGN PATENT DOCUMENTS

DE 102011118018 4/2013
WO WO 2004/009792 1/2004

(Continued)

OTHER PUBLICATIONS

Till et al, Blood 119(17): 3940-3950, 2012.*

(Continued)

*Primary Examiner* — Kevin K Hill
(74) *Attorney, Agent, or Firm* — James S. Keddie; Bozicevic, Field & Francis LLP

(57) ABSTRACT

The method disclosed herein describes a novel technology offering unparalleled efficiency, flexibility, utility and speed for the stable integration of transgenes into lymphocytes and other mammalian cells. The novel method is based on the use of an mRNA-encoded transposase (e.g. sleeping beauty transposase) in combination with a minicircle DNA-encoded transposable element. The novel method enables higher gene-transfer rates and is at the same time less toxic than the conventional approach, which is the use of plasmid DNA-encoded transposase in combination with a plasmid DNA-encoded transposable element. Applications of the invention include but are not limited to the stable integration of a transgene encoding an immune receptor (e.g. a T-cell receptor or synthetic chimeric antigen receptor) into human T lymphocytes, with the immune receptor conferring specificity for a molecule expressed by a tumor cell. The transposase mRNA and transposon minicircle DNA may be introduced into lymphocytes by methods including but not limited to electrotransfer such as electroporation and nucleofection.

7 Claims, 57 Drawing Sheets

Specification includes a Sequence Listing.

(56) References Cited

U.S. PATENT DOCUMENTS

2017/0029774 A1* 2/2017 Jensen .................. A61K 35/17

FOREIGN PATENT DOCUMENTS

WO WO 2008/027384 3/2008
WO WO 2014/153114 9/2014
WO WO 2014/160030 A2 10/2014
WO WO 2015/077607 A1 5/2015
WO WO 2015/077615 A1 5/2015
WO WO 15/157386 * 10/2015
WO WO 2015/157386 10/2015

OTHER PUBLICATIONS

Jensen et al, Biol. Blood Marrow Transplant 16: 1245-1256, 2010.*
Chen et al, Human Gene Therapy 16: 126-131, 2005.*
Chen, Efficient Gene Editing in Primary Human T cells, Trends Immunol. 36(11): 667-669, available online Oct. 1, 2015.*
Tumaini et al, Simplified process for the production of anti-CD19-CAR-engineered T cells, Cytotherapy 15: 1406-1415, available online Aug. 28, 2013.*
Kloss et al, Combinatorial antigen recognition with balanced signaling promotes selective tumor eradication by engineered T cells, Nature Biotechnol. 31(1): 71-75, available online Dec. 16, 2012.*
Almasbak et al, Inclusion of an lgG1-Fc spacer abrogates efficacy of CD19 CAR T cells in a xenograft mouse model, Gene Therapy 22: 391-403, available online Feb. 5, 2015.*
Singh et al, Nature of Tumor Control by Permanently and Transiently Modified GD2 Chimeric Antigen Receptor T Cells in Xenograft Models of Neuroblastoma, Cancer Immunol. Res. 2(11): 1059-1070, Nov. 2, 2014.*
Espe, Malacards: The Human Disease Database, J Med Libr Assoc. Jan. 2018; 106(1): 140-141, published online Jan. 2, 2018; doi: 10.5195/jmla.2018.253.*
Ruscetti et al, Functional and Morphologic Characterization of Human T Cells Continuously Grown in Vitro, J. Immunol. 119(1): 1331-138, 1977.*
Davila et al., "Efficacy and Toxicity Management of 19-28z CAR T Cell Therapy in B Cell Acute Lymphoblastic Leukemia", Sci Transl Med., 2014, 6(224): 224ra25. doi:10.1126/scitranslmed.3008226.
Maude et al., "Chimeric Antigen Receptor T Cells for Sustained Remissions in Leukemia", The New England Journal of Medicine, 2014, 371:1507-1517.
Kochenderfer et al., "Chemotherapy-Refractory Diffuse Large B-Cell Lymphoma and Indolent B-Cell Malignancies Can Be Effectively Treated With Autologous T Cells Expressing an Anti-CD19 Chimeric Antigen Receptor", Journal of Clinical Oncology, 2015, 33(6):540-549.
Izsvák et al., "Translating Sleeping Beauty transposition into cellular therapies: Victories and challenges", Bioessays., 2010, 32(9): 756-767, doi:10.1002/bies.201000027.
Ivics et al., "Nonviral Gene Delivery with the Sleeping Beauty Transposon System", Human Gene Therapy, 2011, 22:1043-1051.
Aronovich et al., "The Sleeping Beauty transposon system: a non-viral vector for gene therapy", Human Molecular Genetics, 2011, 20(1): R14-R20, doi:10.1093/hmg/ddr140.
Swierczek et al., "The Sleeping Beauty transposon system for clinical applications", Expert Opin. Biol. Ther., 2012, 12(2):139-153.
Ivics et al., "Molecular Reconstruction of Sleeping Beauty, a Tc1-like Transposon from Fish, and Its Transposition in Human Cells", Cell, 1997, 91:501-510.
Mátés et al., "Molecular evolution of a novel hyperactive Sleeping Beauty transposase enables robust stable gene transfer in vertebrates", Nature Genetics, 2009, 41(6): 753-761.
Peng et al., "Efficient nonviral Sleeping Beauty transposon-based TCR gene transfer to peripheral blood lymphocytes confers antigenspecific antitumor reactivity", Gene Ther., 2009, 16(8): 1042-1049. doi:10.1038/gt.2009.54.
Huang et al., "Sleeping Beauty Transposon-mediated Engineering of Human Primary T Cells for Therapy of CD19+ Lymphoid Malignancies", Mol Ther., 2008, 16(3): 580-589. doi:10.1038/sj.mt.6300404.
Jin et al., "The hyperactive Sleeping Beauty transposase SB100X improves the genetic modification of T cells to express a chimeric antigen receptor", Gene Ther., 2011, 18(9): 849-856. doi:10.1038/gt.2011.40.
Singh et al., "Redirecting Specificity of T-Cell Populations for CD19 Using the Sleeping Beauty System", Cancer Res., 2008, 68(8): 2961-2971.
Singh et al., "A new approach to gene therapy using Sleeping Beauty to genetically modify clinical-grade T cells to target CD19", Immunological Reviews, 2014, 257: 181-190.
Singh et al., "Manufacture of Clinical-Grade CD19-Specific T Cells Stably Expressing Chimeric Antigen Receptor Using Sleeping Beauty System and Artificial Antigen Presenting Cells", PLOS ONE, 2013, 8(5):e64138.
June et al., "Adoptive cellular therapy: A race to the f nish line", Sci Transl Med., 2015, 7(280):280ps7.
Ramos et al., "CD19-CAR Trials", Cancer J., 2014, 20(2): 112-118. doi:10.1097/PPO.0000000000000031.
Mayrhofer et al., "Use of Minicircle Plasmids for Gene Therapy", Methods in Molecular Biology, Gene Therapy of Cancer, 2009, 542:87-104, doi: 10.1007/978-1-59745-561-9_4.
Chen et al., "Minicircle DNA Vectors Devoid of Bacterial DNA Result in Persistent and High-Level Transgene Expression in Vivo", Molecular Therapy, 2003, 8(3):495-500.
Kay et al., "A Simple and Rapid Minicircle DNA Vector Manufacturing System", Nat Biotechnol., 2010, 28(12): 1287-1289. doi:10.1038/nbt.1708.
Kay et al., "A robust system for production of minicircle DNANA vectors", Nature Biotechnology, 2010, 28 (12):1287-1289.
Mayrhofer et al., "Minicircle-DNA production by site specific recombination and protein-DNA interaction chromatography", J Gene Med, 2008, 10: 1253-1269.
Chabot et al., "Minicircle DNA electrotransfer for efficient tissue-targeted gene delivery", Gene Therapy, 2013, 20:62-68.
Kobelt et al., "Performance of High Quality Minicircle DNA for In Vitro and In Vivo Gene Transfer", Mol Biotechnol, 2013, 53:80-89.
Sharma et al., "Efficient Sleeping Beauty DNA Transposition From DNA Minicircles", Molecular Therapy—Nucleic Acids, 2013, 2:e74, doi:10.1038/mtna.2013.1.
Cui et al., "Structure-Function Analysis of the Inverted Terminal Repeats of the Sleeping Beauty Transposon", J. Mol. Biol., 2002, 318: 1221-1235.
Hudecek et al., "The non-signaling extracellular spacer domain of chimeric antigen receptors is decisive for in vivo antitumor activity", Cancer Immunol Res., 2015, 3(2): 125-135, doi:10.1158/2326-6066.CIR-14-0127.
Wang et al., "Atransgene-encoded cell surface polypeptide for selection, in vivo tracking, and ablation of engineered cells", Blood, 2011, 118(5):1255-1263.
Hudecek et al., "Receptor affinity and extracellular domain modifications affect tumor recognition by ROR1-specific chimeric antigen receptor Tcells", Clin Cancer Res., 2013, 19(12): 3153-3164, doi:10.1158/1078-0432.CCR-13-0330.
Hudecek et al., "The B-cell tumor-associated antigen ROR1 can be targeted with T cells modified to express a ROR1-specific chimeric antigen receptor", Blood, 2010, 116(22):4532-4541.
Brown et al., "Biophotonic cytotoxicity assay for high-throughput screening of cytolytic killing", Journal of Immunological Methods, 2005, 297:39-52.
Sommermeyer et al., "Chimeric antigen receptor-modified T cells derived from defined CD8+ and CD4+ subsets confer superior antitumor reactivity in vivo", Leukemia., 2016, 30(2): 492-500, doi:10.1038/leu.2015.247.
Frigault et al., "Identification of chimeric antigen receptors that mediate constitutive or inducible proliferation of T cells", Cancer Immunol Res., 2015, 3(4): 356-367, doi:10.1158/2326-6066.CIR-14-0186.

(56) References Cited

OTHER PUBLICATIONS

Zayed et al., "Development of Hyperactive Sleeping Beauty Transposon Vectors by Mutational Analysis", Molecular Therapy, 2004, 9(2): 292-304.
Wang et al., "Analysis of Lentiviral Vector Integration in HIV+ Study Subjects Receiving Autologous Infusions of Gene Modified CD4+ T Cells", Mol Ther., 2009, 17(5): 844-850.
Vigdal et al, "Common Physical Properties of DNA Affecting Target Site Selection of Sleeping Beauty and other Tc1/mariner Transposable Elements", J. Mol. Biol., 2002, 323: 441-452.
Schones et al., "Dynamic Regulation of Nucleosome Positioning in the Human Genome", Cell, 2008, 132: 887-898.
Papapetrou et al., "Genomic safe harbors permit high β-globin transgene expression in thalassemia induced pluripotent stem cells", Nat Biotechnol., 2011, 29(1): 73-78, doi:10.1038/nbt.1717.
Sadelain et al., "Safe harbours for the integration of new DNA in the human genome", Nature Reviews Cancer, 2012, 12: 51-58.
Izsvák et al., "Sleeping Beauty, a Wide Host-range Transposon Vector for Genetic Transformation in Vertebrates", J Mol Biol., 2000, 302: 93-102.
Lukacs et al., "Size-dependent DNA Mobility in Cytoplasm and Nucleus", The Journal of Biological Chemistry, 2000, 275(3): 1625-1629.
Wilber et al., "RNA as a Source of Transposase for Sleeping Beauty-Mediated Gene Insertion and Expression in Somatic Cells and Tissues", Molecular Therapy, 2006, 13(3):625-630.
Hacein-Bey-Abina et al., "LMO2-Associated Clonal T Cell Proliferation in Two Patients after Gene Therapy for SCID-X1", Science, 2003, 302:415-419.
Yant et al., "High-Resolution Genome-Wide Mapping of Transposon Integration in Mammals", Molecular and Cellular Biology, 2005, 25(6): 2085-2094.
Jong et al., "Chromatin Landscapes of Retroviral and Transposon Integration Profiles", PLOS Genetics, 2014, 10(4): e1004250.
Grabundzija et al., "Comparative Analysis of Transposable Element Vector Systems in Human Cells", Molecular Therapy, 2010, 18(6):1200-1209, doi: 10.1038/mt.2010.47.
Huang et al., "Gene Transfer Efficiency and Genome-Wide Integration Profiling of Sleeping Beauty, Tol2, and PiggyBac Transposons in Human Primary T Cells", Molecular Therapy, 2010, 18(10): 1803-1813.
Maldarelli et al., "Specific HIV integration sites are linked to clonal expansion and persistence of infected cells", Science, 2014, 345(6193):179-183.
Voigt et al., "Retargeting Sleeping Beauty Transposon Insertions by Engineered Zinc Finger DNA-binding Domains", Molecular Therapy, 2012, 20(10):1852-1862.
Ivics et al., "Targeted Sleeping Beauty Transposition in Human Cells", Molecular Therapy, 2007, 15(6): 1137-1144.
Morgan et al., "ShortRead: a bioconductor package for input, quality assessment and exploration of high-throughput sequence data", Bioinformatics, 2009, 25(19): 2607-2608.
Lengmead et al., "Ultrafast and memory-efficient alignment of short DNA sequences to the human genome", Genome Biology, 2009, 10:R25.
Quinlan et al., "BEDTools: a flexible suite of utilities for comparing genomic features", Bioinformatics, 2010, 26(6): 841-842.
Barski et al., "High-Resolution Profiling of Histone Methylations in the Human Genome", Cell, 2007, 129: 823-837.
Zhang et al., "Model-based Analysis of ChIP-Seq (MACS)", Genome Biology, 2008, 9:R137.
Bejerano et al., "Ultraconserved Elements in the Human Genome", Science, 2004, 304: 1321-1325.
Monjezi et al., "Enhanced CAR T-cell engineering using non-viral Sleeping Beauty transposition from minicircle vectors", Leukemia, 2017, 31: 186-194.
Grupp et al., "Chimeric Antigen Receptor-Modified T Cells for Acute Lymphoid Leukemia", The New England Journal of Medicine, 2013, DOI: 10.1056/NEJMoa1215134, 10 pages.
Ivics et al., "Transposon-mediated genome manipulation in vertebrates", Nature Methods, 2009, 6(6): 415-422.
Ivics et al., "The expanding universe of transposon technologies for gene and cell engineering", Mobile DNA, 2010, 1:25, 15 pages.
Jia et al., "A nonviral minicircle vector for deriving human iPS cells", Nature Methods, 2010, 7(3): 197-199.
Kalos et al., "T Cells with Chimeric Antigen Receptors Have Potent Antitumor Effects and Can Establish Memory in Patients with Advanced Leukemia", Sci Transl Med, 2011, 3, 95ra73, DOI: 10.1126/scitranslmed.3002842.
Lander et al., "Initial sequencing and analysis of the human genome", Nature, 2001, 409: 860-921.
Ni et al., "Transposon tools hopping in vertebrates", Briefings in Functional Genomics and Proteomics, 2008, 7(6): 444-453.
Shapiro, "Molecular model for the transposition and replication of bacteriophage Mu and other transposable elements", Proc. Natl. Acad. Sci. USA, 1979, 76(4): 1933-1937.
"International Preliminary Report on Patentability", issued for International Application No. PCT/EP2016/072524, Mar. 27, 2018.
Clauss et al., "Efficient Non-Viral T-Cell Engineering by Sleeping Beauty Minicircles Diminishing DNA Toxicity and miRNAs Silencing the Endogenous T-Cell Receptors", Human Gene Ther., 2018, 29(5): 569-583.
Field et al., "Comparison of lentiviral and sleeping beauty mediated αβ T cell receptor gene transfer", PLoS One, 2013, 8(6): e68201.
Hostein et al., "Efficient Non-viral Gene Delivery into Human Hematopoietic Stem Cells by Minicircle Sleeping Beauty Transposon Vectors", Mol. Ther., 2018, 26: 1137-1153.
Kacherovsky et al., "Combination of Sleeping Beauty transposition and chemically induced dimerization selection for robust production of engineered cells", Nucleic Acids Research, 2012, 40(11): e85.
Magnani et al., "Transposon-Based CAR T Cells in Acute Leukemias: Where are We Going?", Cells, 2020, 9: 1337.
Monjezi et a., "Enhanced CAR T-cell engineering using non-viral Sleeping Beauty transposition from minicircle vectors", Leukemia, 2017, 31: 186-194.
Nakazawa et al., "Optimization of the PiggyBac Transposon System for the Sustained Genetic Modification of Human T-Lymphocytes", J Immunother, 2009, 32(8): 826-836.
Sun et al., "Cyclic GMP-AMP synthase is a cytosolic DNA sensor that activates the type I interferon pathway", Science, 2013, 339: 786-791.
Takaoka et al., "DAI (DLM-1/ZBP1) is a cytosolic DNA sensor and an activator of innate immune response", Nature, 2007, 448: 501-505.
Tian et al., "Gene modification strategies for next-generation CAR T cells against solid cancers", J. Hematology and Onc., 2020, 13:54.
Unterholzner et al., "IFI16 is an innate immune sensor for intracellular DNA", Nat Immunol, 2010, 11: 997-1004.
Bire et al., "Exogenous mRNA delivery and bioavailability in gene transfer mediated by piggyBac transposition", BMC Biotechnology, 2013, 13:75, 1-15.
Kacherovsky et al., "Multiplexed Gene Transfer to a Human T-cell Line by Combining Sleeping Beauty Transposon System With Methotrexate Selection", Biotechnology & Bioengineering, Mar. 2015, 112(7), 1429-1436.
Jin et al., "The hyperactive Sleeping Beauty transposase SB100X improves the genetic modification of T cells to express a chimeric antigen receptor", Gene Therapy, 2011, 1-8.
Communication pursuant to Rule 114(2) EPC and Third Party Observation regarding EP Application No. 16770015.2, published as 3352798 A1, issue date Jan. 4, 2022.
Galvan et al., "Genome-Wide Mapping of PiggyBac Transposon Integrations in Primary Human T Cells", J. Immunother., 2009, 32(8): 837-844.
Skipper et al., "DNA transposon-based gene vehicles—scenes from an evolutionary drive", Journal of Biomedical Science, 2013, 20:92, 23 pages.
Xue et al., "Stable gene transfer and expression in cord blood-derived CD34+ hematopoietic stem and progenitor cells by a hyperactive Sleeping Beauty transposon system", Blood, Aug. 2009, 114(7): 1319-1330.

(56) References Cited

OTHER PUBLICATIONS

Abramson et al., "Lisocabtagene maraleucel for patients with relapsed or refractory large B-cell lymphomas (Transcend NHL 001): a multicentre seamless design study", www.thelancet.com, published online Sep. 1, 2020, https://doi.org/10.1016/S0140-6736(20)31366-0.
Delauriere et al., "Mariner transposons as genetic tools in vertebrate cells", Genetica, 2009, 137: 9-17.
Kansagra et al., "Clinical utilization of Chimeric Antigen Receptor T-cells (CAR-T) in B-cell acute lymphoblastic leukemia (ALL)—an expert opinion from the European Society for Blood and Marrow Transplantation (EBMT) and the American Society for Blood and Marrow Transplantation (ASBMT)", Bone Marrow Transplantation, 2019, 54: 1868-1880.
Majzner et al., "Clinical lessons learned from the first leg of the CAR T cell journey", Nature Medicine, Sep. 2019, 25: 1341-1355.
Maude et al., "Tisagenlecleucel in Children and Young Adults with B-Cell Lymphoblastic Leukemiaz", The New England Journal of Medicine, 2018, 378: 439-448.
Munshi et al., "Idecabtagene Vicleucel in Relapsed and Refractory Multiple Myeloma", The New England Journal of Medicine, 2021, 384: 705-716.
Neelapu et al., "Axicabtagene Ciloleucel CAR T-Cell Therapy in Refractory Large B-Cell Lymphoma", The New England Journal of Medicine, 2017, 377: 2531-2544.
Prommersberger et al., "Caramba: a first-in-human clinical trial with SLAMF7 CAR-T cells prepared by virus-free Sleeping Beauty gene transfer to treat multiple myeloma", Gene Therapy, 2021, 28: 560-571.
Till et al., "CD20-specific adoptive immunotherapy for lymphoma using a chimeric antigen receptor with both CD28 and 4-1BB domains: pilot clinical trial results", Blood, Apr. 2012, 119(17): 3940-3950.
Wang et al., "KTE-X19 CAR T-Cell Therapy in Relapsed or Refractory Mantle-Cell Lymphoma", The New England Journal of Medicine, 2020, 382: 1331-1342.
Field et al., "Comparison of Lentiviral and Sleeping Beauty Mediated ab T Cell Receptor Gene Transfer", PLOS ONE, 2013, 8(6): e68201.
Huang et al., "Stable gene transfer and expression in human primary T cells by the Sleeping Beauty transposon system", Blood, 2006, 107(2): 483-491.
Hudecek et al., "Minicircle-Based Engineering of Chimeric Antigen Receptor (CAR) T Cells", Current Strategies in Cancer Gene Therapy, 2016, pp. 37-50.
Hudecek et al., "Non-viral therapeutic cell engineering with the Sleeping Beauty transposon system", Current Opinion in Genetics & Development, 2018, 52: 100-108.
Hudecek et al., "Going non-viral: the Sleeping Beauty transposon system breaks on through to the clinical side", Critical Reviews in Biochemistry and Molecular Biology, 2017, 52(4): 355-380.
Jonnalagadda et al., "Engineering Human T Cells for Resistance to Methotrexate and Mycophenolate Mofetil as an In Vivo Cell Selection Strategy", PLOS ONE, 2013, 8(6): e65519.
Papapetrou et al., "Gene Insertion Into Genomic Safe Harbors for Human Gene Therapy", Molecular Therapy, 2016, 24(4): 678-684.
Pavani et al., "Targeted Gene Delivery: Where to Land", Frontiers in Genome Editing, Jan. 2021, vol. 2, Article 609650.
Prommersberger et al., "Generation of CAR-T Cells with Sleeping Beauty Transposon Gene Transfer", Methods Mol Biol., 2022, 2521: 41-66.
Prommersberger et al., "Minicircles for CAR T Cell Production by Sleeping Beauty Transposition: A Technological Overview", Methods Mol Biol., 2022, 2521: 25-39.
Querques et al., "A highly soluble Sleeping Beauty transposase improves control of gene insertion", Nature Biotechnology, Dec. 2019, 37(12): 1502-1512.
Third Party Observations regarding EP Application No. 16770015.2, published as 3352798A1, Nov. 12, 2022.
Cai et al., "Driving DNA transposition by lentiviral protein transduction", Mobile Genetic Elements, 2014, 4: e29591, 8 pages.
Cruz et al., "Infusion of donor-derived CD19-redirected virus-specific T cells for B-cell malignancies relapsed after allogeneic stem cell transplant: a phase 1 study", Blood, 2013, 122(17): 2965-2973.
Gogishvili et al., "SLAMF7-CAR T cells eliminate myeloma and confer selective fratricide of SLAMF7+ normal lymphocytes", Blood, Dec. 28, 2017, 130(26): 2838-2847.
Hackett et al., "Evaluating Risks of Insertional Mutagenesis by DNA Transposons in Gene Therapy", Transl Res. 2013, 161(4): 265-283.
Hollis et al., "Stable gene transfer to human CD34+ hematopoietic cells using the Sleeping Beauty transposon", Experimental Hematology, 2006, 34: 1333-1343.
Hu, "Vectorology and Factor Delivery in Induced Pluripotent Stem Cell Reprogramming", Stem Cells and Development, 2014, 23(12): 1301-1315.
Krishnamurthy et al., "Genetic Engineering of T Cells to Target HERV-K, an Ancient Retrovirus on Melanoma", Clinical Cancer Research, Jul. 15, 2015, 21(14): 3241-3251.
Magnani et al., "Sleeping Beauty-engineered CAR T cells achieve antileukemic activity without severe toxicities", The Journal of Clinical Investigation, Nov. 2020, 130(11): 6021-6033.
Maiti et al., "Sleeping Beauty system to redirect T-cell specificity for human applications", J Immunother., 2013, 36(2): 112-123. doi: 10.1097/CJI.0b013e3182811ce9.
Morgan et al., "Genetic Modification of T Cells", The Cancer Journal, Mar./Apr. 2014, 20(2): 145-150.
Pesch et al., "Molecular Design, Optimization, and Genomic Integration of Chimeric B Cell Receptors in Murine B Cells", Frontiers in Immunology, Nov. 2019, vol. 10, Article 2630, 16 pages.
Porter et al., "Chimeric antigen receptor T cells persist and induce sustained remissions in relapsed refractory chronic lymphocytic leukemia", Sci Transl Med., Sep. 2, 2015, 7(303): 303ra139. doi:10.1126/scitranslmed.aac5415, 25 pages.
Singh et al., "Manufacture of T cells using the Sleeping Beauty system to enforce expression of a CD19-specific chimeric antigen receptor", Cancer Gene Therapy, Jan. 16, 2015, 22: 95-100.
Singh et al., "Sleeping beauty generated CD19 CAR T-Cell therapy for advanced B-Cell hematological malignancies", Frontiers in Immunology, 2022, DOI 10.3389/fimmu.2022.1032397, 10 pages.
Till et al., "Adoptive immunotherapy for indolent non-Hodgkin lymphoma and mantle cell lymphoma using genetically modified autologous CD20-specific T cells", Blood, 2008, 112(6): 2261-2271.
Zhang et al., "Viral vectors for gene delivery in tissue engineering", Advanced Drug Delivery Reviews, 2006, 58: 515-534.
Cambridge English Dictionary, Definition of "transduction", URL: https://dictionary.cambridge.org/us/dictionary/english/transduction, retrieved on Oct. 11, 2023.
Cribbs et al., "Simplified production and concentration of lentiviral vectors to achieve high transduction in primary human T cells", BMC Biotechnology, 2013, 13:98, 8 pages.
Dietz et al., "Minicircle DNA is Superior to Plasmid DNA in Eliciting Antigen-specific CD8+ T-cell Responses", Molecular Therapy, 2013, 21(8): 1526-1535.
Presti et al., "Efficient lentiviral transduction method to gene modify cord blood CD8+ T cells for cancer therapy applications", Molecular Therapy: Methods & Clinical Development, 2021, 21: 357-368.
Brentjens et al., "CD19-targeted T cells rapidly induce molecular remissions in adults with chemotherapy-refractory acute lymphoblastic leukemia", Sci Transl Med., 2013, 5(177): 177ra38, 19 pages.
Brown et al., "Bioactivity and Safety of IL13Rα2-Redirected Chimeric Antigen Receptor CD8+ T Cells in Patients with Recurrent Glioblastoma", Clinical Cancer Research, 2015, 21(18): 4062-4072.
Garfall et al., "Chimeric Antigen Receptor T Cells against CD19 for Multiple Myeloma", The New England Journal of Medicine, 2015, 373(11): 1040-1047.
Kalos et al., "T Cells with Chimeric Antigen Receptors Have Potent Antitumor Effects and Can Establish Memory in Patients with Advanced Leukemia", Sci Transl Med., 2011, 3(95): 95ra73, 21 pages.

(56) References Cited

OTHER PUBLICATIONS

Kochenderfer et al., "Eradication of B-lineage cells and regression of lymphoma in a patient treated with autologous T cells genetically engineered to recognize CD19", Blood, 2010, 116(20): 4099-4102.
Kochenderfer et al., "B-cell depletion and remissions of malignancy along with cytokine-associated toxicity in a clinical trial of anti-CD19 chimeric-antigen-receptor-transduced T cells", Blood, 2012, 119(12): 2709-2720.
Lee et al., "T cells expressing CD19 chimeric antigen receptors for acute lymphoblastic leukaemia in children and young adults: a phase 1 dose-escalation trial", Lancet. 2015, 385(9967): 517-528.
Ritchie et al., "Persistence and Efficacy of Second Generation CAR T Cell Against the LeY Antigen in Acute Myeloid Leukemia", Molecular Therapy, 2013, 21(11): 2122-2129.
Morton et al., "Simultaneous Deletion of Endogenous TCRαβ for TCR Gene Therapy Creates an Improved and Safe Cellular Therapeutic", Molecular Therapy, Jan. 2020, 28(1): 64-74.
Polic et al., "How αβ T cells deal with induced TCRα ablation", PNAS, 2001, 98(15): 8744-8749.
Van Loenen et al., "Mixed T cell receptor dimers harbor potentially harmful neoreactivity", PNAS, 2010, 107(24): 10972-10977.
Communication pursuant to Rule 114(2) EPC—Third Part Observations, issued for European Application No. 16770015.2, Sep. 17, 2025.

* cited by examiner

A

B

C

D

A

B, continued

B, continued

B, continued

C

D

A

A, continued
MC-MC
mRNA-MC
35.7
64.3
0
0
48.3
51.7
0
0
CD8
tEGFR

| | V1 | V2 | V3 | V4 | V5 | V6 | V7 | V8 |
|---|---|---|---|---|---|---|---|---|
| A | 0,30974692 | 0,316018594 | 0,316535084 | 0,325905704 | 0,318527263 | 0,318453479 | 0,315354534 | 0,324872722 |
| C | 0,191987014 | 0,186600753 | 0,189109422 | 0,18018151 | 0,185936693 | 0,177746624 | 0,186379399 | 0,178263115 |
| G | 0,178705822 | 0,191470523 | 0,180255294 | 0,19058511 | 0,17885339 | 0,193979193 | 0,174942817 | 0,188666716 |
| T | 0,319560245 | 0,305910131 | 0,314100199 | 0,303327677 | 0,316682653 | 0,309820704 | 0,323323249 | 0,308197447 |
| other | 0 | 0 | 0 | 0 | 0 | 0 | 0 | 0 |

| | V9 | V10 | V11 | V12 | V13 | V14 | V15 | V16 |
|---|---|---|---|---|---|---|---|---|
| A | 0,304582011 | 0,320593227 | 0,305836346 | 0,321699993 | 0,307385819 | 0,332989006 | 0,314395337 | 0,344499373 |
| C | 0,183280455 | 0,188371578 | 0,195676234 | 0,189994835 | 0,187633734 | 0,177156349 | 0,184977496 | 0,172065225 |
| G | 0,187633734 | 0,185641555 | 0,185789124 | 0,18571534 | 0,181878551 | 0,187486165 | 0,176344721 | 0,179665019 |
| T | 0,3245038 | 0,30539364 | 0,312698296 | 0,302589833 | 0,323101896 | 0,302368479 | 0,324282447 | 0,303770383 |
| other | 0 | 0 | 0 | 0 | 0 | 0 | 0 | 0 |

Figure 12, continued

| | V17 | V18 | V19 | V20 | V21 | V22 | V23 | V24 |
|---|---|---|---|---|---|---|---|---|
| A | 0,318158341 | 0,33003763 | 0,305983915 | 0,330332768 | 0,305688777 | 0,33623552 | 0,29617059 | 0,326791116 |
| C | 0,180255294 | 0,175533092 | 0,187338597 | 0,184165867 | 0,187264812 | 0,176566074 | 0,181435844 | 0,173688482 |
| G | 0,172803069 | 0,190363757 | 0,181730982 | 0,18387073 | 0,185936693 | 0,184018299 | 0,177894193 | 0,189994835 |
| T | 0,328783295 | 0,304065521 | 0,324946506 | 0,301630635 | 0,321109717 | 0,303180108 | 0,344499373 | 0,309525566 |
| other | 0 | 0 | 0 | 0 | 0 | 0 | 0 | 0 |

| | V25 | V26 | V27 | V28 | V29 | V30 | **V31** | **V32** |
|---|---|---|---|---|---|---|---|---|
| A | 0,301187929 | 0,358075703 | 0,263631668 | 0,684497897 | 0,170810891 | 0,485501365 | **0,000221353** | **0,998081606** |
| C | 0,181583413 | 0,160997565 | 0,228362724 | 0,043090091 | 0,233675201 | 0,169482771 | **0,00066406** | **0,000147569** |
| G | 0,187338597 | 0,226370545 | 0,199734376 | 0,076588209 | 0,177746624 | 0,173540913 | **0,000442706** | **0,001328119** |
| T | 0,329890061 | 0,254556187 | 0,308271231 | 0,195823803 | 0,417767284 | 0,17147495 | **0,998671881** | **0,000442706** |
| other | 0 | 0 | 0 | 0 | 0 | 0 | **0** | **0** |

▲ Insertion site

Figure 12, continued

| | V33 | V34 | V35 | V36 | V37 | V38 | V39 | V40 |
|---|---|---|---|---|---|---|---|---|
| A | 0,176639858 | 0,41702944 | 0,204751715 | 0,30908286 | 0,257138641 | 0,323618387 | 0,303844167 | 0,337120933 |
| C | 0,1783369 | 0,177377702 | 0,07894931 | 0,202833321 | 0,230576256 | 0,189699697 | 0,19058511 | 0,177746624 |
| G | 0,170884675 | 0,234855751 | 0,038589242 | 0,233675201 | 0,161218918 | 0,185936693 | 0,175237955 | 0,185862909 |
| T | 0,474138567 | 0,170737106 | 0,677709732 | 0,254408618 | 0,351066185 | 0,300745222 | 0,330332768 | 0,299269534 |
| other | 0 | 0 | 0 | 0 | 0 | 0 | 0 | 0 |

| | V41 | V42 | V43 | V44 | V45 | V46 | V47 | V48 |
|---|---|---|---|---|---|---|---|---|
| A | 0,300597654 | 0,319191323 | 0,303327677 | 0,32568435 | 0,306426621 | 0,334169557 | 0,308861507 | 0,316756438 |
| C | 0,189256991 | 0,193462702 | 0,19191323 | 0,182468826 | 0,191691876 | 0,174942817 | 0,182911533 | 0,179591234 |
| G | 0,177156349 | 0,190954032 | 0,182173688 | 0,191101601 | 0,181214491 | 0,179074744 | 0,179222312 | 0,190658895 |
| T | 0,332989006 | 0,296391943 | 0,322585405 | 0,300745222 | 0,320667011 | 0,311812883 | 0,329004648 | 0,312993433 |
| other | 0 | 0 | 0 | 0 | 0 | 0 | 0 | 0 |

Figure 12, continued

| | V49 | V50 | V51 | V52 | V53 | V54 | V55 | V56 |
|---|---|---|---|---|---|---|---|---|
| A | 0,307754741 | 0,313731277 | 0,306279053 | 0,301851988 | 0,305910131 | 0,320371873 | 0,305836346 | 0,322364052 |
| C | 0,186158046 | 0,184313436 | 0,184608574 | 0,196192725 | 0,184682358 | 0,183796945 | 0,195381096 | 0,185125065 |
| G | 0,17951745 | 0,196487862 | 0,191101601 | 0,198406257 | 0,187707519 | 0,195454881 | 0,185346418 | 0,181657198 |
| T | 0,326569763 | 0,305467424 | 0,318010773 | 0,30354903 | 0,321699993 | 0,3003763 | 0,31343614 | 0,310853686 |
| other | 0 | 0 | 0 | 0 | 0 | 0 | 0 | 0 |

| | V57 | V58 |
|---|---|---|
| A | 0,314838043 | 0,322732974 |
| C | 0,184239652 | 0,175016601 |
| G | 0,181878551 | 0,191691876 |
| T | 0,319043754 | 0,310558548 |
| other | 0 | 0 |

Figure 17, continued
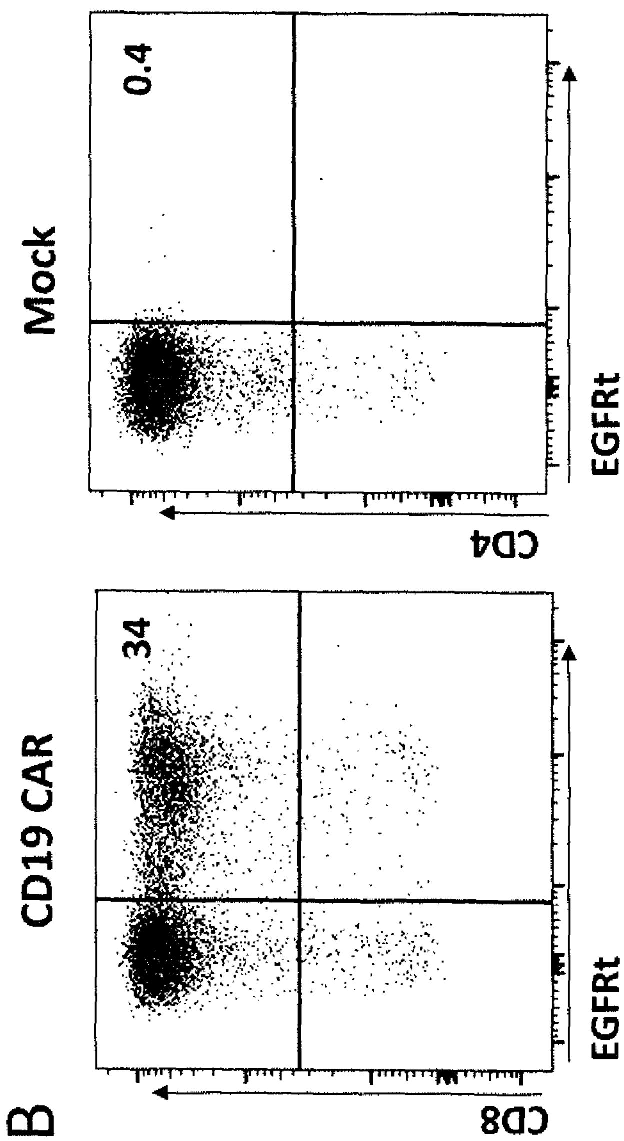

Figure 17, continued
C
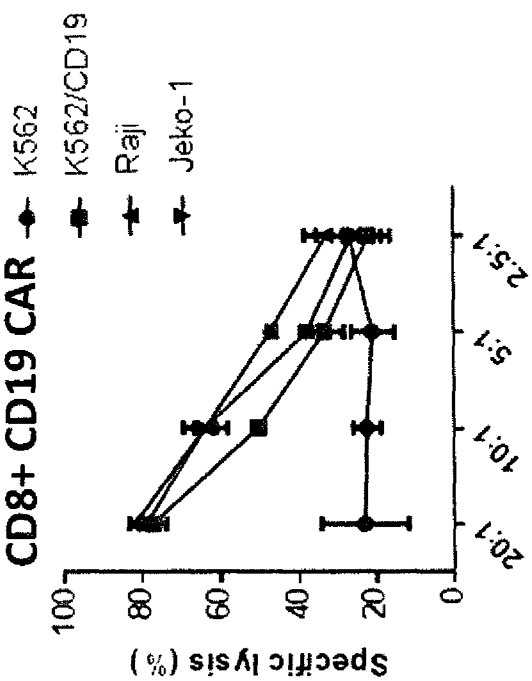

Figure 19, continued
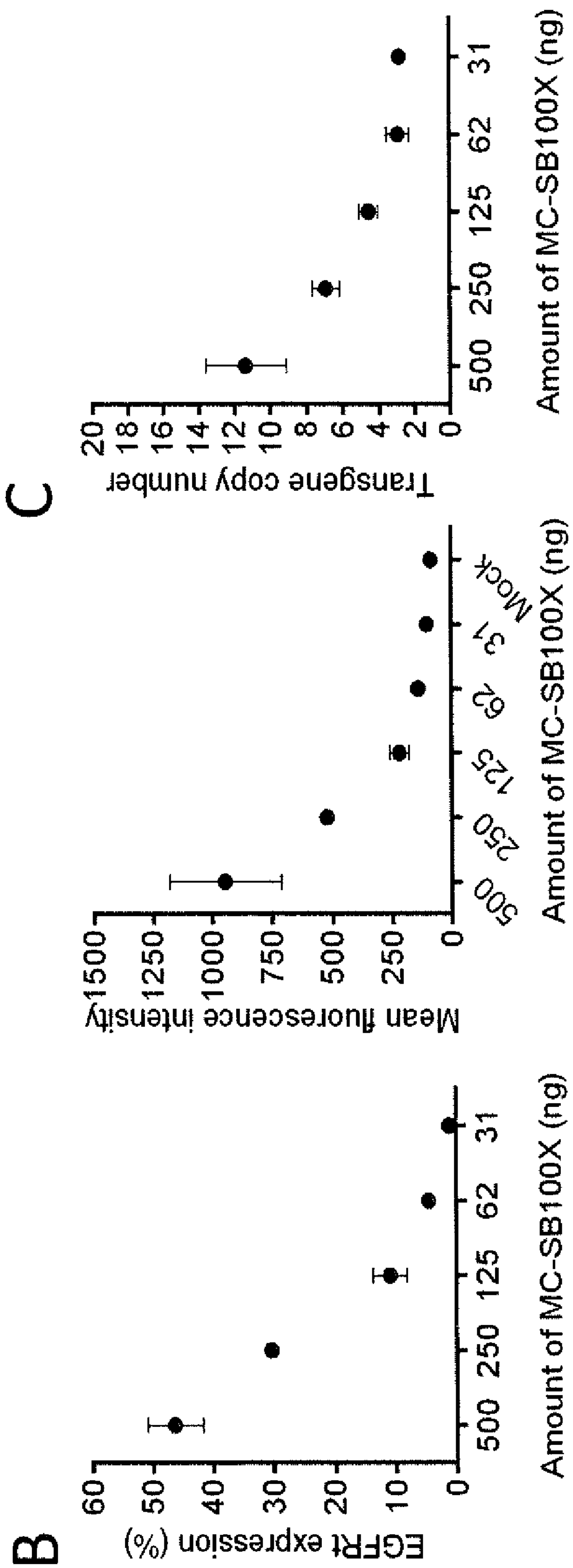

Figure 20, continued
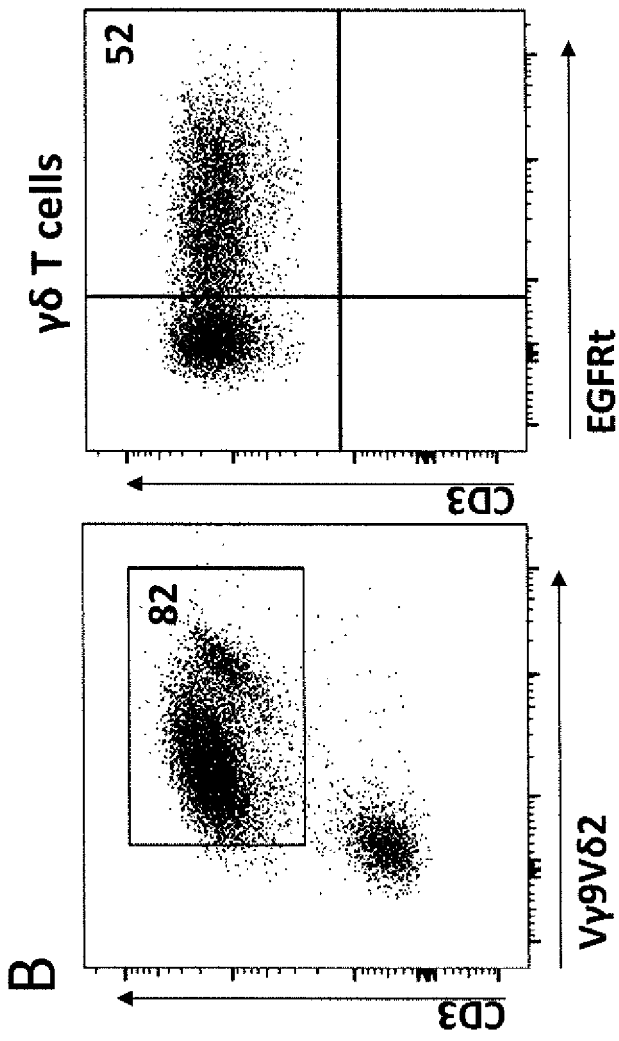

Figure 20, continued
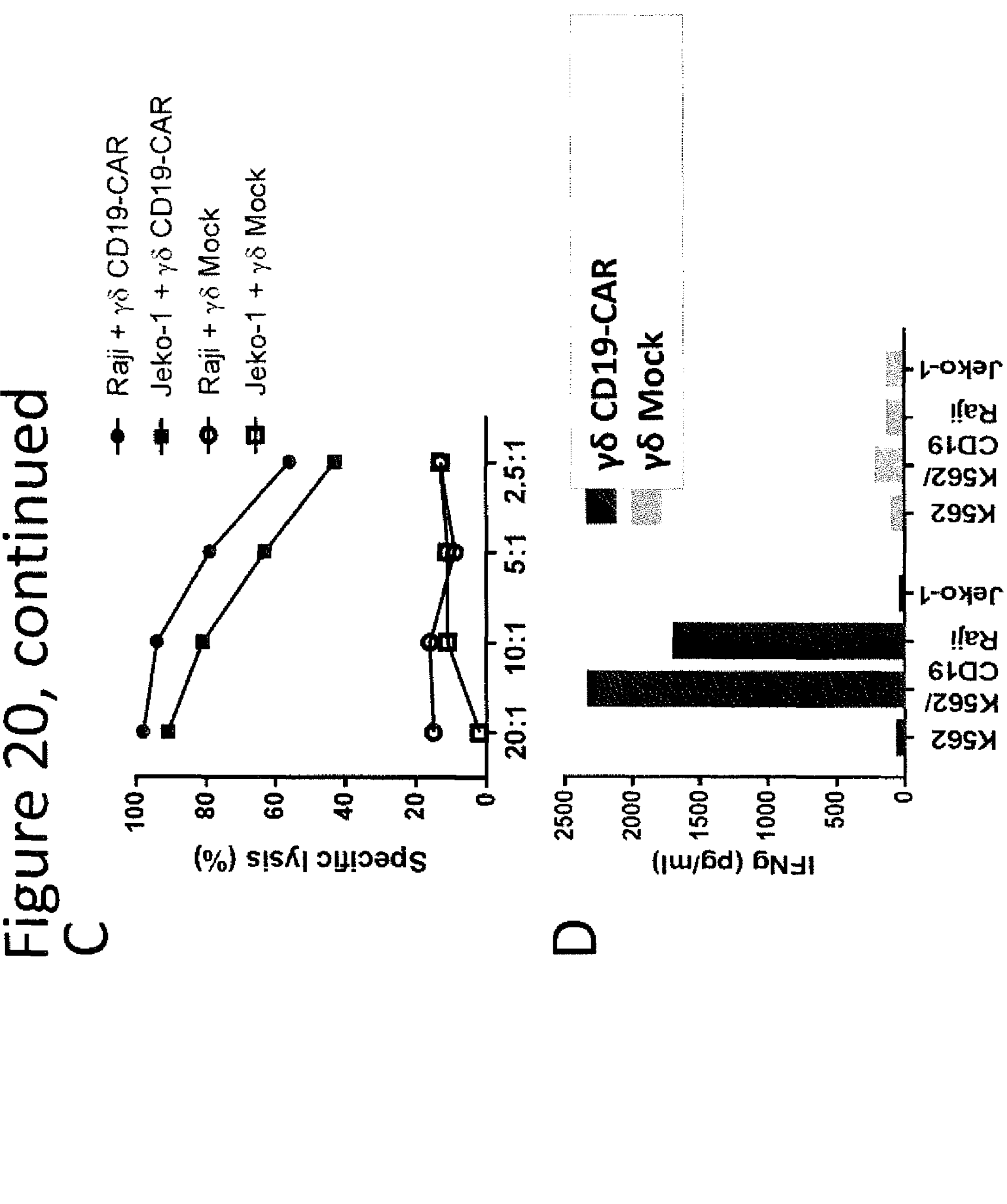

METHOD FOR HIGH LEVEL AND STABLE GENE TRANSFER IN LYMPHOCYTES

CROSS-REFERENCE TO RELATED APPLICATIONS

This application is a § 371 national phase of International Application No. PCT/EP2016/072524, filed on Sep. 22, 2016, which claims the benefit of European Application No. 15002732.4, filed on Sep. 22, 2015, and European Application No. 16153490.4, filed on Jan. 29, 2016, all of which applications are incorporated by reference herein.

FIELD OF THE INVENTION

The invention includes methods and technologies for gene transfer and methods and technologies for immunotherapy.

BACKGROUND OF THE INVENTION

Genetically modified cells and tissues are increasingly being utilized in diagnostic and therapeutic applications in living organisms. Genetic modification is performed e.g. by introducing one or several transgenes to endow cells with novel properties, or by introducing one or several modifiers of genes in order to modulate or delete distinct properties and functions. An impressive example for the therapeutic utility of such gene-modified cells is the use of engineered T cells that are modified by gene-transfer to express a T-cell receptor (TCR) or synthetic chimeric antigen receptor (CAR) that recognize a molecule expressed by a tumor cell and thus confer anti-tumor specificity. There is compelling evidence for the anti-tumor function and curative potential of such engineered TCR- and CAR-modified T cells from both pre-clinical tumor models and clinical trials in patients with advanced chemo- and radiotherapy-refractory malignancies (Hudecek *Blood* 2010; Hudecek *Cancer Immunol Res* 2013; Hudecek *Cancer Immunol Res* 2015; Hudecek *Leukemia* 2015; Kalos *Science Transl Med* 2011; Grupp *N Engl J Med* 2013; Davila *Science Transl Med* 2014; Maude *N Engl J Med* 2014).

The most commonly used strategy to accomplish gene-transfer into T cells is the use of viral delivery systems, e.g. retroviral, lentiviral, adenoviral vectors. Viral delivery systems have been used to stably integrate transgenes including TCRs and CARs into human T lymphocytes and enabled the manufacture of tumor-reactive TCR-/CAR T lymphocytes for pre-clinical and clinical applications. For instance, in particular, engineered T cells equipped with a synthetic chimeric antigen receptor (CAR) specific for CD19 have demonstrated remarkable efficacy against B-cell malignancies in pilot studies[*Refs.* 1-3]. In all clinical trials reported to date that showed efficacy of CD19-CAR T-cell therapy, integrating lentiviral (LV) or gamma-retroviral (RV) vectors were employed to accomplish CAR gene transfer and expression. However, there are multiple conceptual, technical and strategic disadvantages associated with the use of viral gene-transfer vectors, including an undesired potential for transgene silencing over time, the preferential integration into transcriptionally active sites of the genome with associated undesired activation of other genes (e.g. oncogenes) and genotoxicity; as well as the expense and cumbersome effort of manufacturing, storing and handling integrating viruses—the latter of which have precluded their more widespread use for the manufacture of gene-modified T cells in therapeutic applications. Thus, there are persistent concerns associated with viral vectors regarding safety, as well as cost and scale of vector production required for establishing CAR T cell therapy on a global level.

An alternative strategy to accomplish stable gene-transfer is the transposon technology. Transposons, or transposable elements (TEs), are genetic elements with the capability to stably integrate into host cell genomes, a process that is called transposition (Ivics *Mobile DNA* 2010). TEs were already postulated in the 1950s by Barbara McClintock in genetic studies with maize, but the first functional models for transposition have been described for bacterial TEs at the end of the 1970s (Shapiro *PNAS* 1979). Meanwhile it is clear that TEs are present in the genome of every organism, and genomic sequencing has revealed that approximately 45% of the human genome is transposon derived (International Human Genome Sequencing Consortium *Nature* 2001). However, as opposed to invertebrates, where functional (or autonomous) TEs have been identified, humans and most higher vertebrates do not contain functional TEs. It has been hypothesized that evolutionary selective pressure against the mutagenic potential of TEs has led to their functional inactivation millions of years ago during evolution.

Autonomous TEs comprise DNA that encodes a transposase enzyme located in between two inverted terminal repeat sequences (ITRs), which are recognized by the transposase enzyme encoded in between the ITRs and which can catalyze the transposition of the TE into any double stranded DNA sequence. There are two different classes of transposons: class I, or retrotransposons, that mobilize via an RNA intermediate and a "copy-and-paste" mechanism, and class II, or DNA transposons, that mobilize via excision-integration, or a "cut-and-paste" mechanism (Ivics *Nat Methods* 2009). Bacterial, lower eukaryotic (e.g. yeast) and invertebrate transposons appear to be largely species specific, and cannot be used for efficient transposition of DNA in vertebrate cells. Only after a first active transposon had been artificially reconstructed by sequence shuffling of inactive TEs from fish, which was therefore called "Sleeping Beauty" (Ivics *Cell* 1997), did it become possible to successfully achieve DNA integration by transposition into vertebrate cells, including human cells. Sleeping Beauty is a class II DNA transposon belonging to the Tcl/marine rfamily of transposons (Ni *Genomics Proteomics* 2008). In the meantime, additional functional transposons have been identified or reconstructed from different species, including *Drosophila*, frog and even human genomes, that all have been shown to allow DNA transposition into vertebrate and also human host cell genomes. Each of these transposons have advantages and disadvantages that are related to transposition efficiency, stability of expression, genetic payload capacity, etc.

BRIEF DESCRIPTION OF THE INVENTION

The method disclosed herein describes a novel technology offering unparalleled efficiency, flexibility, utility and speed for the stable integration of transgenes into lymphocytes and other mammalian cells. The novel method is based on the use of an mRNA-encoded transposase (e.g. sleeping beauty transposase) in combination with a minicircle DNA-encoded transposable element. The novel method enables higher gene-transfer rates and is at the same time less toxic than the conventional approach, which is the use of plasmid DNA-encoded transposase in combination with a plasmid DNA-encoded transposable element.

The following effects will contribute to the higher gene-transfer rates achieved by the minicircles according to the invention:

the longer half-life of minicircles as compared to plasmids,
the easier migration of minicircles through cytoplasm and into the nucleus as compared to plasmids,
the easier mobilization of the transposon from small supercoiled MCs compared to large circular plasmids.

According to the invention, these effects are not limited to minicircles but also apply to any other DNA encoding a transposable element containing an expression cassette for a transgene, provided that such DNA has a smaller size than a conventional plasmid which is suitable as a donor plasmid for transposable elements. Thus, according to the invention, any DNA encoding a transposable element containing an expression cassette for a transgene can also be used, provided that the DNA encoding the transposable element is a DNA encoding the transposable element as defined below.

Due to the higher gene-transfer rates achieved according to the invention, the implementation of the methods and uses of the invention under good manufacturing practice (GMP) will be facilitated. For instance, when the invention is used to generate CAR T cells, CD3/CD28 stimulation can be used to activate T cells prior to transfection, and unlike state of the art methods, the present invention does not require the use of feeder cells to expand the CAR T cells to achieve therapeutically relevant doses of the CAR T cells.

According to the invention, the lower amounts of transfected minicircle DNA (as compared to plasmid DNA) contribute to the reduction in toxicity achieved by the minicircles. Again, this effect is not limited to minicircles but also applies to any other DNA encoding a transposable element containing an expression cassette for a transgene, provided that such DNA has a smaller size than a conventional plasmid which is suitable as a donor plasmid for transposable elements. Thus, according to the invention, any DNA encoding a transposable element containing an expression cassette for a transgene can also be used, provided that the DNA encoding the transposable element is a DNA encoding the transposable element as defined below.

A further advantage of the invention is that due to the lack of antibiotic resistance genes in minicircles, horizontal gene transfer of the antibiotic resistance genes to host bacteria and unintended integration of the antibiotic resistance genes into the host genome is excluded.

According to the invention, it was found that mRNA can be used as a source of the transposase. This finding was unexpected, because it was not known whether mRNA, which is short-lived, would be a suitable source to supply sufficient amounts of the transposase for the invention. According to the invention, the use of mRNA as a source of the transposase has two advantages: Firstly, because the transposase supplied by the mRNA is short-lived, there is a lower risk that already integrated transposons are re-mobilized. Secondly, the supply of the transposase as mRNA eliminates the risk of unintentional integration of a transposase expression cassette into the host genome, which could lead to uncontrollable, continuous transposition of genomically integrated transposons.

The present invention is also advantageous in that it provides a close-to-random integration profile of the transposons carrying the transgene, without preference for highly expressed or cancer related genes. Additionally, when using the invention, a significantly higher proportion of transgene integrations occurs in genomic safe harbors compared to LV integrations, close to the perfect score expected for random integration. Accordingly, the invention can be used to manufacture recombinant mammalian cells such as lymphocytes (e.g. CAR T cells) using virus-free transposition. The superior safety profile, high level stable transposition rate and ease-of-handling of the vectors of the invention make the invention a preferred gene-transfer strategy, e.g. in advanced cellular and gene-therapy.

Applications of the invention include but are not limited to the stable integration of a transgene encoding an immune receptor (e.g. a T-cell receptor or synthetic chimeric antigen receptor) into human T lymphocytes, with the immune receptor conferring specificity for a molecule expressed by a tumor cell. The transposase mRNA and transposon minicircle DNA may be introduced into lymphocytes by methods including but not limited to electrotransfer such as electroporation and nucleofection.

(A) Schematic representation of minicircle (MC) DNA production. MC-DNA elements are generated by a site specific intramolecular recombination from a parental plasmid mediated by PhiC31 integrase. The Parental Plasmid DNA contains several engineered I-SceI restriction sites that ultimately lead to the digestion of the bacterial backbone but not the MC-DNA. The MC-DNA contains exclusively the transgene and its promotor but no longer carries the bacterial origin of replication or the antibiotic resistance markers.

(B) Schematic representation of MC vectors prepared from parental conventional plasmids through site specific intramolecular recombination. MCs contain exclusively the transgene and its promotor, but no bacterial origin of replication and antibiotic resistance genes. EF1, elongation factor-1 alpha promoter; CMV, cytomegalovirus promotor; ORI, bacterial origin of replication; AntibioR, antibiotic resistance gene; LIR, left inverted repeat; RIR, right inverted repeat; open circle=recombination site.

(C) Restriction digest and analysis of purified MC DNAs by gel electrophoresis. 250 ng of MC-GFP, MC-CD19 CAR or MC-SB100X was digested with PmeI or PacI and analyzed by gel electrophoresis on a 0.8% agarose gel. Lane M: 1 kbp DNA ladder (PlasmidFactory); Lane 1: PacI digested MC-GFP; Lane 2: PmeI digested MC-CD19 CAR; Lane 3: PmeI digested MC-SB100X.

(D) Analysis of in vitro transcribed SB100X mRNA by gel electrophoresis. The ARCA capped SB100X mRNA migrates as a distinct single band at about 1400 bp on the denaturing agarose gel. Lane M: RNA marker (FlashGel, Lonza); Lane 1: SB100X mRNA.

Figure 2:
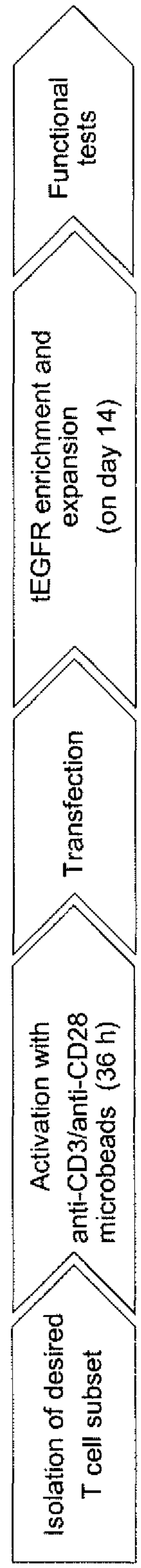
Figure 2:
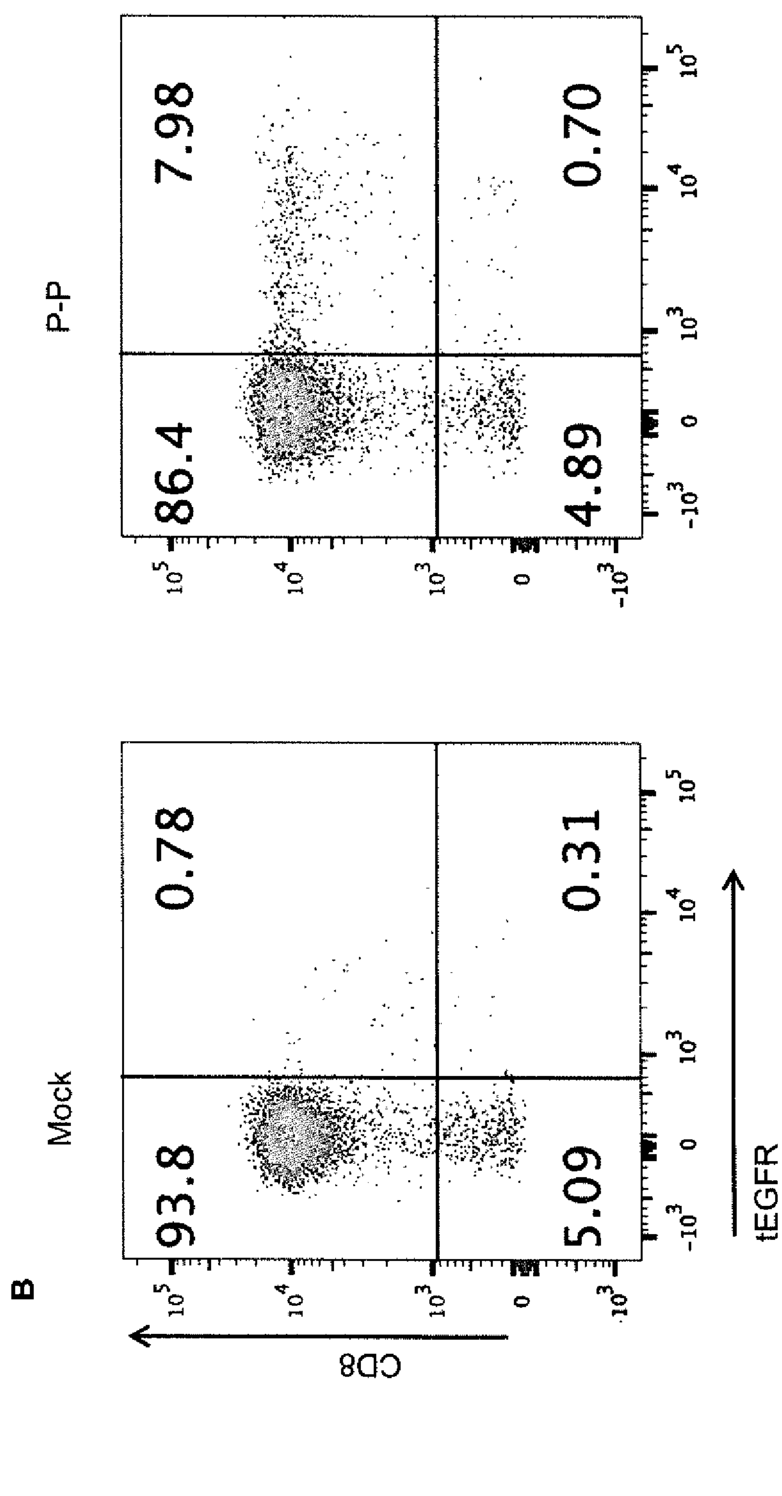
Figure 2:
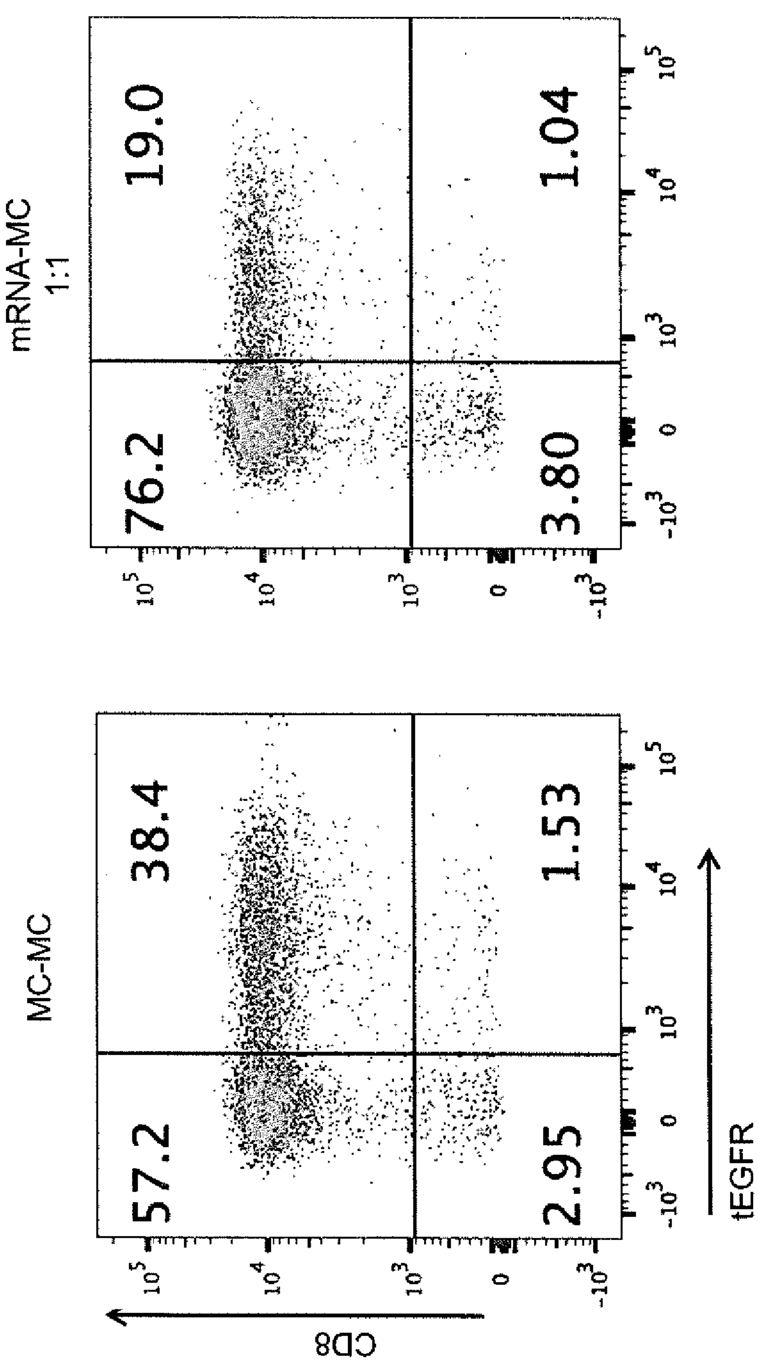
Figure 2:
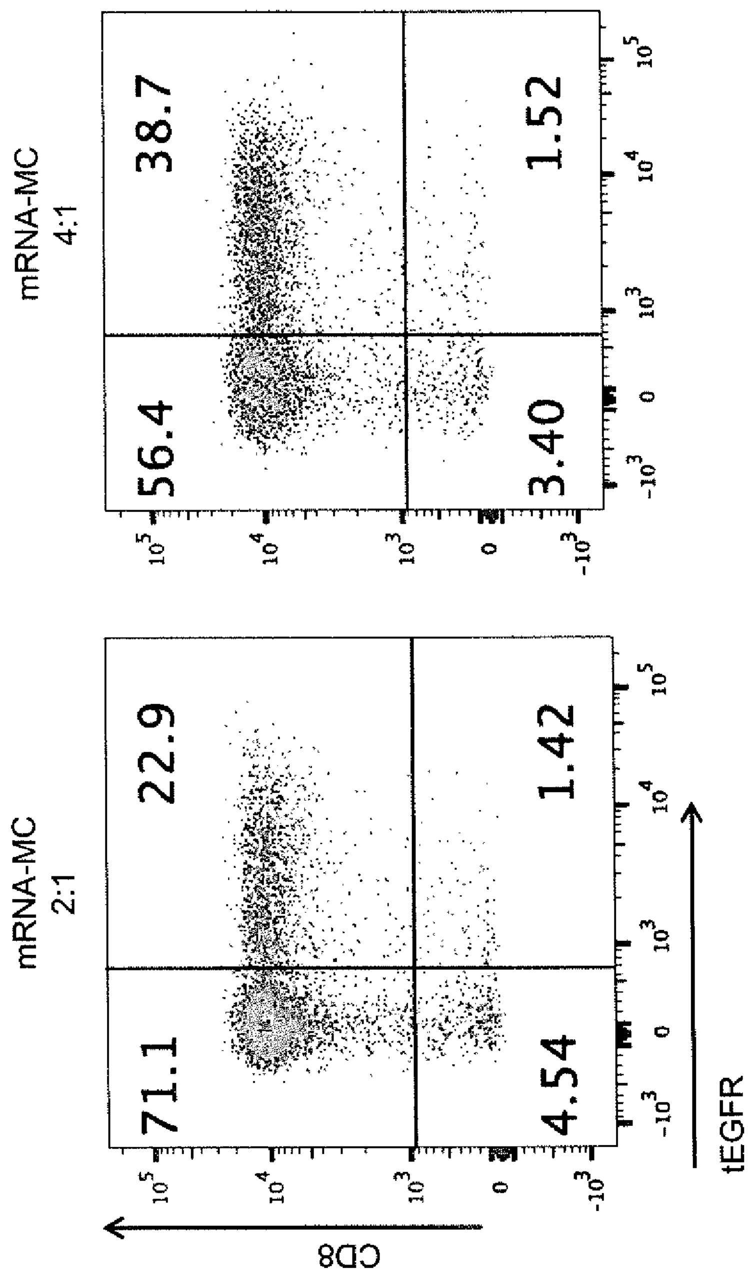
Figure 2:
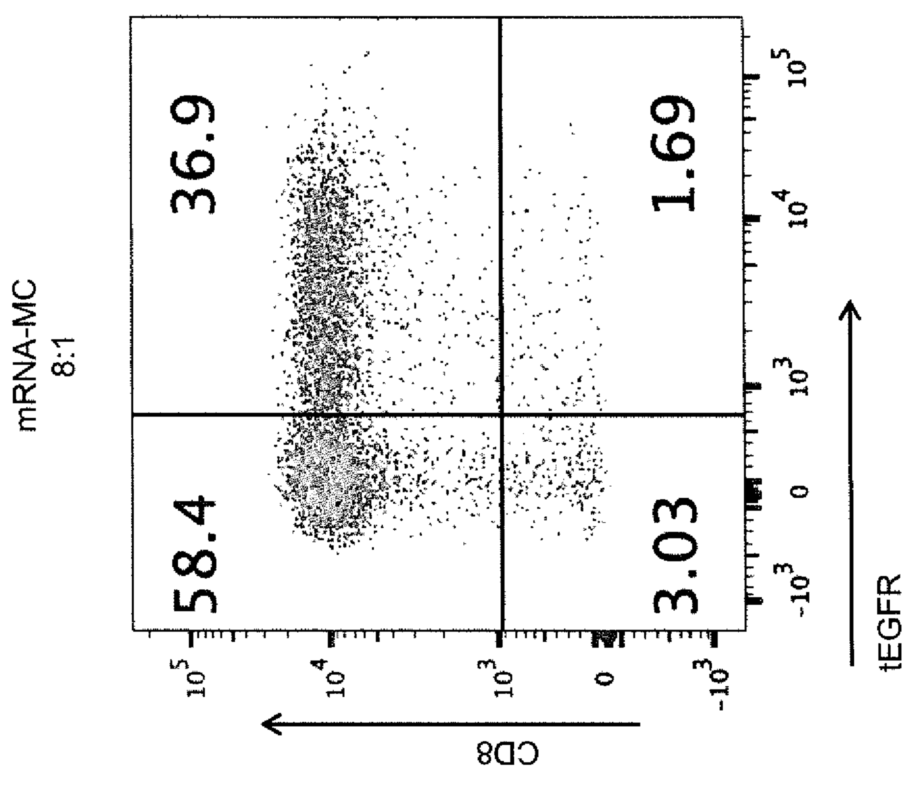
Figure 2:
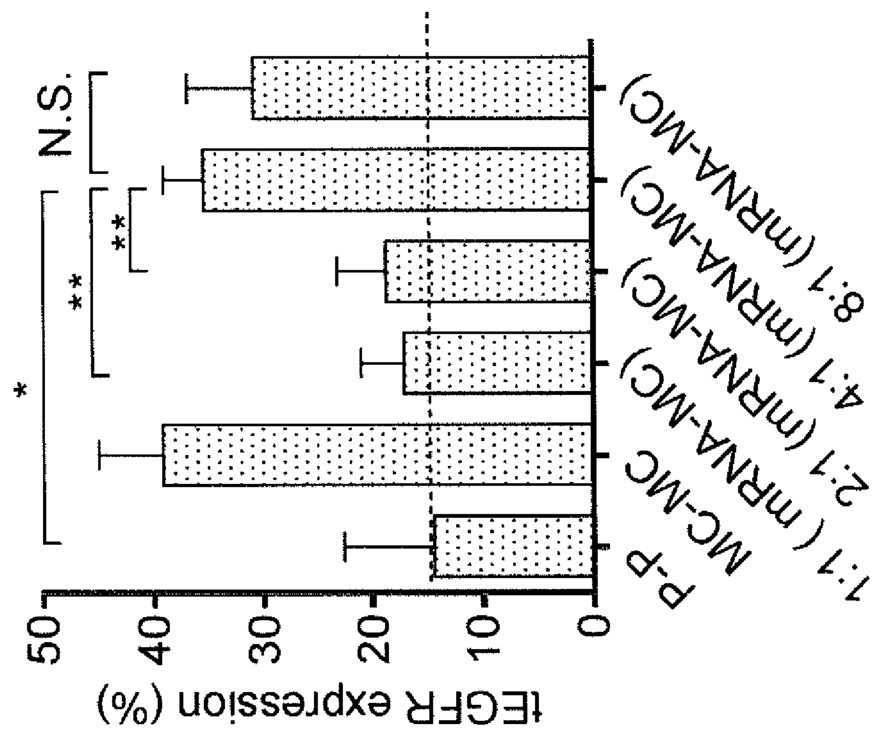
Figure 2:
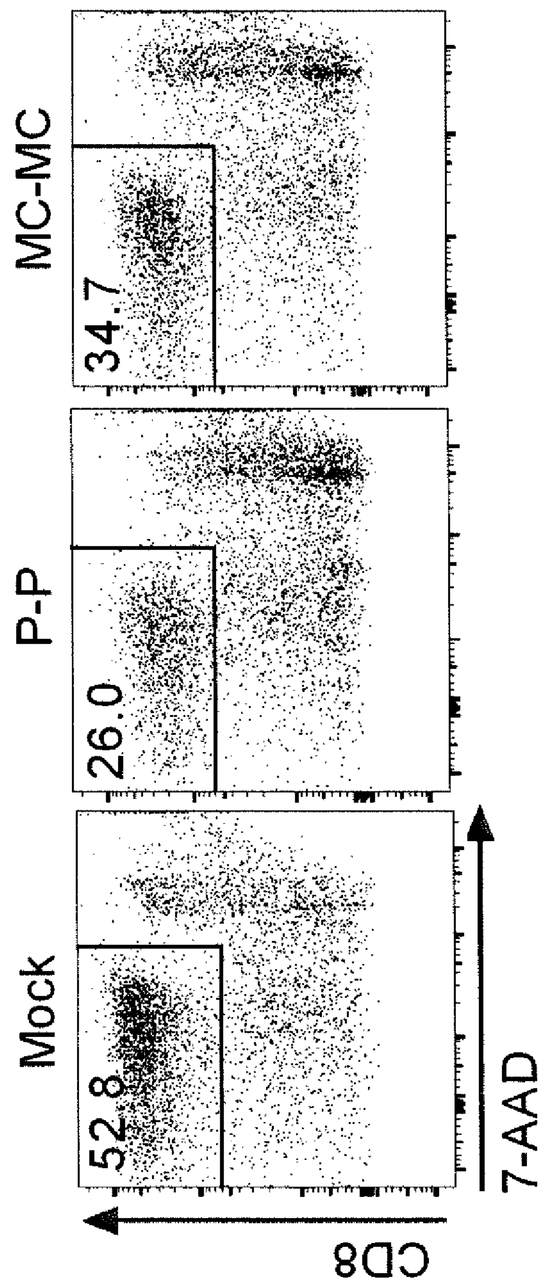

FIG. 2. Titration of SB100X mRNA for maximal transposition from MC-DNA.

(A) Protocol for SB-mediated reprogramming of T lymphocytes. Activation of T cells with anti-CD3/anit-CD28 microbeads for about 36 hours, co-transfection of transposase (as plasmid-DNA, MC-DNA or mRNA) and transposon donor (as plasmid-DNA or MC-DNA) using a 4D-nucleofector system. Serial flow cytometric analyses to determine the percentage of transgene-positive T cells. In a typical experiment, the transposon contained a transgene encoding a CD19-specific CAR. Here, transgene-positive T cells were enriched using a tEGFR transduction marker contained within the transgene cassette and expanded by antigen-specific stimulation with CD19+ EBV-transformed B cells (TM-LCL) for 7 days prior to functional testing.

(B) Flow cytometric analysis of tEGFR expression on day 14, in CD8+ T-cell lines that were nucleofected with the indicated ratios of mRNA SB100X and MC-CD19 CAR (mRNA-MC), plasmids (P-P) or MC-DNAs (MC-MC). Amounts used for nucleofection of 2×10e6 T cells: P-P: 1 ug of SB100X DNA+1 ug of pT2; MC-MC: equimolar amounts as P-P; mRNA-MC: same amount of MC as MC-MC (equimolar to P-P), multiple of mRNA. Mock=nucleofection was performed in solution that contained no transposase and no transposon.

(C) Comparison of tEGFR expression after transfection with different ratios of SB100X mRNA and MC-CD19 CAR, P-P or MC-MC on day 14 post-transfection. Data represent the mean values±SD for three independent experiments. Statistical analysis was performed using Student t test, *p<0.01, **p<0.001, indicate statistically significant differences between data.

(D) Viability and expansion of gene-modified CD8+ T cells. At 48-hours post-transfection, 7-AAD staining was performed to determine the percentage of viable T cells (dot plots and left diagram). The yield of CAR-modified T cells was calculated from the absolute number and the percentage of EGFRt+ T cells obtained by day 14 after transfection (right diagram). Data shown are mean values±SD.

Figure 3:
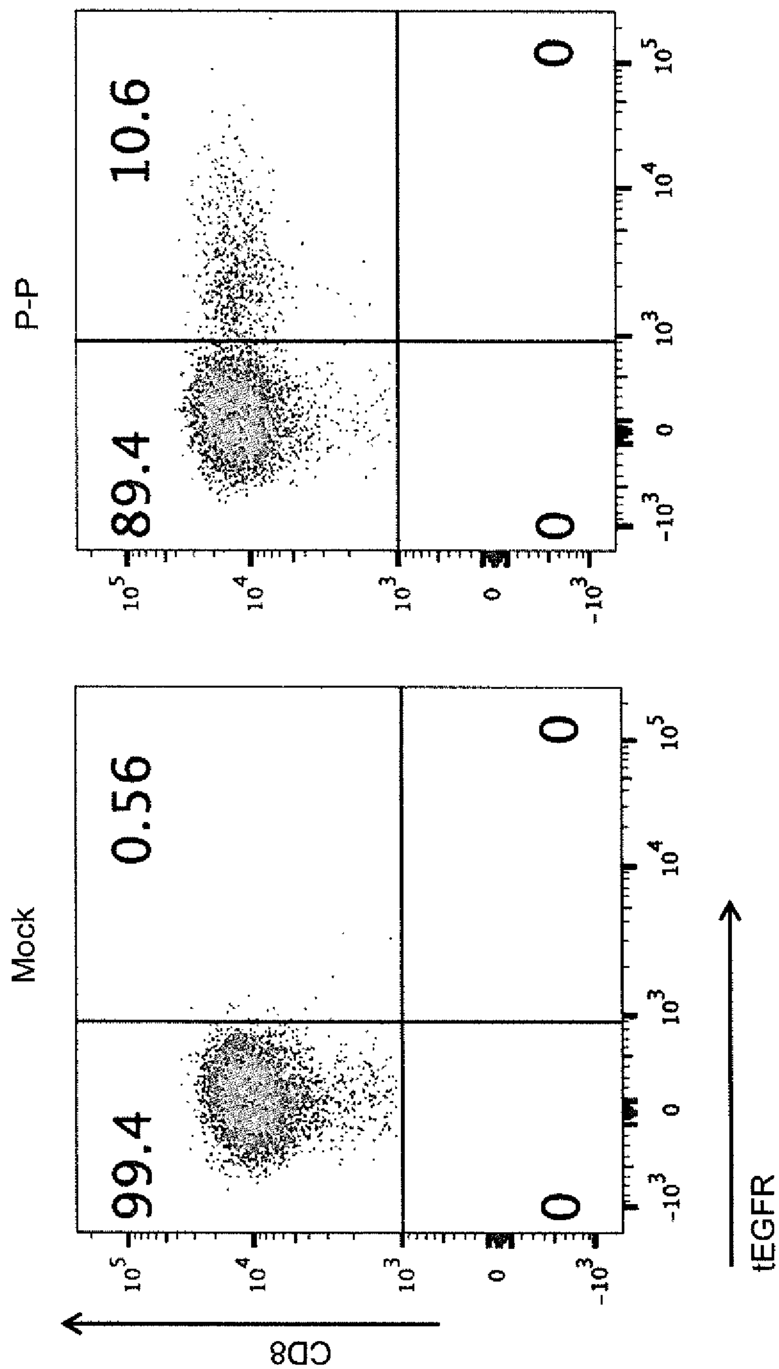
Figure 3:
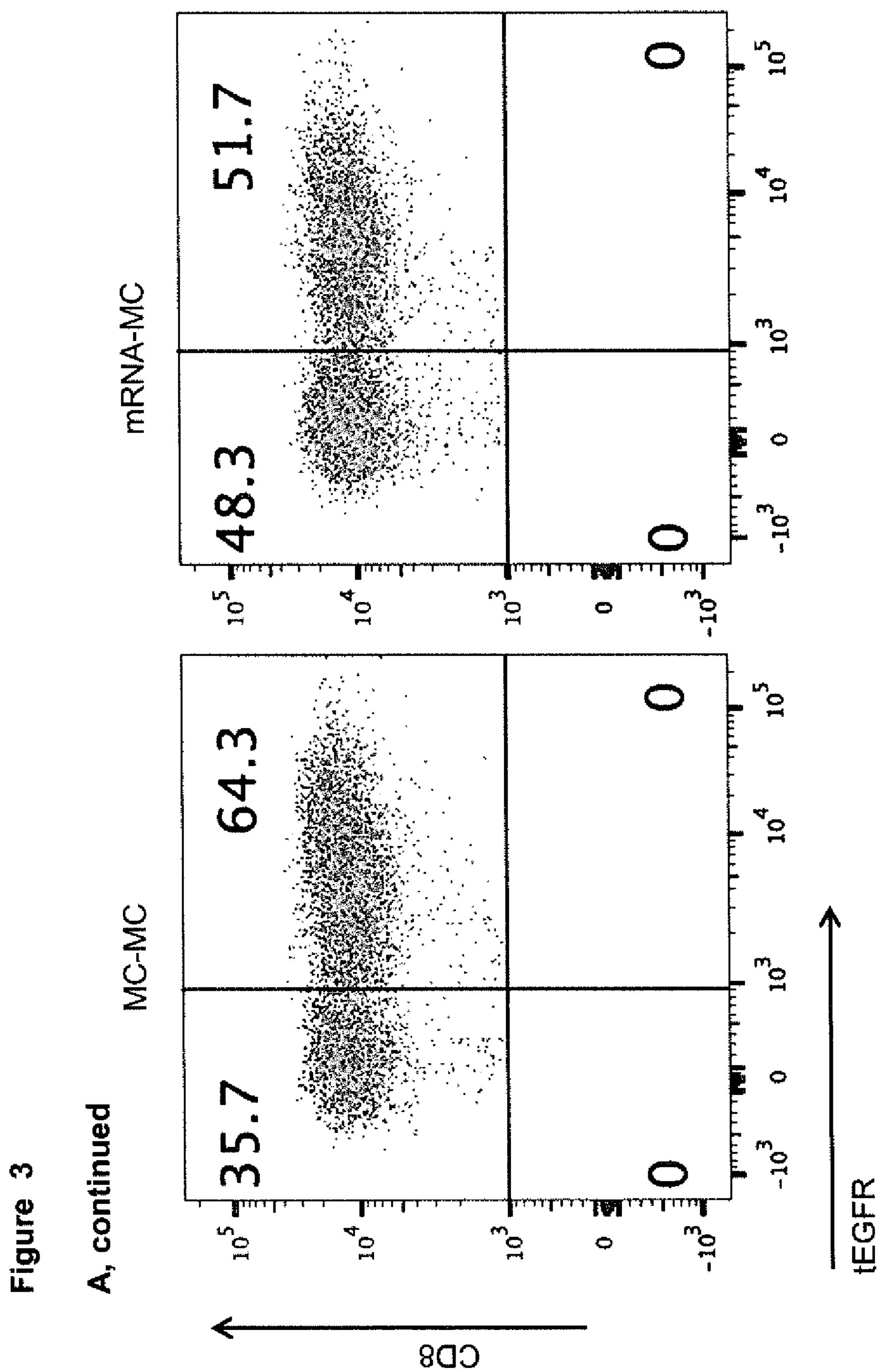
Figure 3:
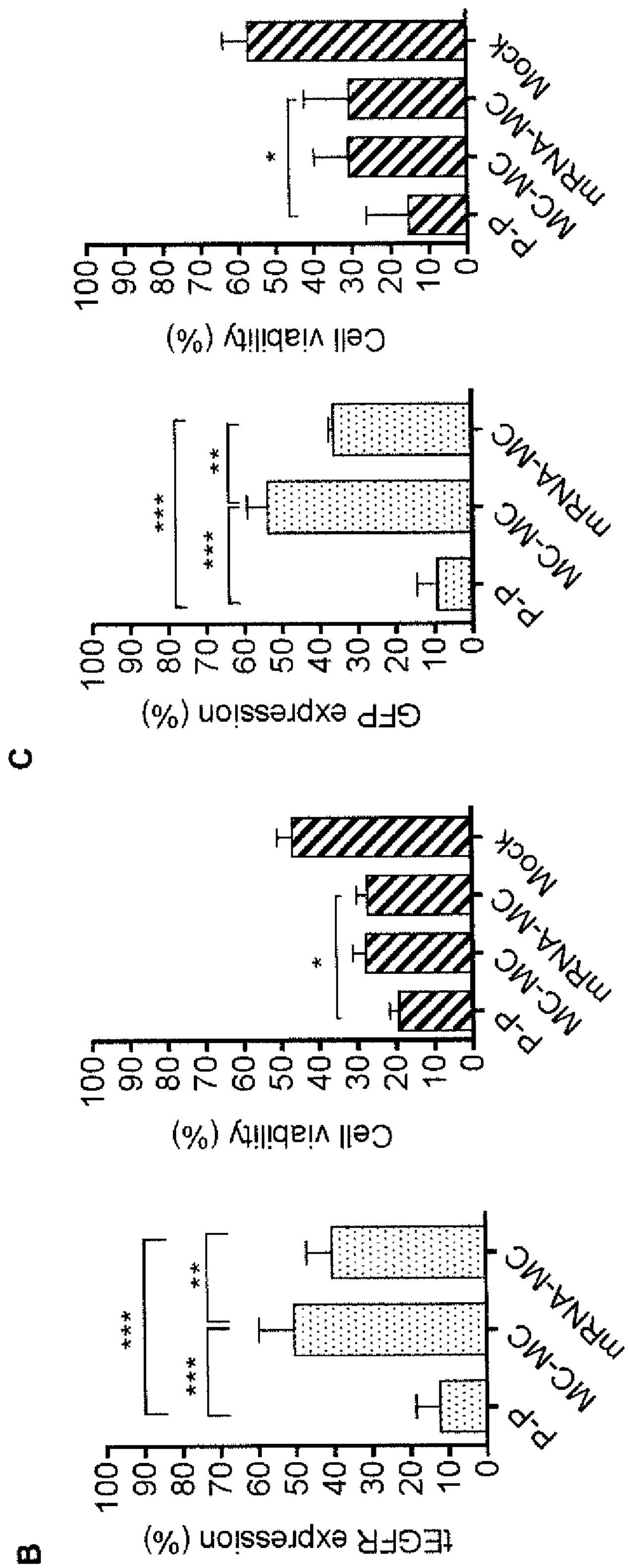
Figure 3:
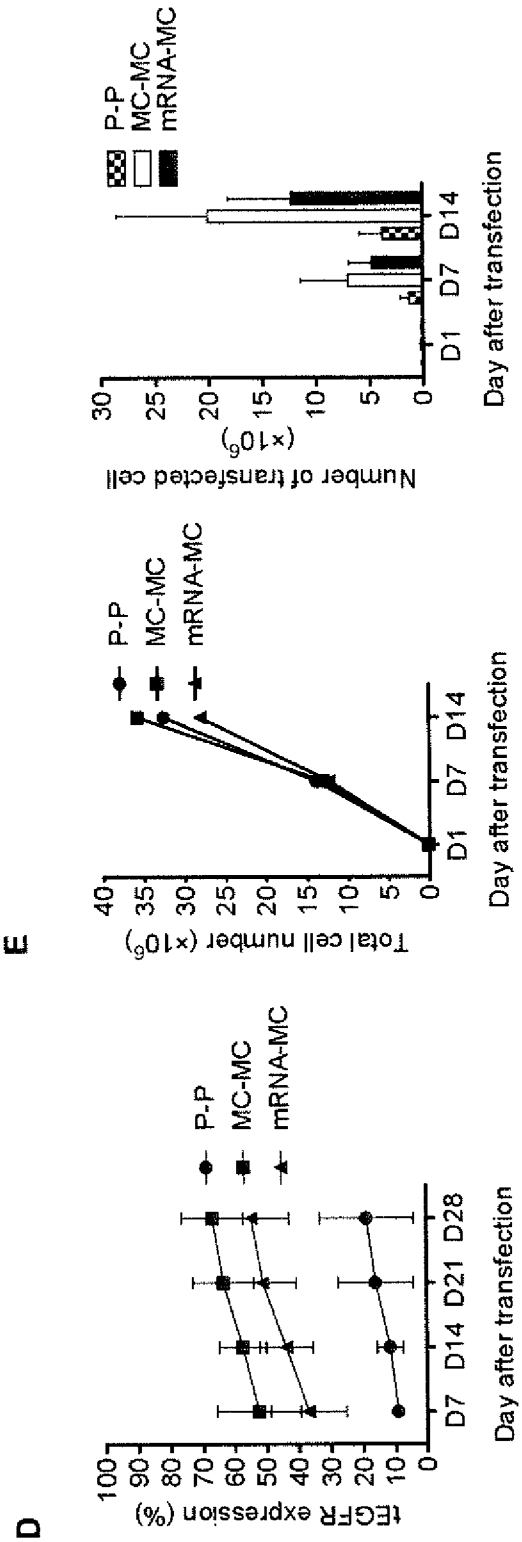

FIG. 3. Transposition with SB100X mRNA from MC-DNA improves genes transfer rate and target cell viability compared to transposition with/from conventional plasmid-DNA.

(A) Percentage of tEGFR positive T cells after transfection with plasmids (P-P), minicircle DNAs (MC-MC, equimolar) or SB100X mRNA and MC-CD19 CAR (mRNA-MC, 4:1 ratio) assessed by flow cytometry on day 14 post-transfection.

(B), (C) Comparison of the tEGFR or GFP expression and cell viability after transfection with P-P, MC-MC or mRNA-MC. tEGFR or GFP expression and cell viability were assessed by flow cytometry analysis. Mean values±SD for six (B) or three (C) independent experiments are shown. Statistical analysis was performed using Student t test. *p<0.01, p<0.001, *p<0.001 indicate statistically significant differences between data.

(D) Stability of tEGFR surface expression over 28 days in culture with IL-2 assessed by flow cytometry analysis after transfection with P-P, MC-MC or mRNA-MC.

(E) Expansion of T cells within two weeks after transfection with P-P, MC-MC or mRNA-MC. The number of CD8+ T cell number was determined with counting by trypan blue exclusion staining. The total number of cells (left graph) or number of genetically modified cells (right graph) is shown. Data represent the mean values±SD for three independent experiments.

Figure 4:
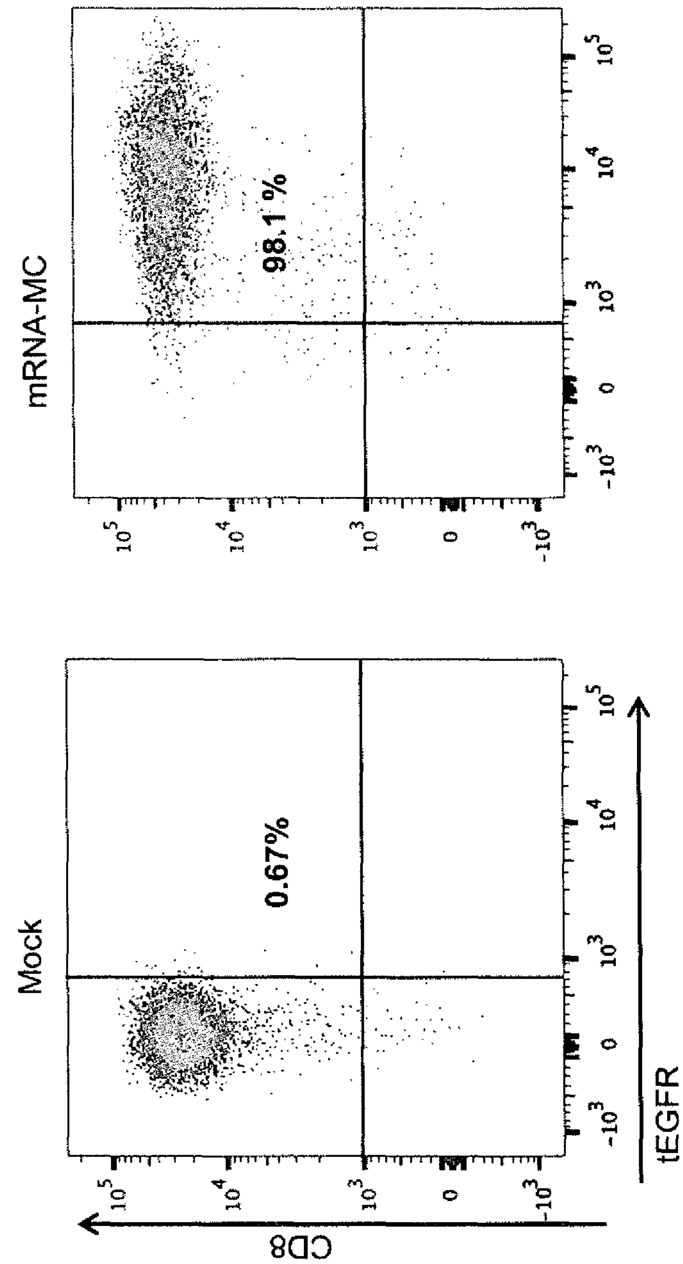
Figure 4:
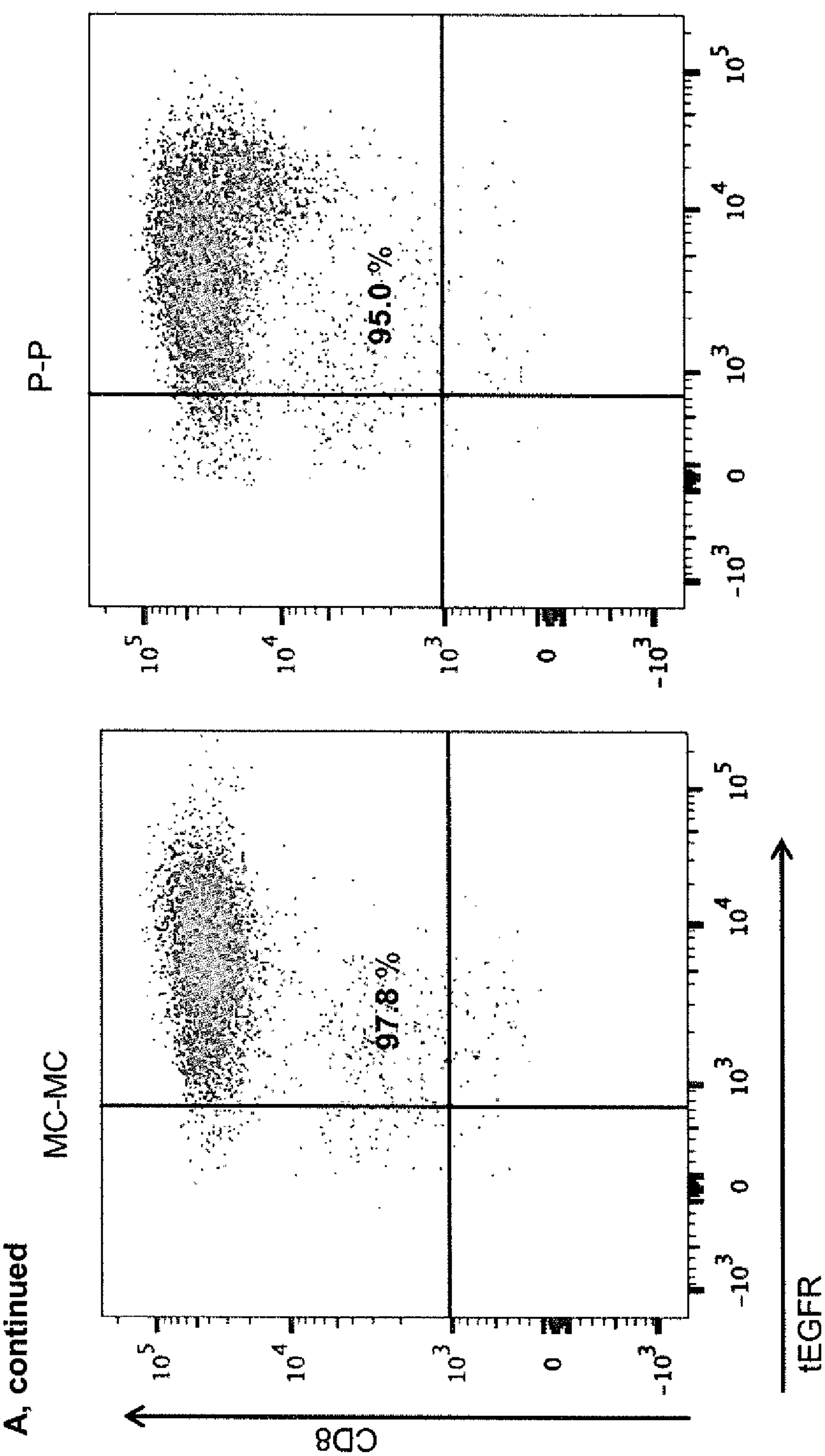
Figure 4:
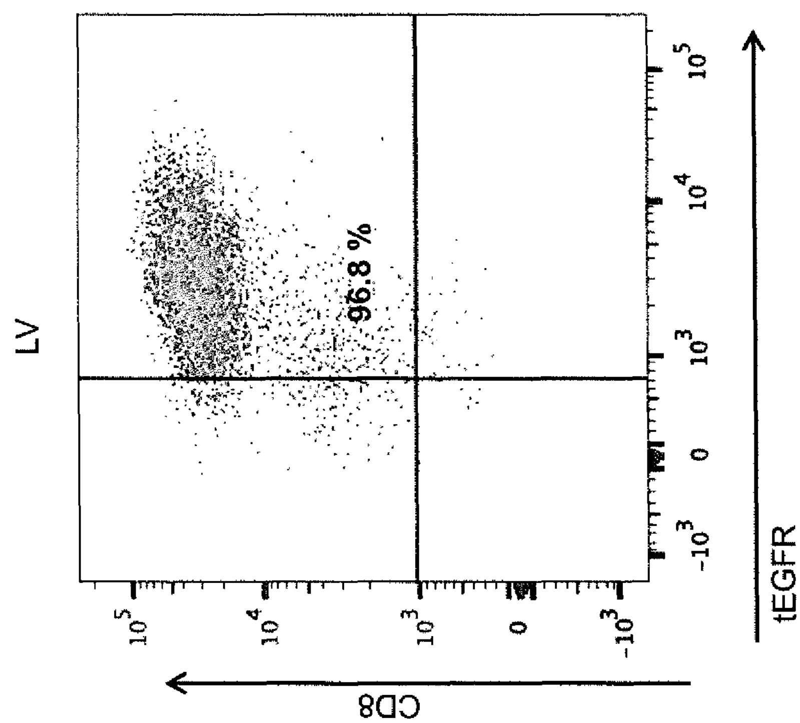
Figure 4:
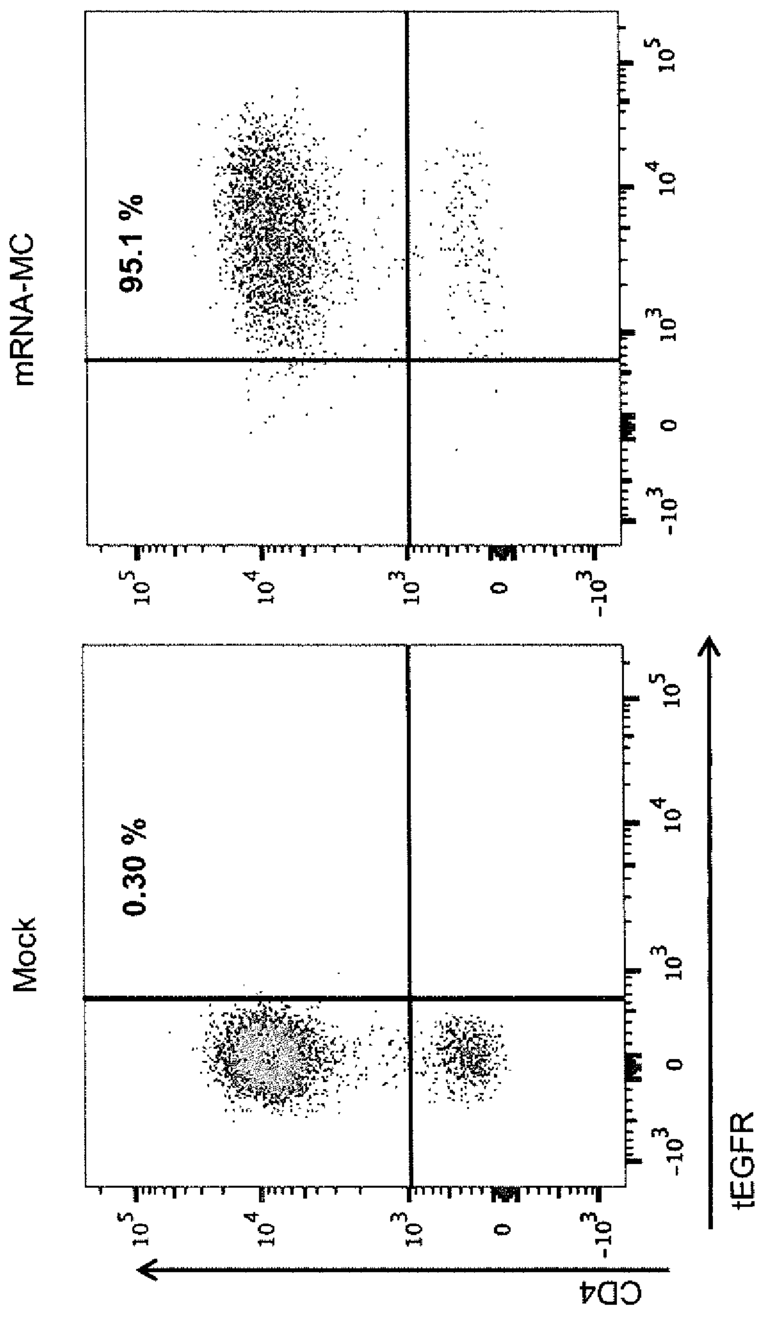
Figure 4:
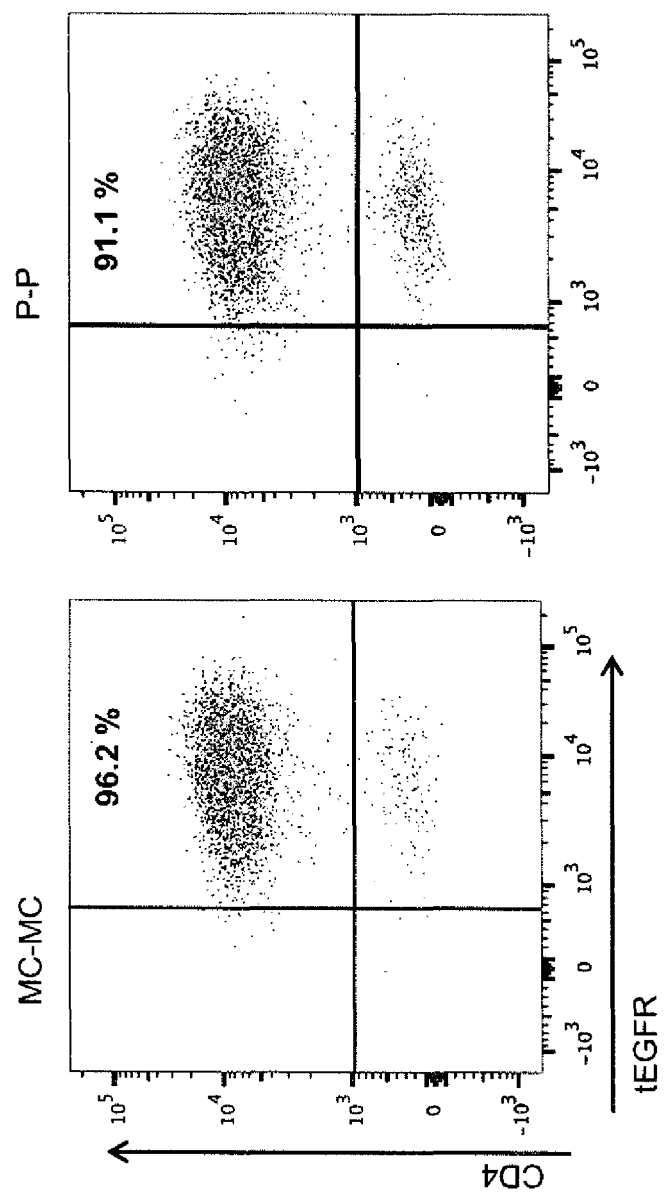
Figure 4:
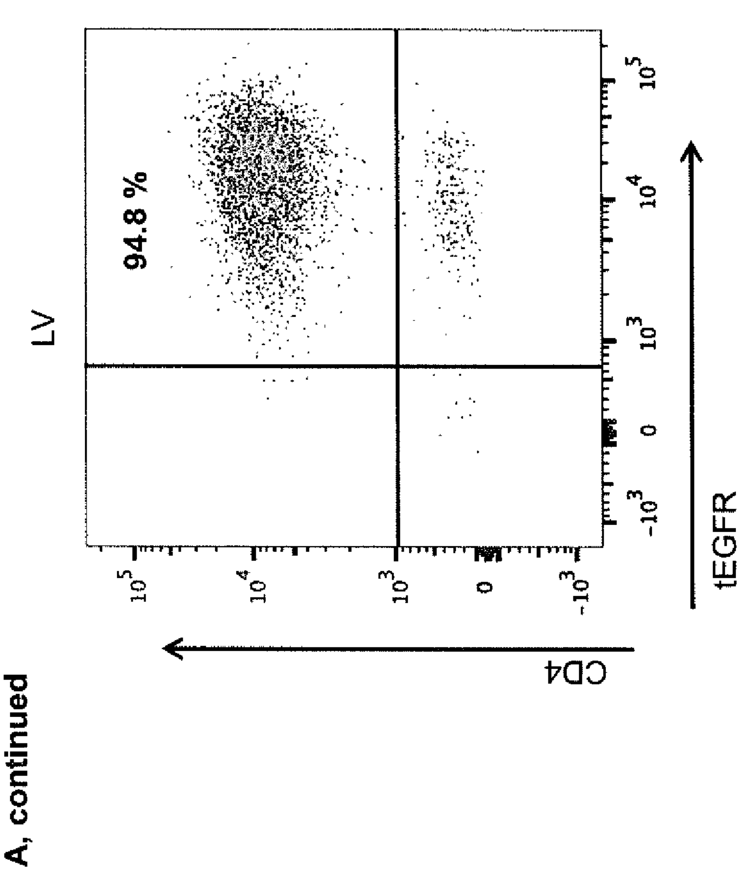
Figure 4:
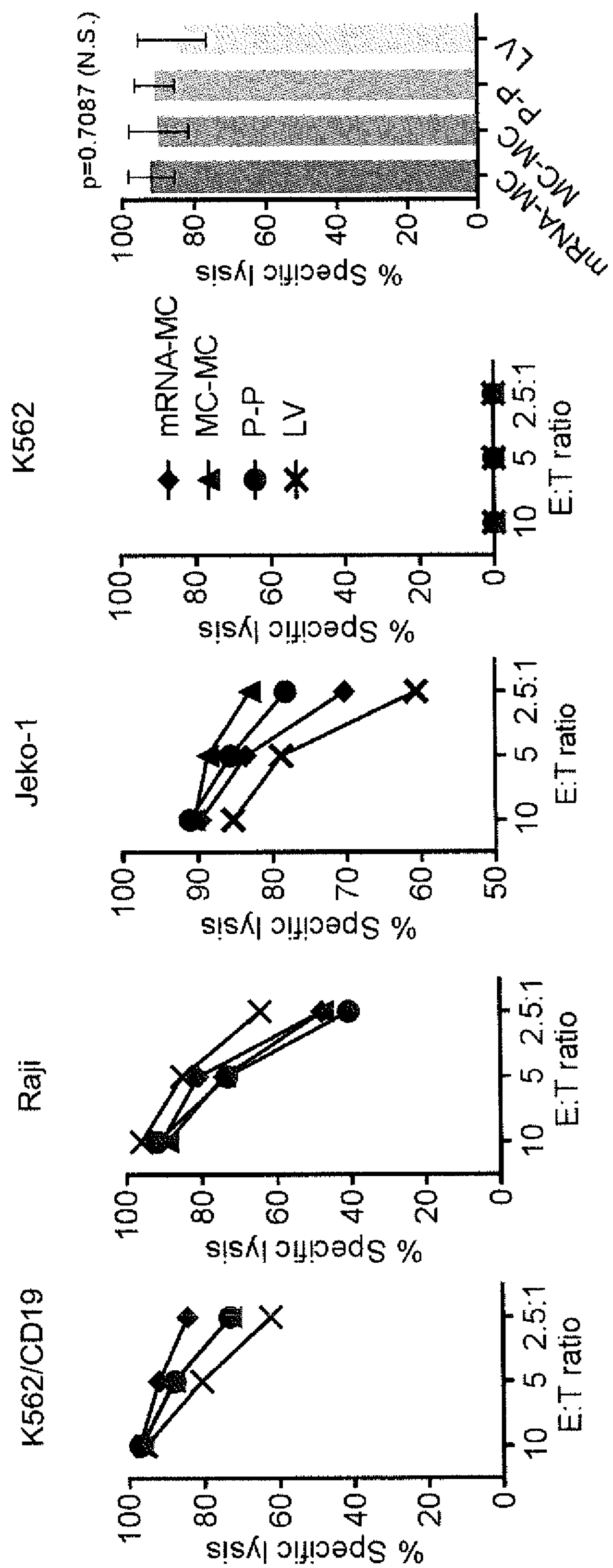
Figure 4:
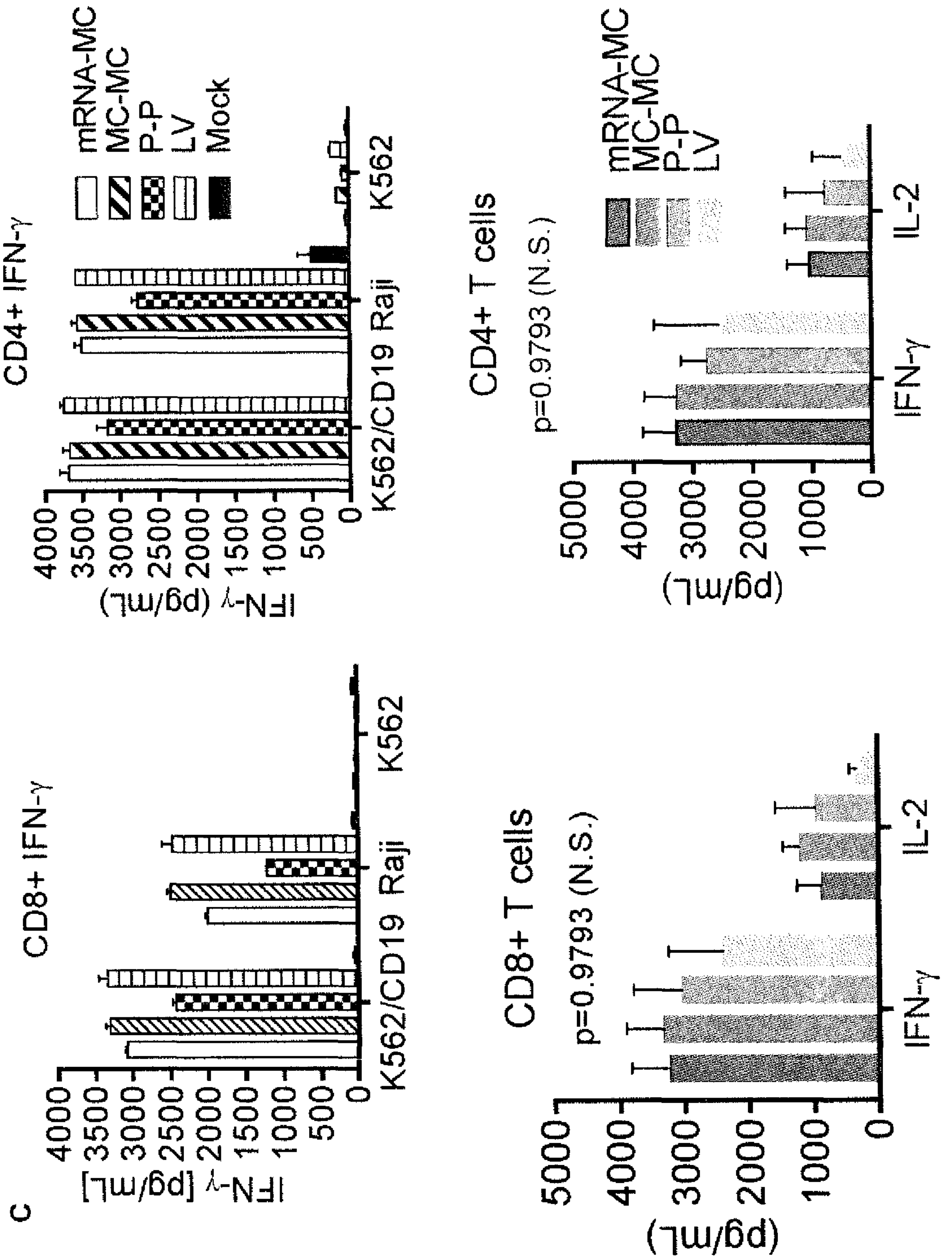
Figure 4:
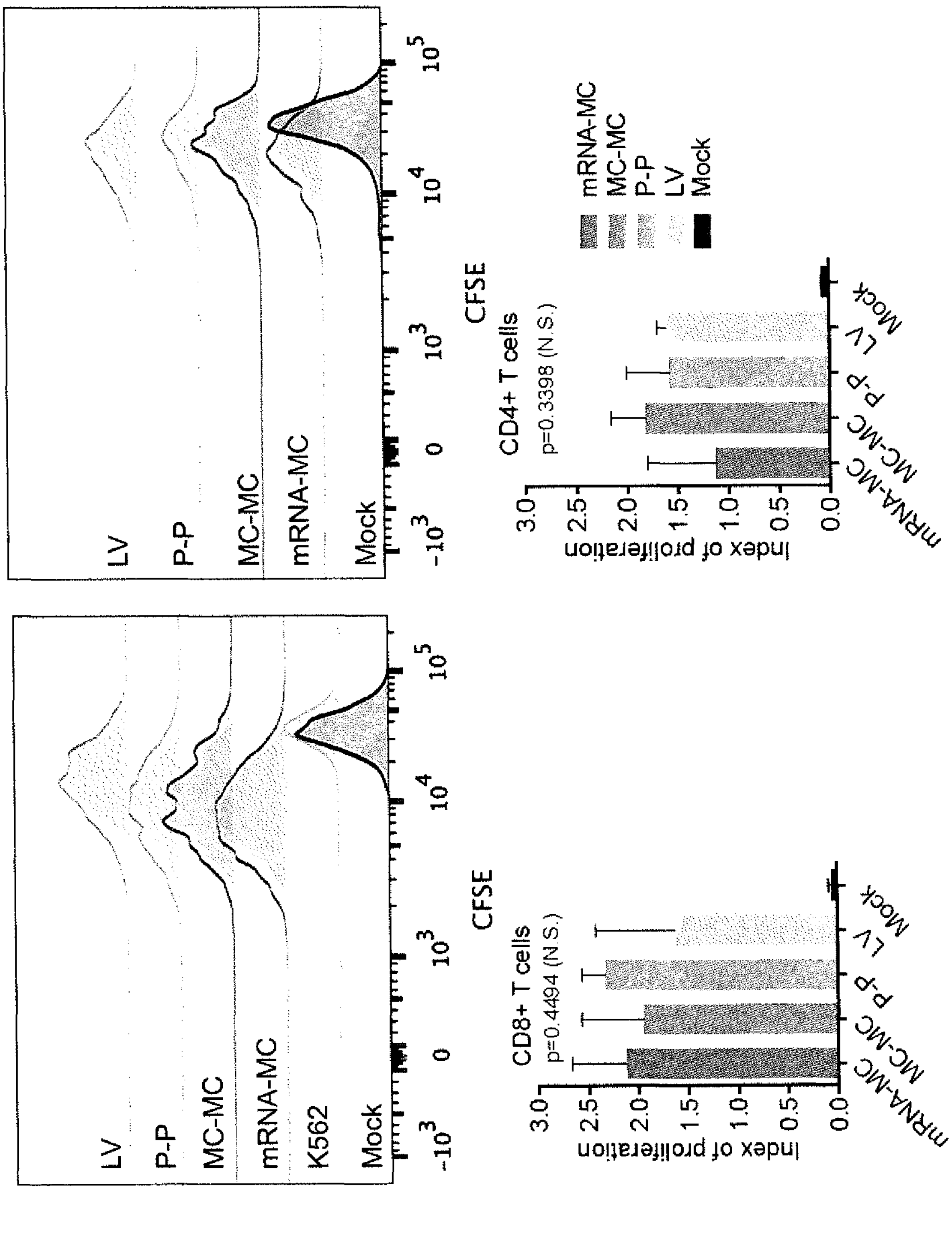
Figure 4:
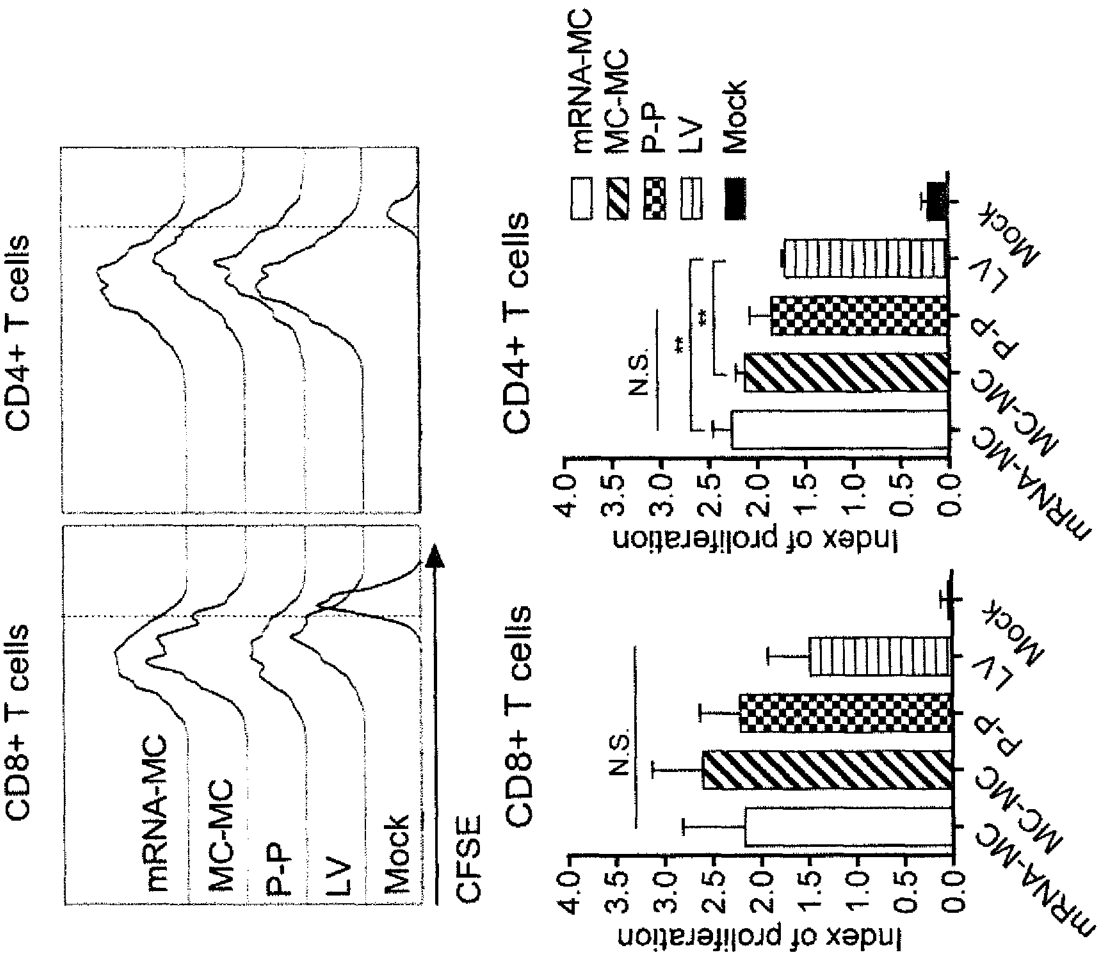

FIG. 4. Comparison of in vitro effector function of CD19 CAR expressing T cells produced with lentiviral transduction or transposon systems (A) A representative flow cytometry dot plot of tEGFR expression for CD8+ and CD4+ T cells after tEGFR enrichment and specific expansion with feeder cells.

(B) Specific cytotoxicity of CD19 CAR expressing CD8+ T cells generated with lentiviral transduction (LV) or transposon systems (P-P, MC-MC or mRNA-MC) against CD19+ expressing and control tumor cell lines. Lysis percentage values are normalized to that of the mock control T cell line. Cytotoxicity data against K562/CD19 from three independent experiments (E:T=10:1) were normalized (cytolytic activity by mock cells) and analyzed by One-way ANOVA.

(C) Cytokine release assay of supernatants obtained 24 hours after co-culture with CD19+ expressing tumor cell lines. Data represents the mean values±SD IFN-γ or IL-2 production of CD8+ and CD4+ T cells from three independent experiments and were analyzed by One-way ANOVA.

(D) Proliferation of CD19 CART cells 72 hours after stimulation with CD19 expressing target cell lines and without addition of exogenous cytokines was assessed by CFSE dye dilution. For analysis, triplicate wells were pooled and the proliferation of live (7AAD$^-$, CD8+ or CD4+ T cells analyzed. The index of cell division was calculated for three independent experiments and the data were analyzed by One-way ANOVA.

(E) Replicate of the experiment shown in FIG. 4D: Proliferation of CD19-CAR T cells within 72 hours after stimulation with K562/CD19+ target cells assessed by CFSE dye dilution. No exogenous cytokines were added to the assay medium. For analysis, triplicate wells were pooled and the proliferation of live (7AAD−) T cells analyzed. The index of cell proliferation (i.e. average number of cell divisions) was calculated from data obtained in n=3 independent experiments using FlowJo software, and data analyzed by one-way ANOVA (**p<0.001).

Figure 5:
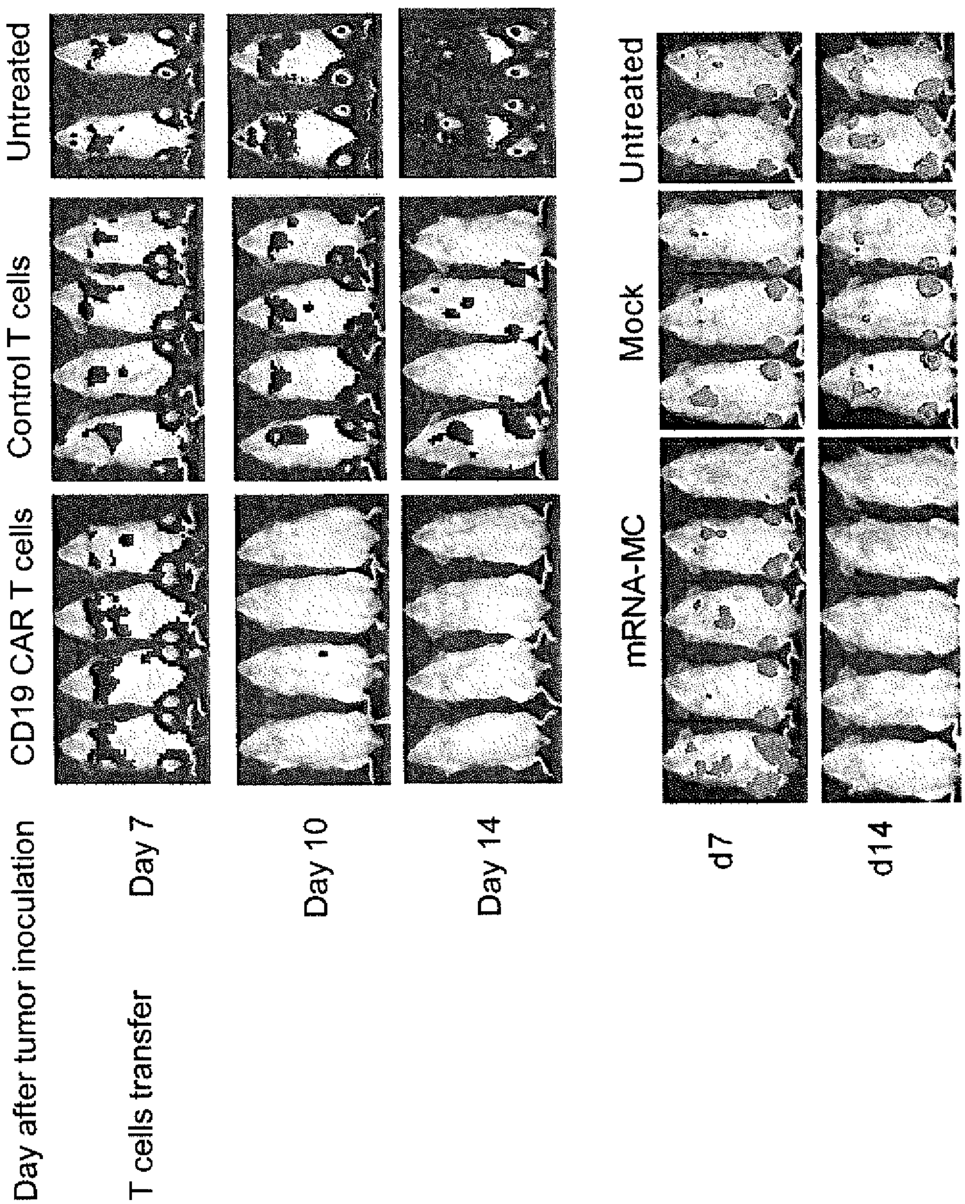
Figure 5:
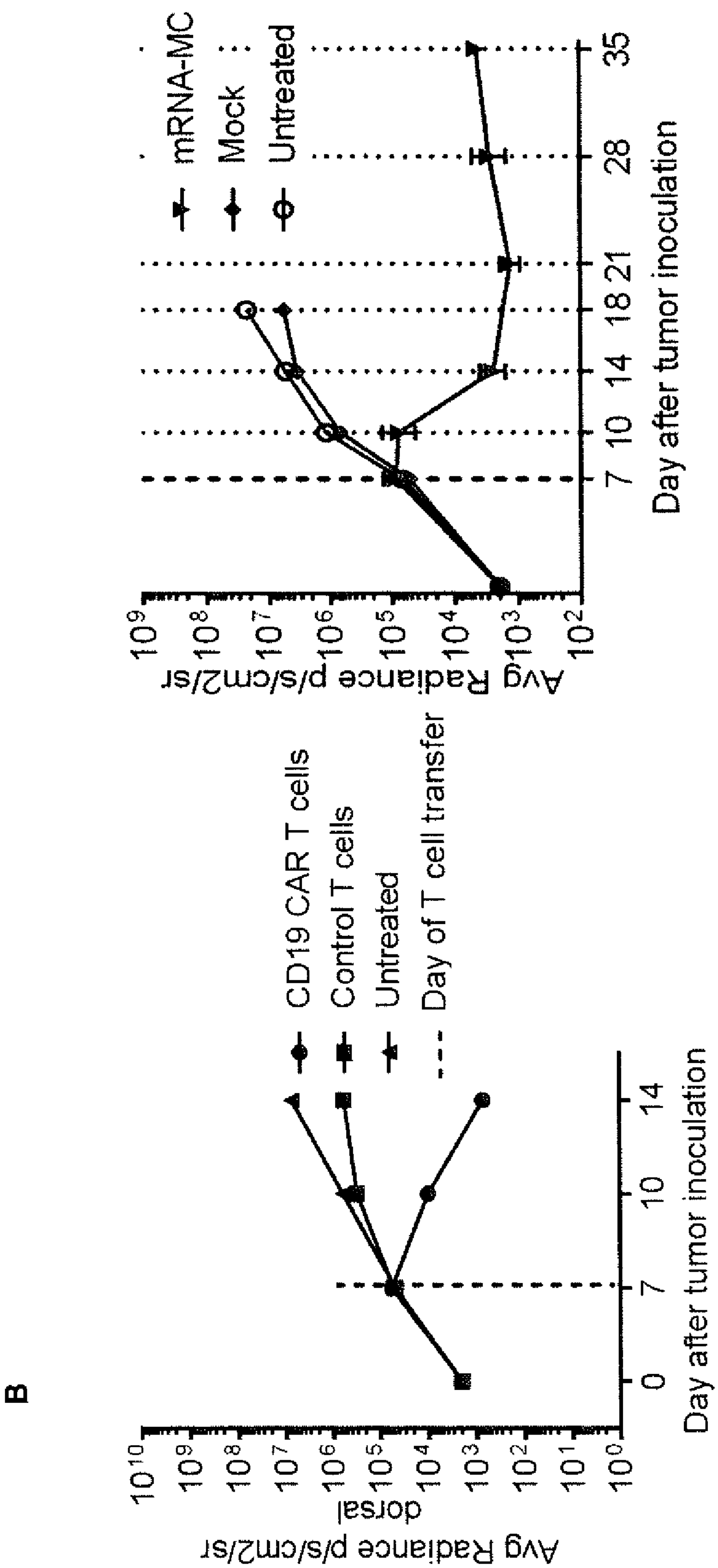
Figure 5:
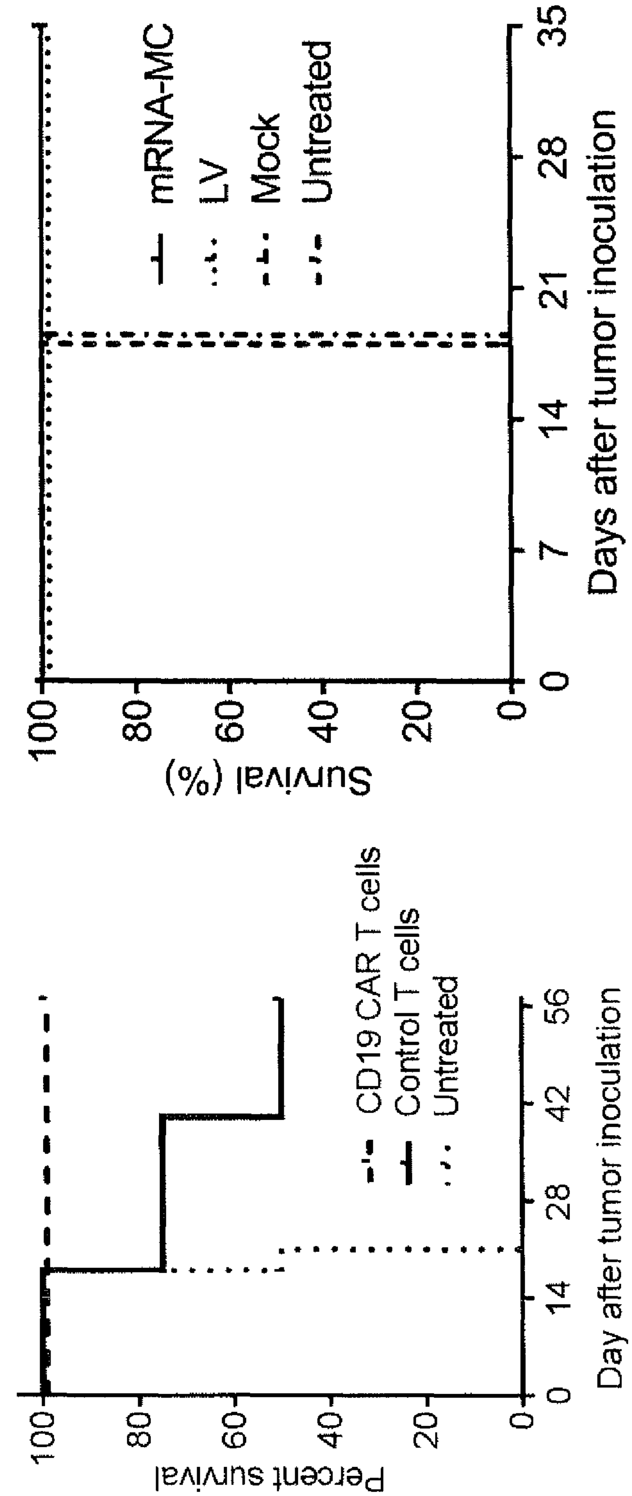
Figure 5:
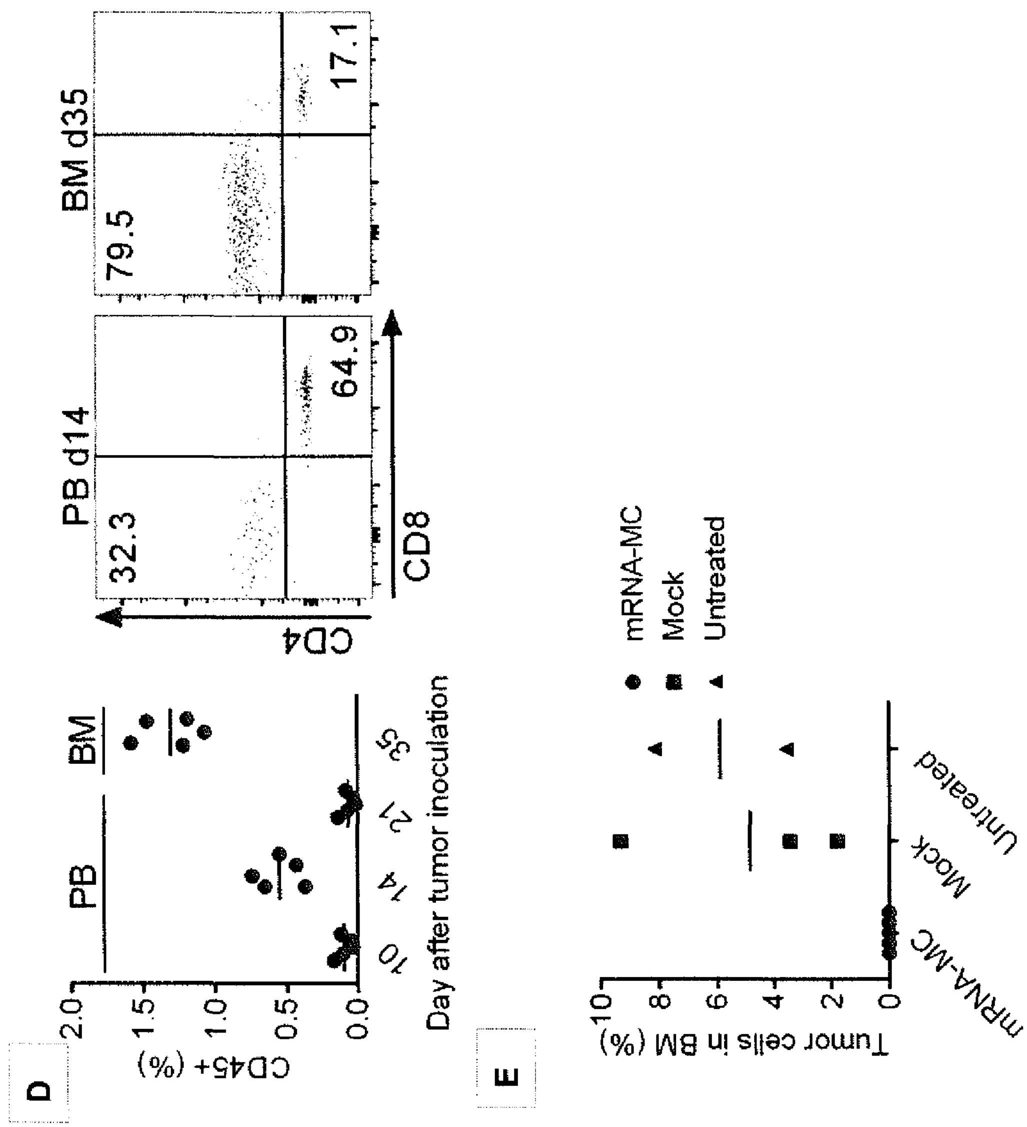

FIG. 5. In vivo tumor reactivity of CD19 CAR T cells modified through transposition with SB100X mRNA and MC-CD19 CAR (A) Upper panel: NSG mice were inoculated with Raji-ffluc cells and seven days later treated with $10\times10^6$ of CD19 CAR T cells (CD8+ and CD4+ T cells, $5\times10^6$ each), unmodified control T cells or left untreated. Cohorts of mice were analyzed by bioluminescence imaging. The dashed line marks the day of T cell transfer. Bioluminescence images from day 7 (the day of T cell transfer) day 10 (3 days after T cell transfer) and day 14 (7 days after T cell transfer) are shown. Lower panel: NSG mice were inoculated with Raji-ffluc/eGFP cells and 7 days later treated with $5\times10^6$ CD19-CAR T cells (1:1 ratio of CD8+ and CD4+ T cells, $2.5\times10^6$ each), unmodified control T cells or left untreated. CD19-CAR T cells were generated by transfection with SB100X mRNA and CD19-CAR MC (4:1 ratio). Bioluminescence images were obtained on day 7 (before T cell infusion, upper row) and on day 14 (7 days after T cell infusion, lower row). Data are representative for results obtained in at least 2 independent experiments with T cells prepared from different donors.

(B) Left panel: Mean values of bioluminescence signals obtained from regions of interest encompassing the entire body of each mouse are plotted for each treatment group at each time point. The data were obtained from the mice shown in the upper panel of FIG. 5A. Right-hand panel: Mean values of bioluminescence signals obtained from regions of interest encompassing the entire body of each mouse are plotted for each treatment group at each time point. The data were obtained from the mice shown in the lower panel of FIG. 5A. The bold dashed line marks the day of T cell infusion. Data are representative for results obtained in at least 2 independent experiments with T cells prepared from different donors.

(C) Left panel: Kaplan-Meier analyses of survival of mice treated with T cells expressing CD19 CAR compared to mice that had received control T cells or no T cells (untreated). Right-hand panel: Kaplan-Meier analysis of survival in groups of mice treated with CD19-CAR T cells that had been prepared by SB transposition (SB100X mRNA and CD19-CAR MC) (n=5) and LV transduction (n=5), control T cells (n=3), or that had received no treatment (n=2). Data are representative for results obtained in at least 2 independent experiments with T cells prepared from different donors.

(D) Frequency of human T cells in the peripheral blood and bone marrow of mice treated with CD19-CAR T cells. Blood samples were obtained 3, 7 and 14 days after T cell transfer (i.e. day 10, 14, 21 after tumor inoculation), and bone marrow harvest upon termination of the experiment. Representative flow cytometry dot plots show $CD8^+$ and $CD4^+$ T cells (gated on live 7-$AAD^-$ $CD45^+$ cells). Data are representative for results obtained in at least 2 independent experiments with T cells prepared from different donors.

(E) Frequency of $CD45^+$ ffLuc/$eGFP^+$ Raji cells in the bone marrow of NSG mice obtained on day 18 (control/untreated mice) and day 35 (CD19-CAR group) of the experiment. Horizontal bars indicate mean values. Data are representative for results obtained in at least 2 independent experiments with T cells prepared from different donors.

Figure 6:
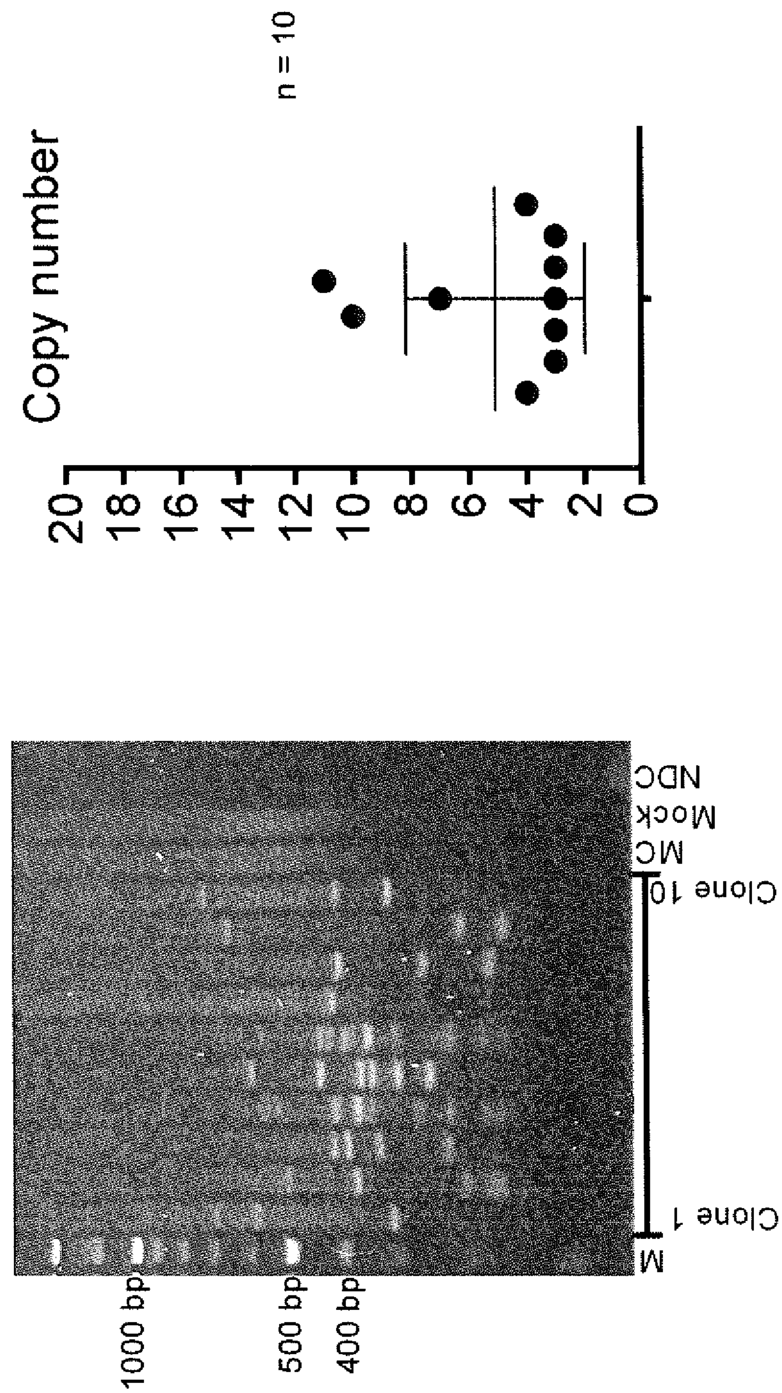
Figure 6:
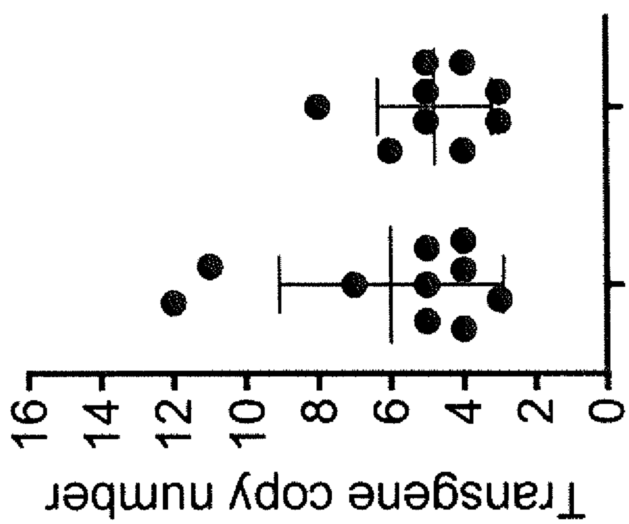

FIG. 6. Determination of transgene copy number of T cells modified with SB100X mRNA and MC-CD19 CAR using splinkerette PCR (spPCR).

(A) A representative agarose gel loaded with 3 μl of PCR product for each of the spPCR reactions. Genomic DNA of CAR+ T cell clones obtained through limiting dilution cloning was amplified with specific primers for transposon left inverted terminal repeats using spPCR as previously described. Lane M: 100 bp DNA ladder (NEB); Clone 1-10: Input genomic DNA from 10 CAR T cell clones; MC: input genomic DNA from samples transfected with MC-CD19 CAR alone, without the SB100X mRNA; Mock: input genomic DNA from nucleofected/untransfected T cells; NDC: no DNA control.

(B) Summarized data from n=10 different CD8+ CAR T cell clones, genetically modified through SB100X transposition with SB100X mRNA and MC-CD19 CAR (4:1 ratio). Shown is the mean copy number per T cells with SD.

(C) Gene copy number of $CD4^+$ (n=10) and $CD8^+$ (n=9) CD19-CAR T cell clones, modified with SB100X mRNA and MC CD19-CAR (4:1 ratio). The experiment shown for $CD8^+$ CD19-CAR T cell clones is a replicate of the experiment shown in (B).

Figure 7:
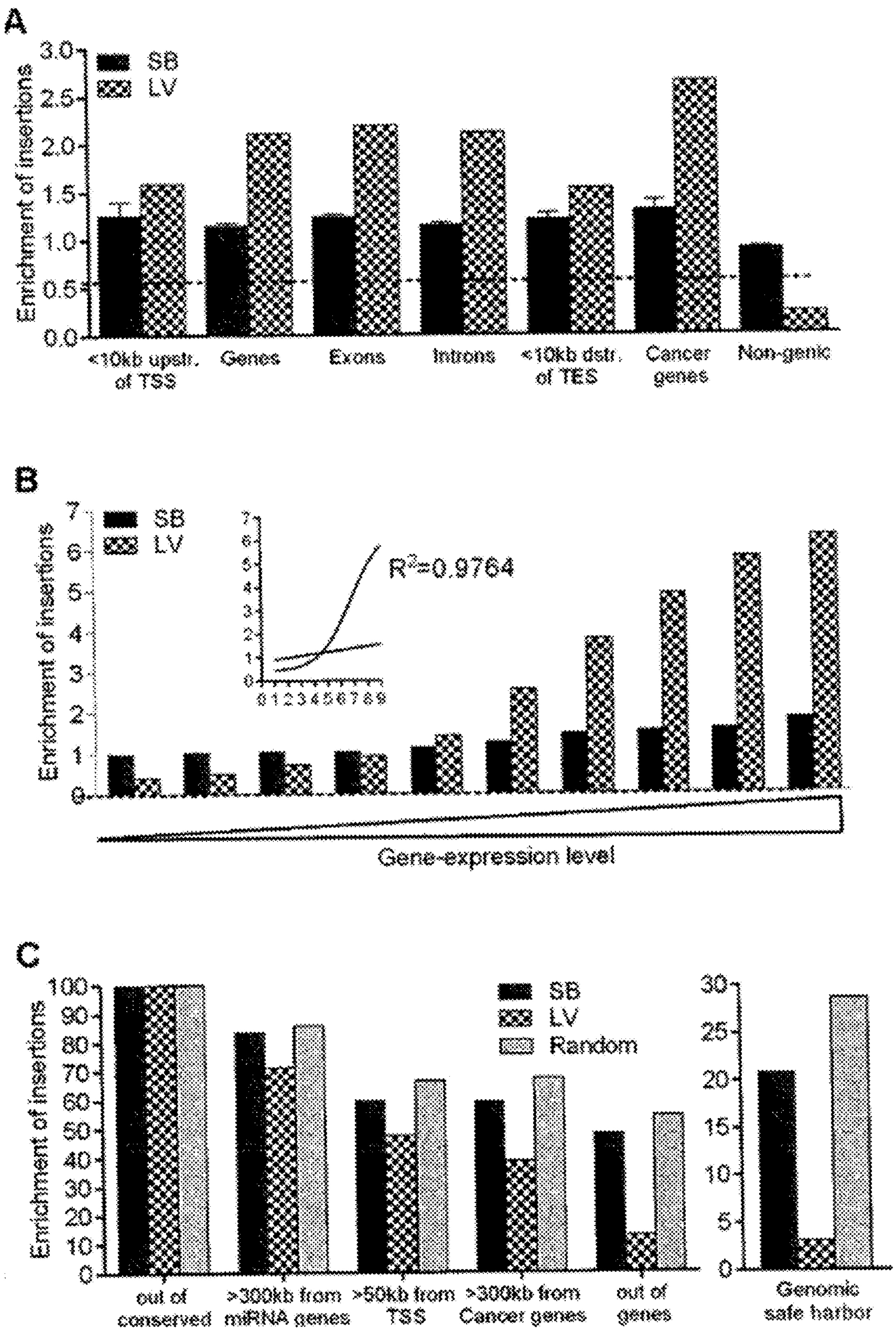

FIG. 7. Insertion site properties and safety assessment of SB and LV in human T cells.

(A) Comparison of LV and SB insertion frequencies in gene-associated features of the human genome. Fold-enrichment of SB and LV insertion sites over the random expected frequency are plotted. The dashed line stands for fold enrichment of 1 over the insertion frequency expected by random chance in the categories on the x-axis. TSS and TES: transcriptional start and end sites, respectively.

(B) Correlation between genomic insertion site frequencies and transcriptional status of the genes. Genes of activated T cells were clustered into 10 groups of equal size based on their growing expressional levels (from left to right). The dashed line marks the expected random insertion frequencies normalized to 1. The trend line for SB (black) was fitted using linear settings. Exponential setting was used to fit the trend line for the first 9 data points of LV dataset (R-squared value shown). The increase of insertion frequencies in the group of most active genes does not follow the exponential trend.

(C) Integration frequencies of SB and LV in genomic safe harbors of T cells. Genomic safe harbors are regions of the human chromosomes that concurrently meet the following 5 criteria of the x-axis: not ultraconserved, more than 300 kb away from miRNA genes, more than 50 kb away from transcriptional start sites (TSS), more than 300 kb away from genes involved in cancer and outside transcription units. Left diagram shows the percentage of SB, LV and random insertions fulfilling each criterion. Right diagram shows percentage of insertions fulfilling all 5 criteria.

Figure 8:
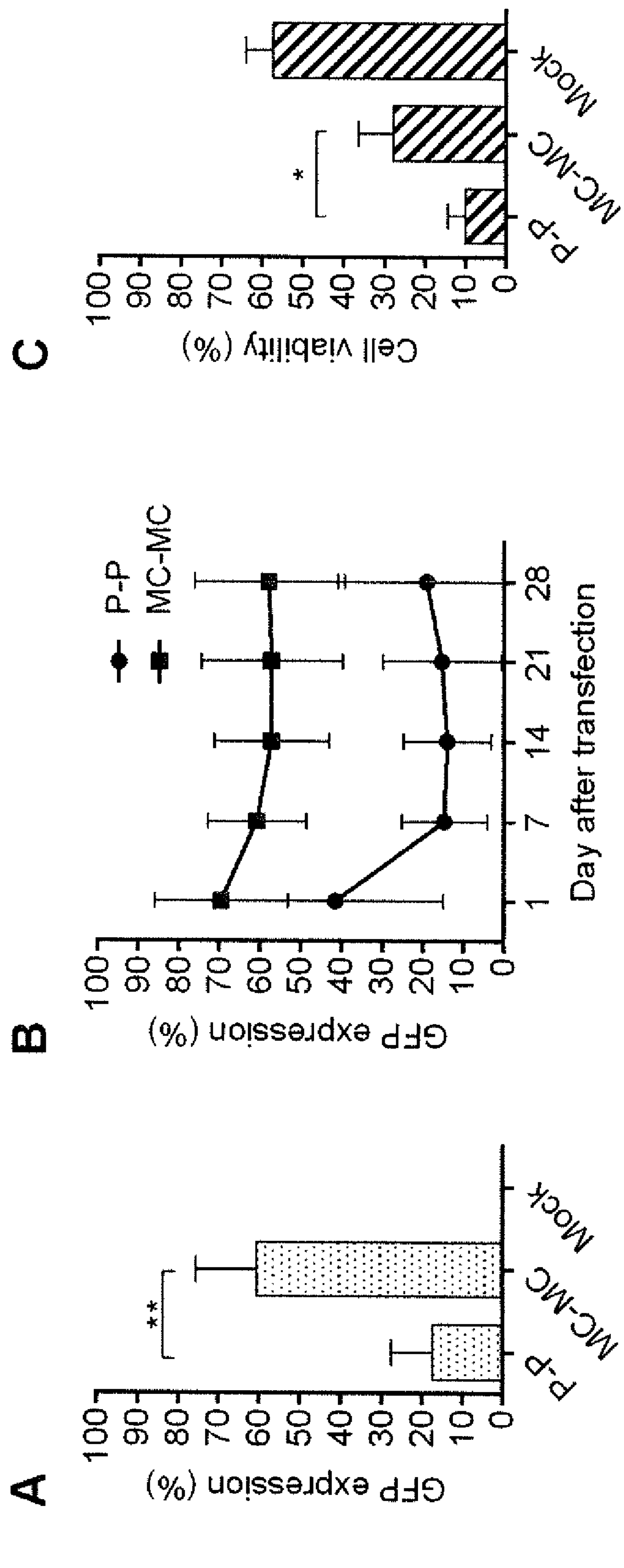

FIG. 8. Transposition of eGFP using MC and plasmid-encoded SB transposase and transposon.

(A) $CD8^+$ T cells were transfected with 1 μg each of conventional plasmids encoding eGFP and SB100X (P-P) or corresponding equimolar amounts of MCs (MC-MC). eGFP expression was assessed by flow cytometry. Data represent mean values±SD of three independent experiments, $p<0.001$.

(B) Stability of eGFP expression was assessed by flow cytometry out to day 28 after transfection. Mean values±SD for data obtained in three independent experiments are shown.

(C) Viability of T cells 48 hours post-transfection was assessed by 7-AAD staining and flow cytometric analysis. Data represent mean values±SD of three independent experiments. Statistical analysis was performed using Student's t test, $p<0.05$.

Figure 9:
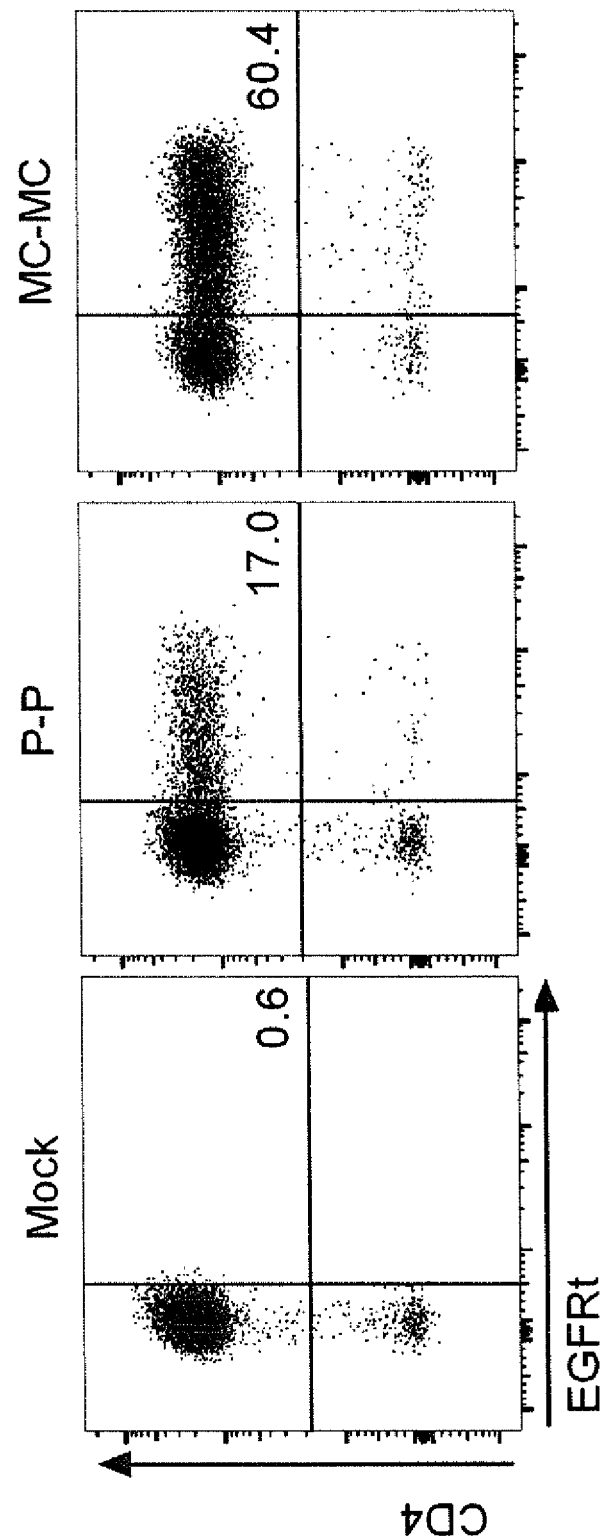

FIG. 9. MC SB transposition in $CD4^+$ T cells.

$CD4^+$ T cells were transfected with 1 μg each of conventional plasmids encoding a CD19-CAR transposon and SB100X transposase (P-P) or corresponding MCs (MC-MC, using equimolar amounts of DNA) (n=3). A representative flow cytometry dot plot of EGFRt expression on day 14 is shown (gated on live, i.e. 7-AAD-negative cells).

Figure 10:
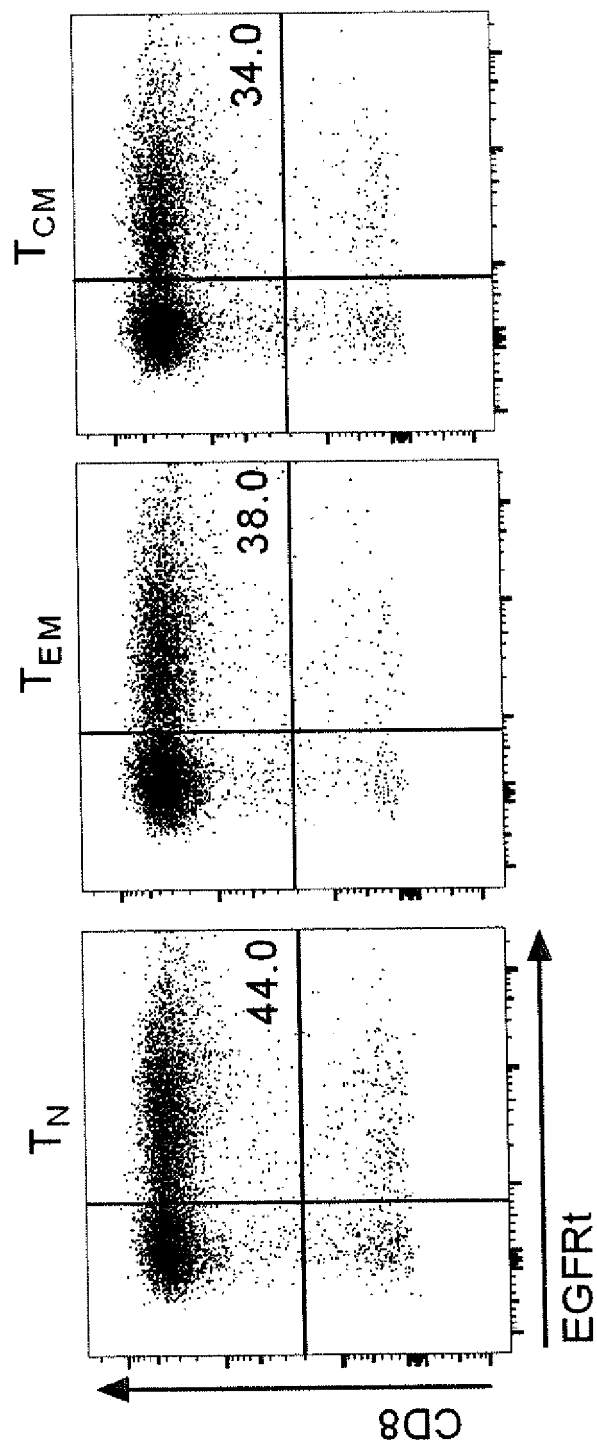

FIG. 10. MC SB transposition in $CD8^+$ naïve and memory T cell subsets.

$CD8^+$ naïve ($CD45RA^+RO^-62L^+$, $T_N$), central memory ($CD45RA^-RO^+62L^+$, $T_{CM}$) and effector memory ($CD45RA^-RO^+62L^+$, $T_{EM}$) T cells were purified and transfected with SB100X mRNA and CD19-CAR MC. Flow cytometry dot plots show EGFRt expression on day 14 after transfection (gating on live, i.e. 7-AAD-negative cells).

Figure 11:
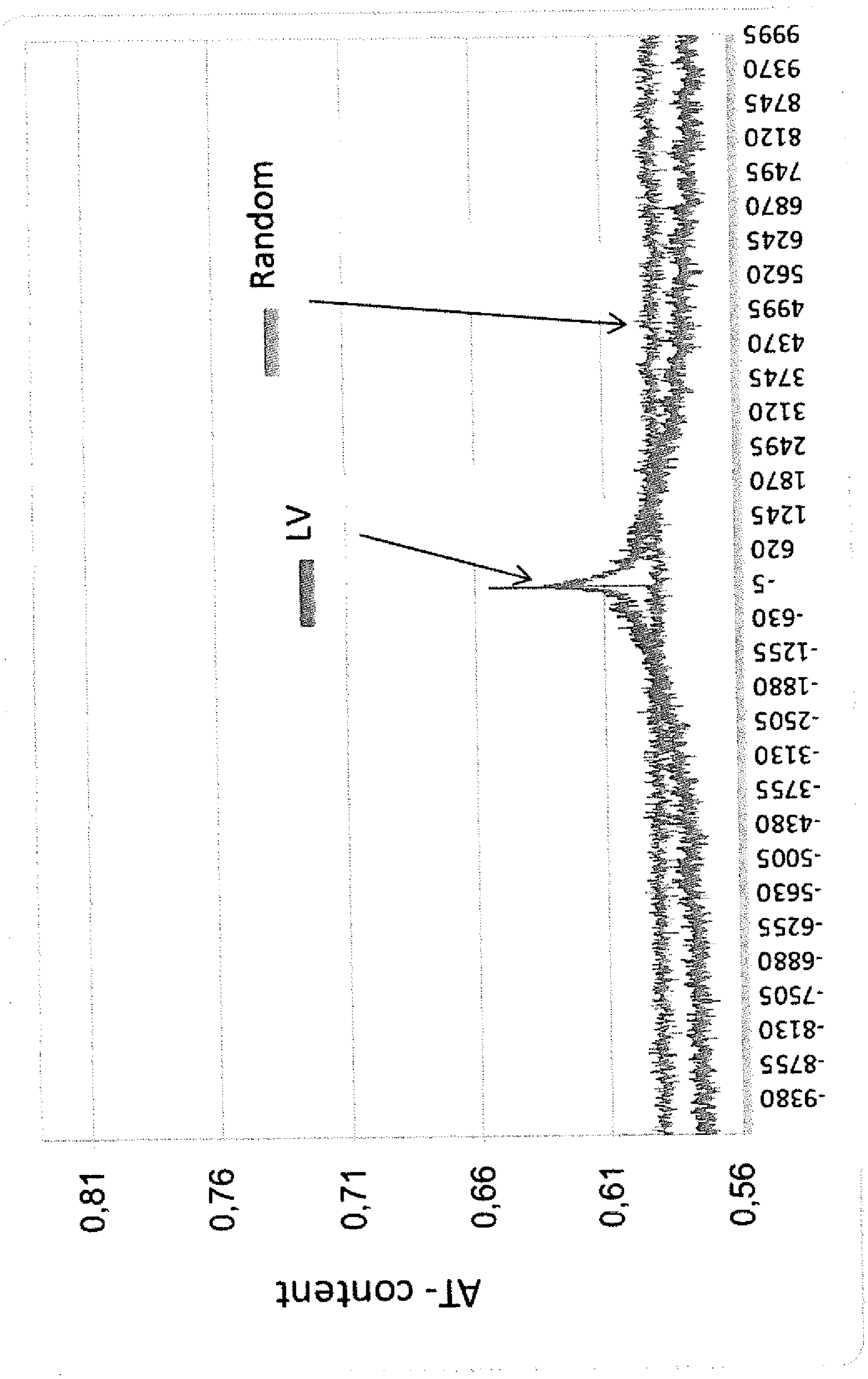
Figure 11:
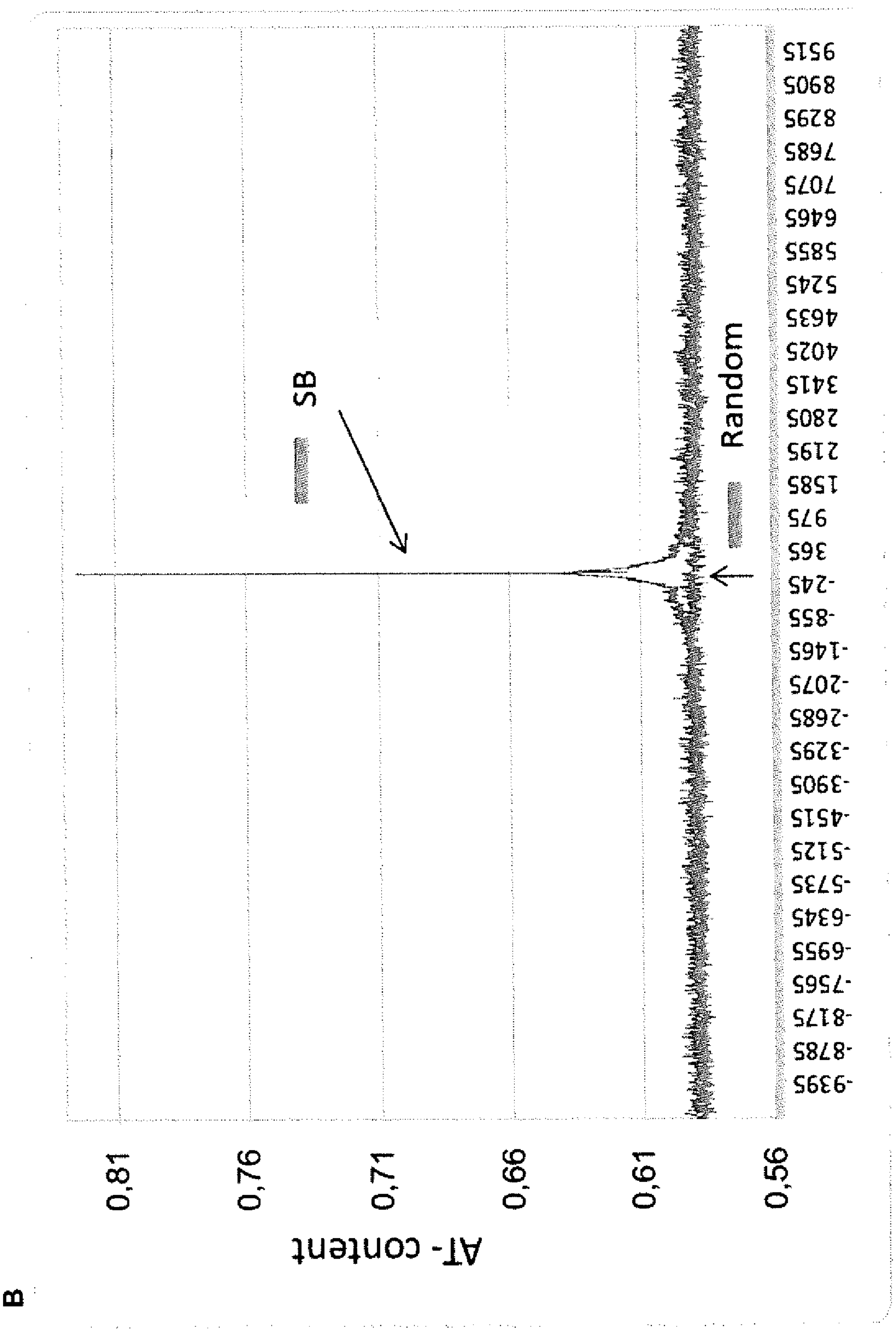
Figure 11:
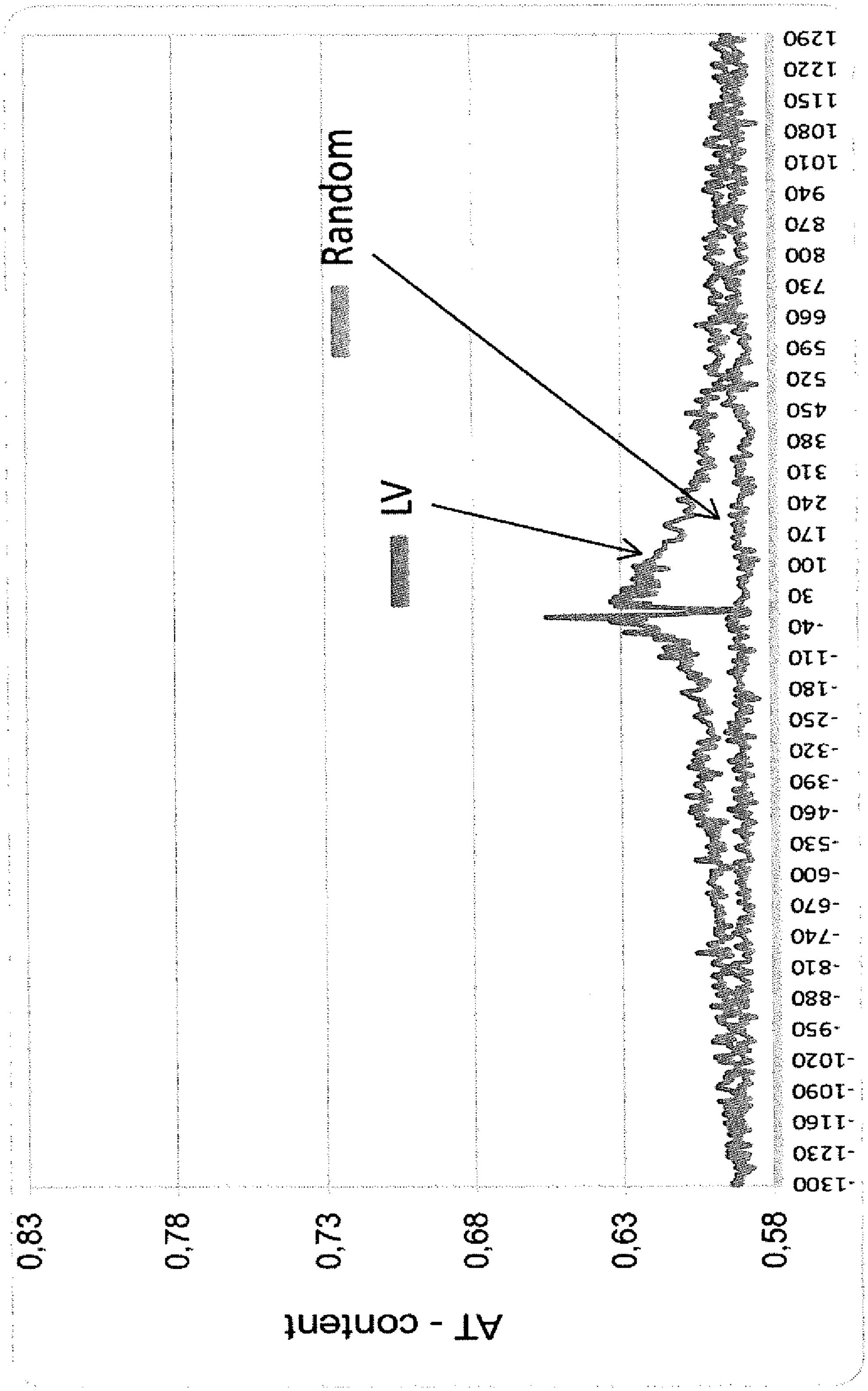
Figure 11:
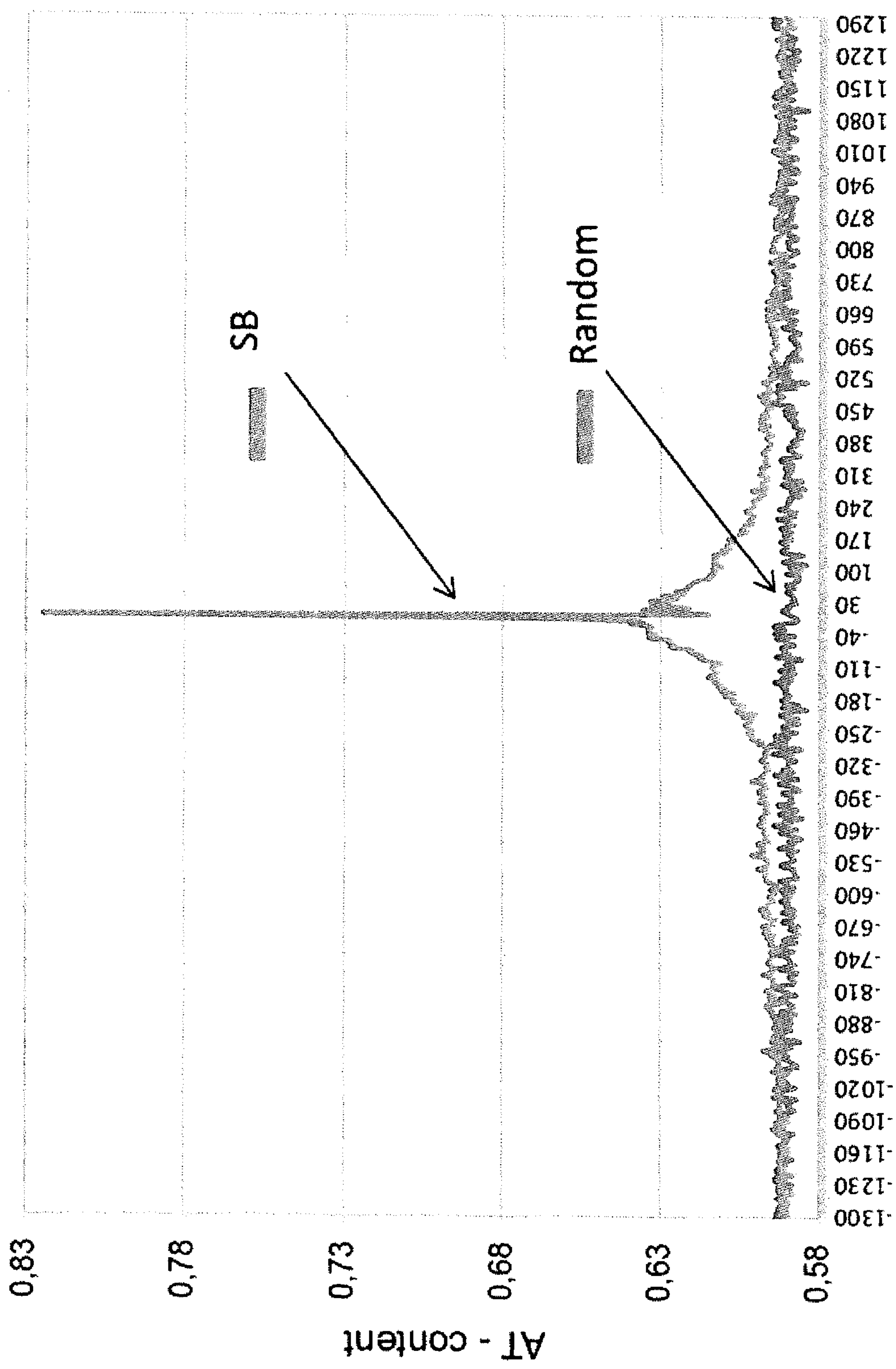

FIG. 11. Nucleotide composition of chromosomal DNA around SB and LV insertion sites in T cells.

Each data point represents the average TA-content of 5 nucleotide bins in the chromosomal DNA around SB and LV insertions sites in T cells. Depicted are analysis windows of 20 kbp (A, B) and 2.6 kbp (C, D). The random dataset depicts the TA content around 10.000 computationally generated arbitrary loci of the human chromosomes.

FIG. 12. Base composition of SB target sites on human T cell chromosomes.

The 58 nucleotide long nucleotide frequency matrix was represented in a table, with "V"-numbers indicating consecutive nucleotides. The triangle marks the insertion site. The table indicates the relative frequency (percentage) of the four nucleotides A, C, G and T for each nucleotide.

Figure 13:
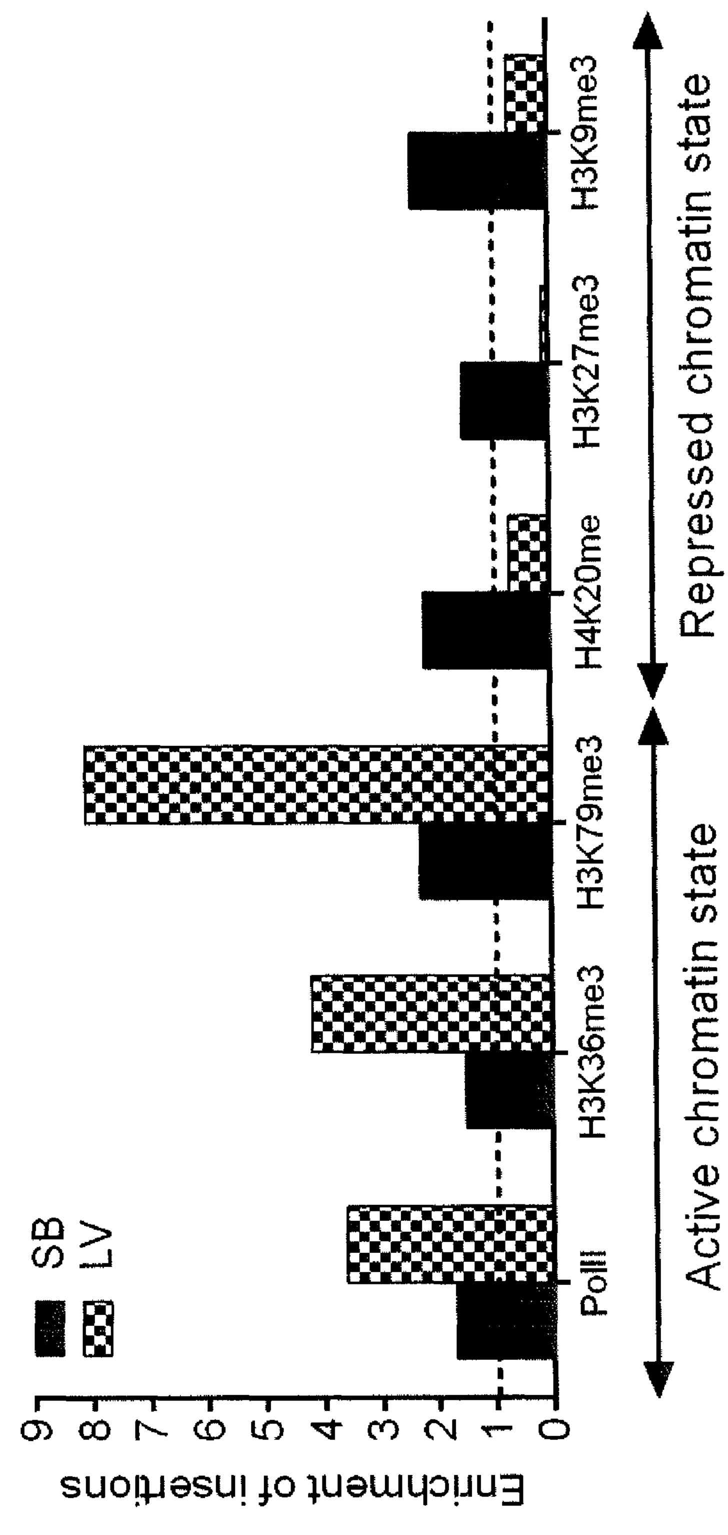

FIG. 13. Representation of SB and LV insertion sites in transcriptionally active and repressed chromatin of T cells.

Chromosomal regions covered by RNA polymerase II (PolII), or possessing specific histone modifications (listed on the x-axis) were determined from available datasets obtained on activated human T cells. Fold changes in the representation of integration sites in the ChIP-Seq peaks compared to random control (dashed line) are shown on the y-axis.

Figure 14:
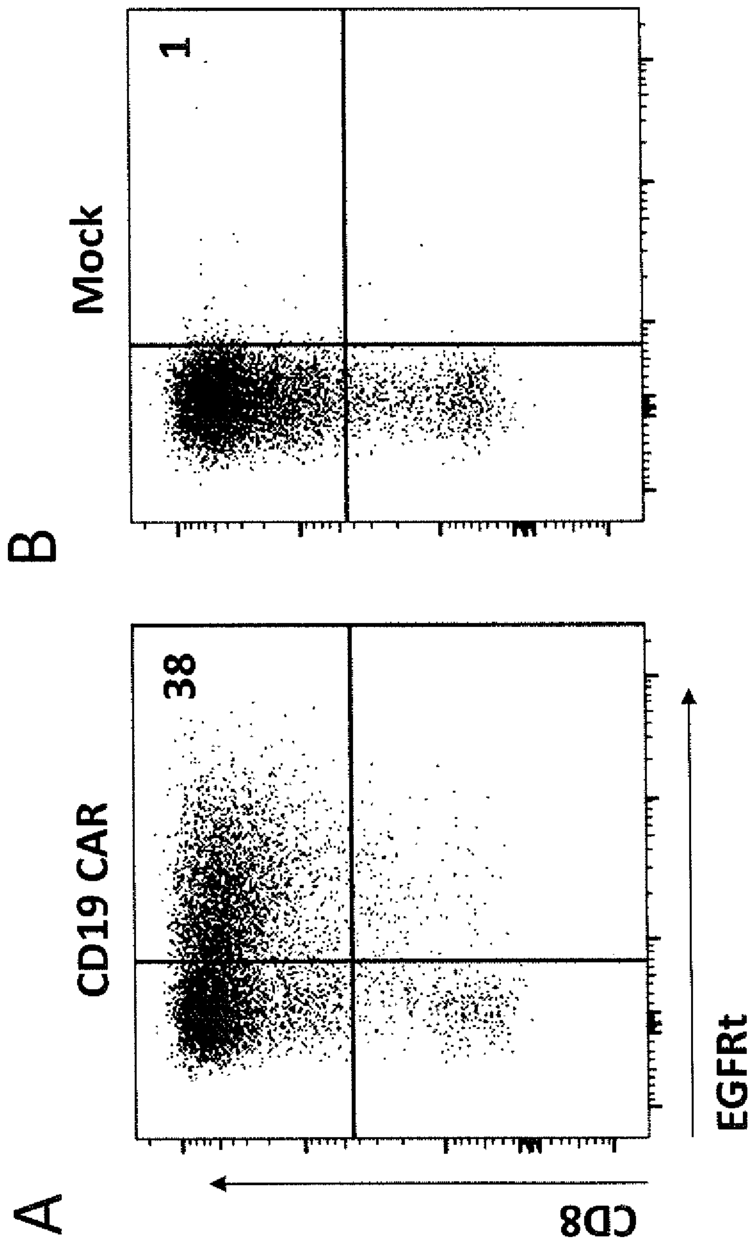

FIG. 14. Flow cytometric analysis of EGFRt expression on day 14 post transfection. Gene-transfer was performed into (A) non-activated T cells that received SB100X mRNA and CD19-CAR MC or (B) non-activated mock-transfected T cells.

Figure 15:
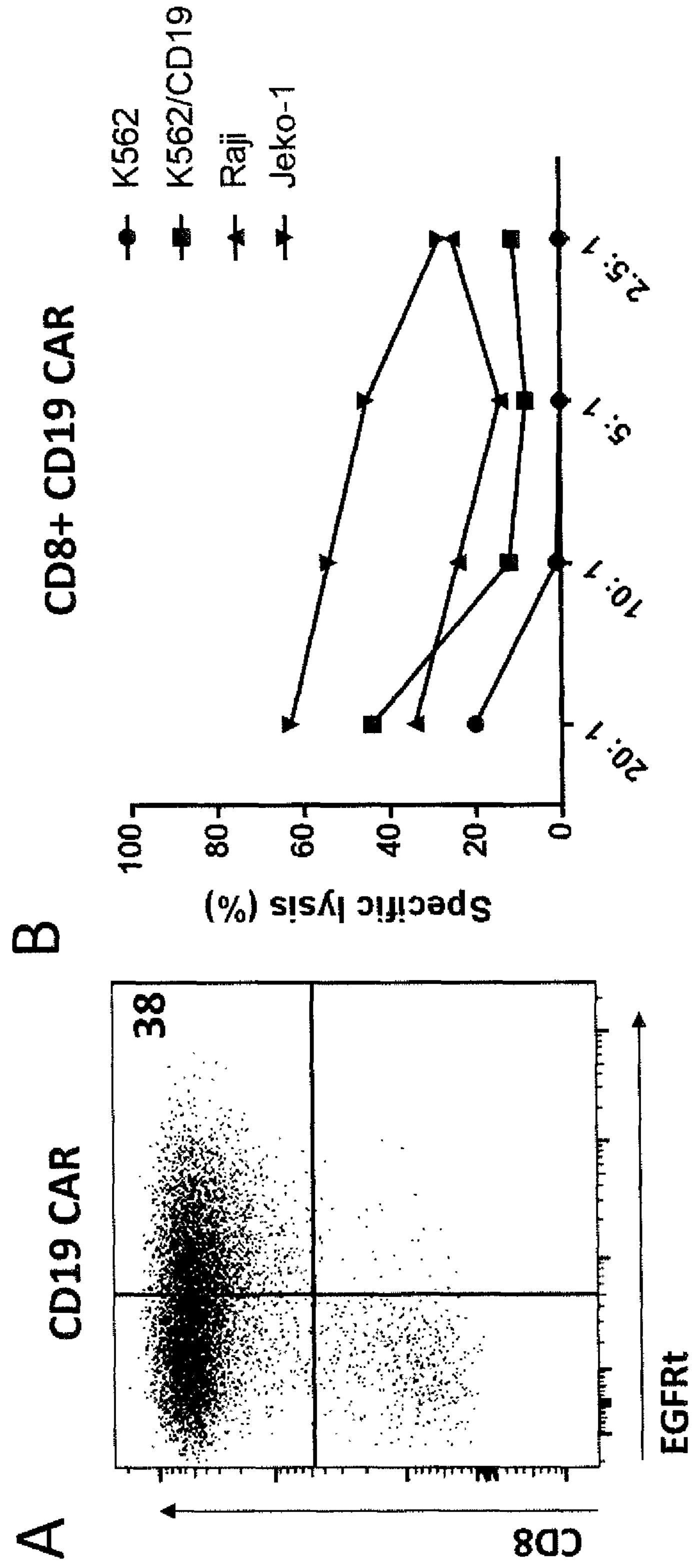

FIG. 15. Flow cytometric analysis of EGFRt expression on day 14 post transfection. (A) Gene-transfer was performed into non-activated T cells that received SB100X mRNA and CD19-CAR MC and were expanded using $CD19^+$ EBV-LCL. (B) Cytolytic activity against $CD19^+$ target cells was analyzed in a standard 4-hour cytotoxicity assay.

Figure 16:
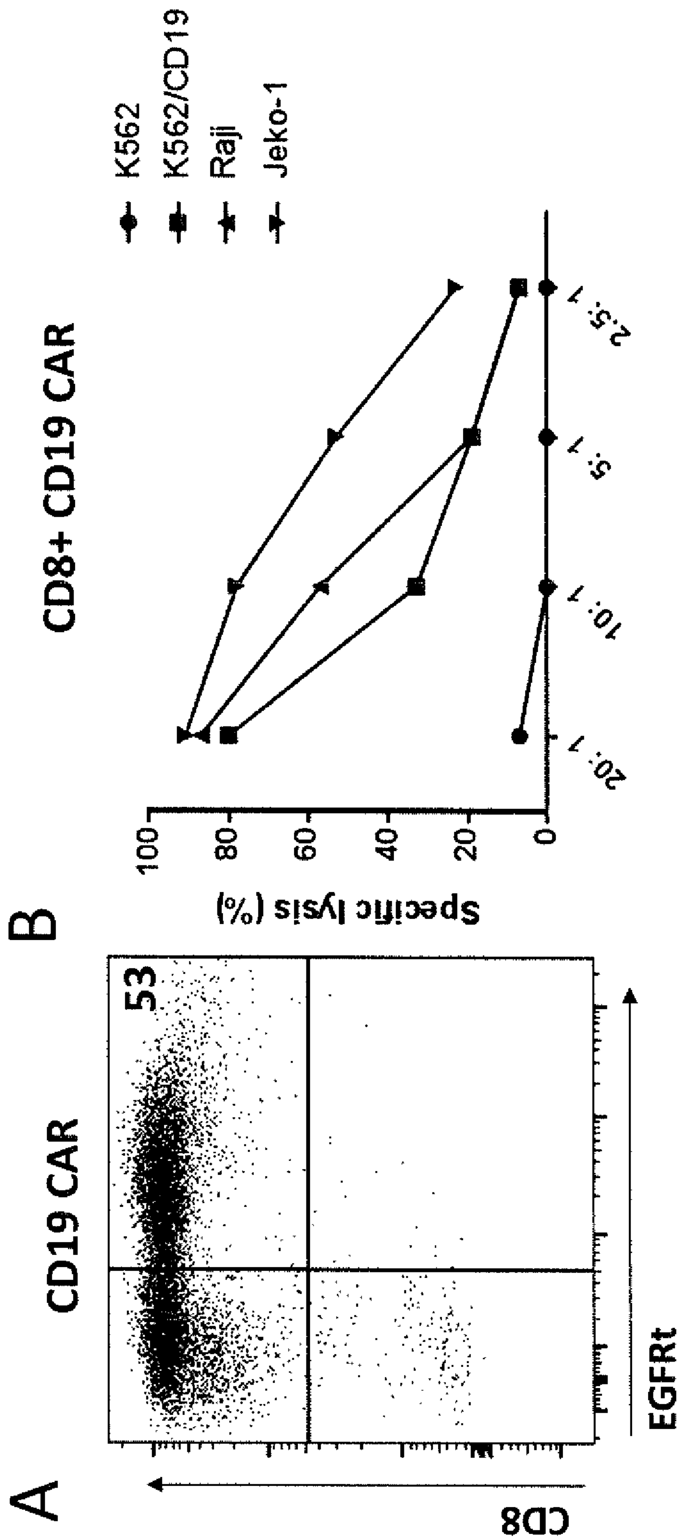

FIG. 16. Flow cytometric analysis of EGFRt expression on day 14 post transfection. (A) Gene-transfer was performed into non-activated T cells that received SB100X mRNA and CD19-CAR MC and after transfection were maintained in T-cell medium without antigen-dependent expansion. (B) Cytolytic activity against $CD19^+$ target cells was analyzed in a standard 4-hour cytotoxicity assay.

Figure 17:
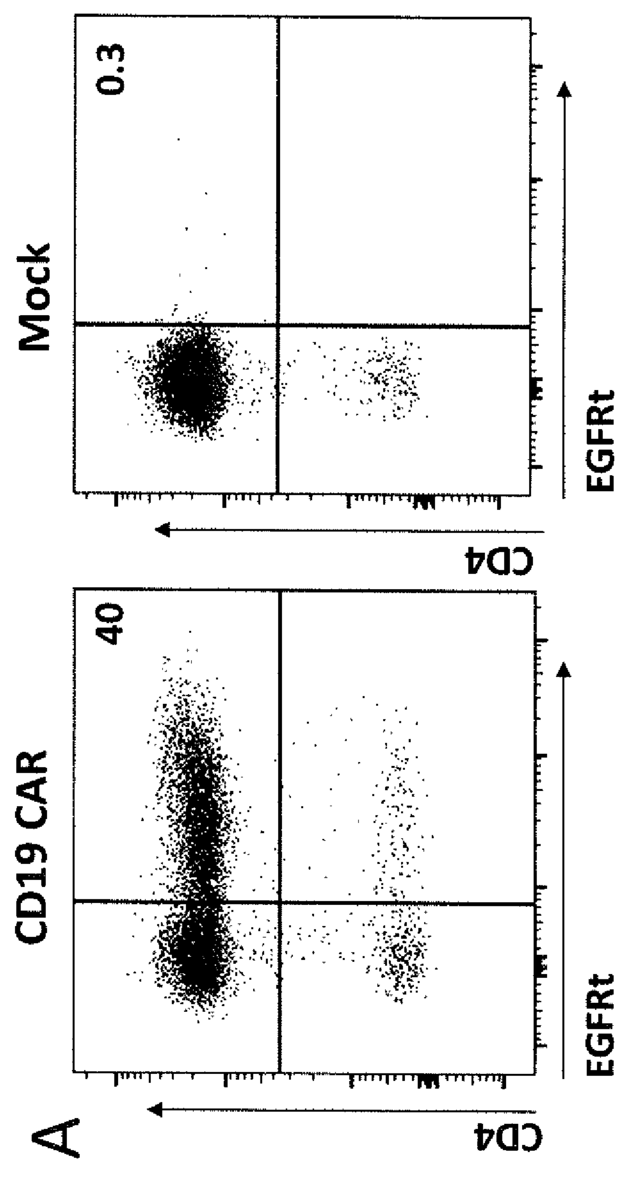

FIG. 17. Flow cytometric analysis of EGFRt expression on day 14 post transfection. Gene-transfer was performed into non-activated (A) $CD4^+$ T cells and (B) non-activated $CD8^+$ T cells that received SB100X MC and CD19-CAR MC (1:1 ratio) (left dot plots) or were mock-transfected (right dot plots). (C) Cytolytic activity of $CD8^+$ CD19 CAR T cells against $CD19^+$ target cells was analyzed in a standard 4-hour cytotoxicity assay.

Figure 18:
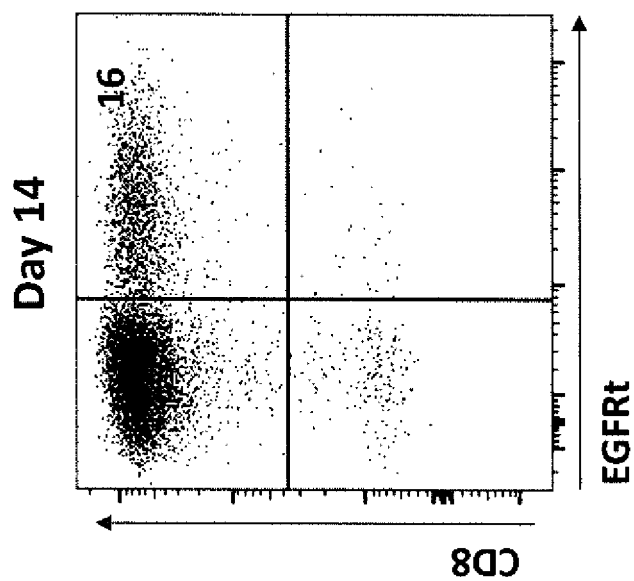

FIG. 18. Flow cytometric analysis of EGFRt expression on day 14 post transfection. Gene-transfer was performed in $CD8^+$ T cells that were electroporated with SB100X MC and CD19-CAR MC (1:1 ratio) using the Agile Pulse MAX System.

Figure 19:
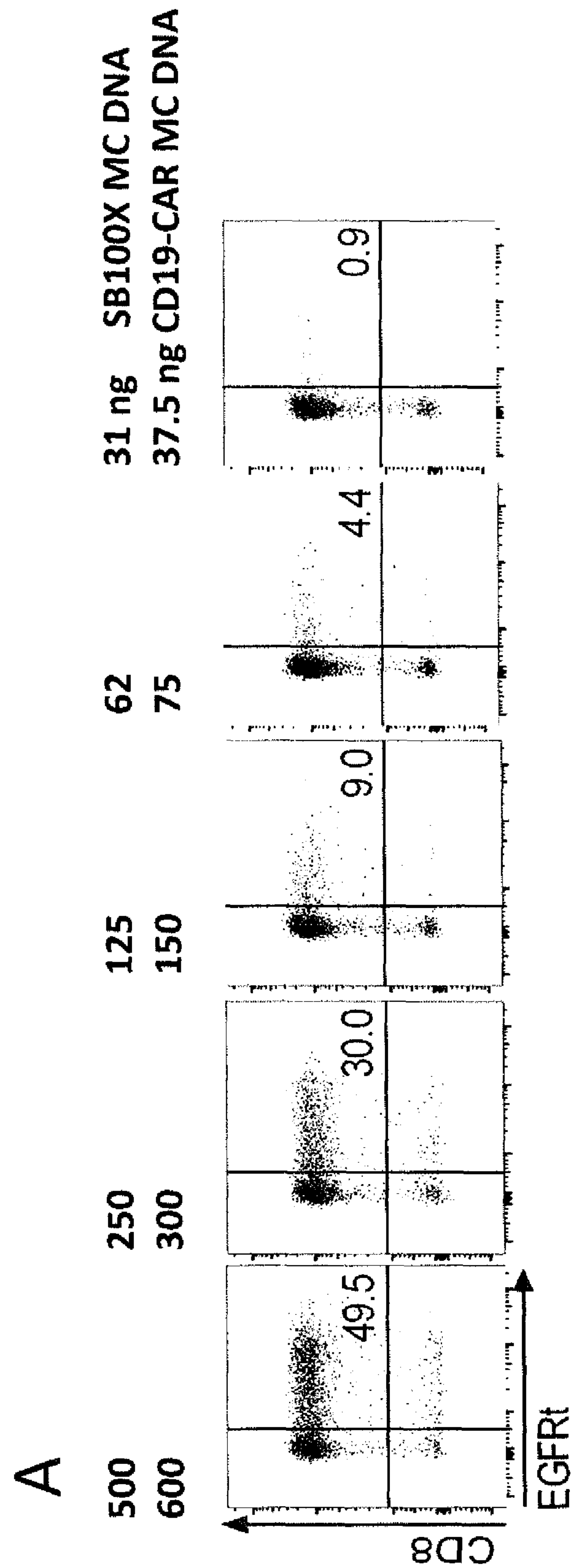

FIG. 19. Titration of SB100X and CD19-CAR MC DNA and correlation with resulting CD19-CAR transposon copy number. (A-B) Flow cytometric analysis of EGFRt expression on day 14 post-transfection, in $CD8^+$ T cells that were transfected with titrated amounts of SB100X-encoding MC and CD19-CAR-encoding MC. (A) Flow cytometry dot plots of one representative experiment. (B) Percentage of $EGFRt^+$ T cells (left diagram) and mean fluorescence intensity after staining for the EGFRt marker (right diagram). Data represent mean values±SD of n=2 independent experiments with T cells from different donors. (C) Polyclonal $EGFRt^+$ $CD8^+$ T cells were FACS-purified and genomic DNA isolated for transposon copy number analysis by droplet digital PCR. Data show the average transposon copy number and represent mean values±SD of n=2 independent experiments with T cells from different donors.

Figure 20:
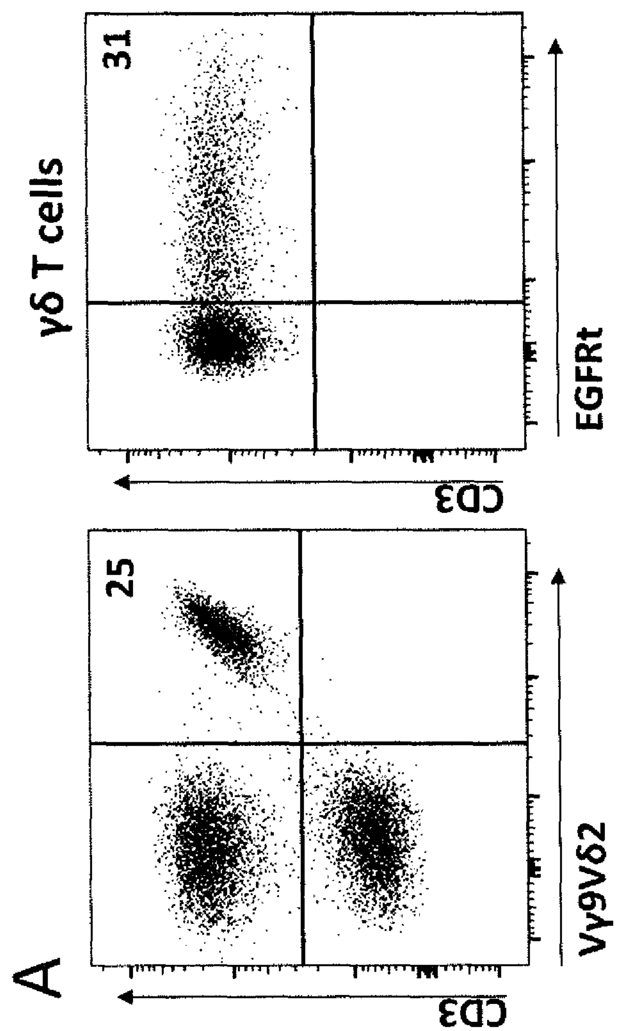

FIG. 20. (A) Flow cytometric analysis of EGFRt expression in Vγ9Vδ2 γδ T cells on day 9 after transfection of SB100X MC and CD19-CAR MC. (B) Flow cytometric analysis of EGFRt expression in Vγ9Vδ2 γδ T cells after stimulation with CD19+ EBV-LCL. (C) Cytolytic activity of CD19-CAR modified and mock-transduced Vγ9Vδ2 γδ T cells against $CD19^+$ target cells was analyzed in a standard 4-hour cytotoxicity assay. (D) Cytokine secretion by CD19-CAR modified and mock-transduced Vγ9Vδ2 γδ T cells after stimulation with $CD19^+$ target cells was analyzed by ELISA in supernatant removed after a 20-hour co-culture.

Figure 21:
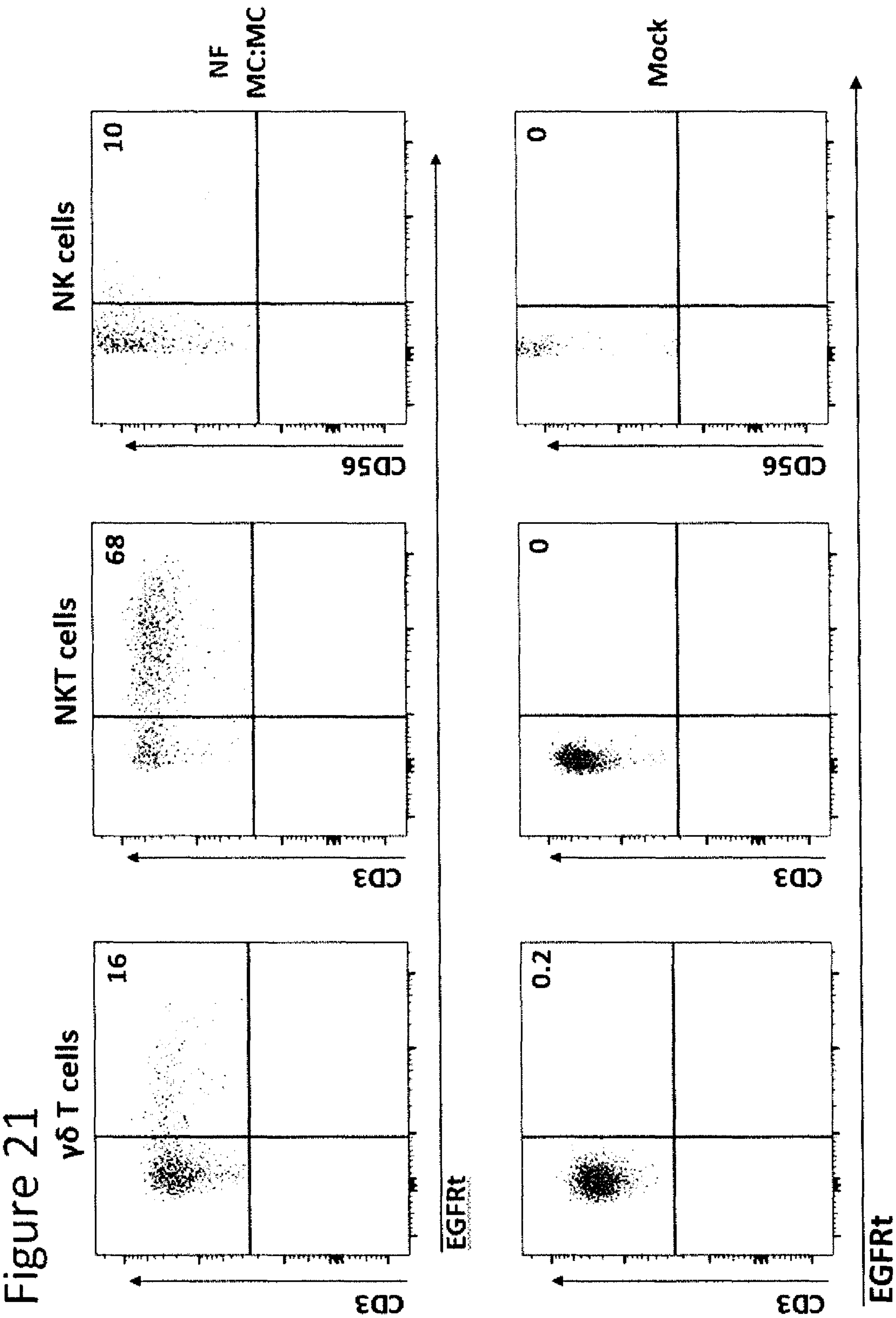

FIG. 21. Flow cytometric analysis of EGFRt expression on day 9 after transfection of SB100X MC and CD19-CAR MC into bulk PBMC. EGFRt expression on Vγ9Vδ2 γδ T cells (CD3+ Vγ9Vδ2+), NKT cells (CD3+, CD56+), and NK cells (CD3−, CD56+).

DETAILED DESCRIPTION OF THE INVENTION

To date, technologies for the transposition and stable integration of transgenes into the genome of mammalian cells using plasmid DNA-encoded transposase and plasmid DNA-encoded transposon (TE) have been disclosed in the prior art. More specifically, technologies for the transposition and stable integration of transgenes encoding tumor-reactive TCRs and CARs into the genome of human T lymphocytes using plasmid DNA-encoded transposase and plasmid DNA-encoded transposon have been disclosed in the prior art.

In human T lymphocytes, the use of plasmid DNA-encoded transposase and plasmid DNA-encoded transposon (TE) (introduced into the T lymphocyte by various methods including electrotransfer) has resulted in very low levels of stable gene transfer (typically <10%) (Huang *Mol Therapy* 2008; Field *PLoS*1 2013), a high level of toxicity associated with the introduction of the genetic material into the T cells, necessitating further selection procedures (mechanical, e.g. beads-based or FACS sorting and/or biological, e.g. antigen-dependent stimulation) and ex vivo expansion (typically several weeks) (Singh *Immunol Rev* 2014) in order to obtain quantities of gene-modified T cells sufficient for their intended therapeutic use. Most notably, however, the use of CAR-modified T lymphocytes in which the gene transfer was performed with plasmid DNA-encoded transposase and plasmid DNA-encoded CAR transposon displayed inferior (compared to CAR T cells gene-modified through lentiviral or retroviral gene transfer) or even lacking therapeutic efficacy in pre-clinical and clinical applications.

In the present invention, the inventors have used for the first time mRNA-encoded transposase (SB100X) in combination with a minicircle DNA-encoded transposon (encoding eGFP or a CD19-specific CAR) to accomplish gene transfer into human T lymphocytes. With this method, the inventors accomplished very high levels of stable TE integration (>50%), long-term stable transgene expression (stable at the same level for at least 4 weeks), at significantly lower toxicity to the T lymphocyte compared to the use of plasmid DNA-encoded transposase (SB100X) and plasmid DNA-encoded transposon (encoding eGFP or a CD19-specific CAR).

Because of the higher gene transfer rate and lower toxicity with the novel approach of the invention, the ex vivo culture time can be significantly reduced to obtain therapeutic numbers, and/or the overall yield of gene-modified T lymphocytes in a given time significantly increased, even enabling their direct therapeutic use without further selection or expansion procedures.

Our invention describes for the first time the use of a minicircle DNA-encoded transposon (TE) in combination with mRNA-encoded transposase to accomplish stable integration of a TE into the genome of a mammalian cell.

More specifically, the present invention describes for the first time the use of a minicircle DNA-encoded transposon (TE) in combination with mRNA-encoded transposase to accomplish stable integration of a TE into the genome of a lymphocyte.

Further, the present invention describes for the first time the use of a minicircle DNA-encoded transposon (TE) in combination with any potential source of transposase (including but not limited to mRNA, plasmid-DNA, minicircle-DNA, linear DNA, a polypeptide) to deliver a transgene into a lymphocyte.

Further, with regard to the preferred embodiment of the invention, the present invention describes for the first time the use of minicircle DNA-encoded transposon containing the genetic information for a tumor-reactive TCR or CAR in combination with mRNA-encoded sleeping beauty transposase SB100X to derive tumor-reactive human T lymphocytes for use in immunotherapy of cancer.

Further, the present invention describes an enabling technological advance given the significantly higher stable gene transfer rates and significantly reduced toxicity accomplished with the use of minicircle DNA-encoded transposon (TE) in combination with mRNA-encoded transposase compared to the established conventional method of using plasmid DNA-encoded transposase and plasmid DNA-encoded transposon (TE) in lymphocytes.

Our finding, that stable gene transfer can be accomplished with the use of a minicircle DNA-encoded transposon (TE) in combination with mRNA-encoded transposase is novel and has not been disclosed in the prior art; and unexpected, as mRNA is known to be short lived and rapidly degrades after insertion into the nucleus or cytoplasm of T lymphocytes and other mammalian cells.

It could thus neither be anticipated nor expected that mRNA as source for transposase would be suitable and sufficient to enable transposition from minicircle DNA, nor could it be anticipated or expected that the use of mRNA as source for transposase would result in even higher transposition rates compared to conventional, established methods that use plasmid-DNA encoded transposase and plasmid-DNA encoded transposons.

As used herein, the term “minicircle DNA” refers to vectors which are supercoiled DNA molecules that lack a bacterial origin of replication and an antibiotic resistance gene. Therefore they are primarily composed of a eukaryotic expression cassette (see, for instance, F. Jia et al. Nature methods, Vol. 7, no. 3, p. 197-199, March 2010).

As used herein, “genomic safe harbors” are regions of the human chromosomes that concurrently meet the following 5 criteria: not ultraconserved, more than 300 kb away from miRNA genes, more than 50 kb away from transcriptional start sites (TSS), more than 300 kb away from genes involved in cancer and outside transcription units.

As used herein, an “ultraconserved” genomic chromosomal region is a non-coding intragenic or intergenic region that is completely conserved in the human, mouse and rat genomes.

Preferred Embodiments

The preferred embodiment of the invention is the use of mRNA-encoded SB100X transposase and a minicircle DNA-encoded CAR transposon to generate tumor-reactive CAR-modified T lymphocytes for adoptive cancer immunotherapy.

In a useful embodiment, this CAR is specific for CD19, CD20, CD22, CD33, CD44v6, CD123, CD135, EpCAM, EGFR, EGFRvariants, GD2, ROR1, ROR2, CD269, CD319, CD38, CD138 or any other surface molecule expressed on a tumor cell, a diseased cell, or a normal cell.

In another useful embodiment, the minicircle DNA may encode an a/b or g/d T-cell receptor, a cytokine, a suicide gene, a transduction marker, or any other naturally occurring or synthetic molecule desirable to be introduced into a cell.

In another useful embodiment, the modified cell is a CD8+ killer T cell, a CD4+ helper T cell, a naïve T cell, a memory T cell, a central memory T cells, an effector memory T cell, a memory stem T cell, an invariant T cell, an NKT cell, a cytokine induced killer T cell, a g/d T cell, a B lymphocyte, a natural killer cell, a monocyte, a macrophage, a dendritic cell, a granulocyte, or any other mammalian cell type desirable to be used for genetic modification.

In a useful embodiment the mRNA and DNA minicircle are introduced into the cell by electrotransfer, such as electroporation, nucleofection; chemotransfer with substances such as lipofectamin, fugene, calcium phosphate; nanoparticles, or any other conceivable method suitable to transfer material into a cell.

In a useful embodiment, the transposase mediating transposition of the transposable element into the genome is Sleeping Beauty, PiggyBac, Frog Prince, Himarl, Passport, Minos, hAT, Tol1, Tol2, AciDs, PIF, Harbinger, Harbinger3-DR, and Hsmar1, and any of their respective derivatives with equal, lower and/or higher transposition activity.

In another useful embodiment of the invention, the SB100X transposase itself may be delivered as minicircle-DNA, linear DNA, a polypeptide or any other source suitable for accomplishing transposition of a minicircle-DNA encoded TE.

Particularly preferred embodiments of the invention are as defined in the following items:

1. Use of
   a combination of a minicircle DNA encoding a transposable element and
   a source of a transposase
   to stably integrate the transposable element into the genome of a mammalian cell.
2. The use according to item 1, wherein the source of the transposase is a nucleic acid encoding the transposase.
3. The use according to item 2, wherein the nucleic acid encoding the transposase is an mRNA encoding the transposase, a plasmid DNA encoding the transposase, a minicircle DNA encoding the transposase, or a linear DNA encoding the transposase.
4. The use according to item 3, wherein the nucleic acid encoding the transposase is an mRNA encoding the transposase.
5. The use according to item 3, wherein the nucleic acid encoding the transposase is a minicircle DNA encoding the transposase.
6. The use according to item 5, wherein the minicircle DNA encoding the transposase and the minicircle DNA encoding the transposable element is the same minicircle DNA.
7. The use according to item 1, wherein the source of the transposase is a transposase polypeptide.
8. The use according to any one of the preceding items, wherein the transposase is SB100X.
9. The use according to any one of the preceding items, wherein the mammalian cell is a mammalian lymphocyte.
10. The use according to item 9, wherein the mammalian lymphocyte is a human lymphocyte.
11. The use according to item 9 or 10, wherein the lymphocyte is a T lymphocyte.
12. The use according to any one of items 1 to 8, wherein the mammalian cell is a CD8+ killer T cell, a CD4+ helper T cell, a naive T cell, a memory T cell, a central memory T cell, an effector memory T cell, a memory stem T cell, an invariant T cell, an NKT cell, a cytokine induced killer T cell, a g/d T cell, a B lymphocyte, a natural killer cell, a monocyte, a macrophage, a dendritic cell, or a granulocyte.
13. The use according to any one of the preceding items, wherein the mammalian cell is a CD8+ killer T cell or a CD4+ helper T cell.
14. The use according to any one of the preceding items, wherein the transposable element contains the genetic information for the expression of a T-cell receptor or chimeric antigen receptor, and wherein the mammalian cell is a human T lymphocyte.
15. The use according to item 14, wherein the T-cell receptor or chimeric antigen receptor is tumor-reactive, and wherein the human T lymphocyte obtained by the use is a tumor-reactive human T lymphocyte suitable for use in the adoptive immunotherapy of cancer.

16. The use according to item 14 or 15, wherein the transposable element contains the genetic information for a chimeric antigen receptor.
17. The use according to item 16, wherein the chimeric antigen receptor is specific for CD19, CD20, CD22, CD33, CD44v6, CD123, CD135, EpCAM, EGFR, an EGFR variant, GD2, ROR1, ROR2, CD269, CD319, CD38, or CD138.
18. The use according to any one of the preceding items, wherein the minicircle DNA encoding the transposable element encodes an a/b or g/d T-cell receptor, a cytokine, a suicide gene, or a transduction marker.
19. The use according to any of the preceding items, wherein the use is an in vitro use.
20. The use according to any one of items 2-6 or 8-19, wherein the nucleic acid encoding the transposase and the DNA minicircle encoding the transposable element are introduced into the cell by electrotransfer, such as electroporation, nucleofection; chemotransfer, calcium phosphate; or nanoparticles.
21. The use according to any one of items 2-7 or 9-20, wherein the transposase mediating transposition of the transposable element into the genome is Sleeping Beauty, PiggyBac, Frog Prince, Himarl, Passport, Minos, hAT, Tol1, Tol2, AciDs, PIF, Harbinger, Harbinger3-DR, and Hsmar1, or a derivative thereof having transposition activity.
22. Use of a combination of:
 a DNA encoding a transposable element containing an expression cassette for a transgene and
 a source of a transposase
 to stably integrate the transposable element into the genome of a mammalian cell,
 wherein the DNA encoding the transposable element lacks an origin of replication and/or lacks an antibiotic resistance gene.
23. The use according to item 22, wherein the DNA encoding the transposable element lacks an origin of replication.
24. The use according to item 22, wherein the DNA encoding the transposable element lacks an antibiotic resistance gene.
25. The use according to any one of items 22 to 24, wherein the DNA encoding the transposable element lacks an origin of replication and lacks an antibiotic resistance gene.
26. The use according to any one of items 22 to 25, wherein the DNA encoding the transposable element is obtainable by deleting said origin of replication and/or said antibiotic resistance gene from a plasmid selected from the group consisting of:
 pT;
 pT2;
 a plasmid having a DNA sequence which is at least 90% identical to the DNA sequence of pT;
 a plasmid having a DNA sequence which is at least 90% identical to the DNA sequence of pT2; and
 any other plasmid which is suitable as a donor plasmid for transposable elements.
27. Use of a combination of:
 a DNA encoding a transposable element containing an expression cassette for a transgene and
 a source of a transposase
 to stably integrate the transposable element into the genome of a mammalian cell,
 wherein the DNA encoding the transposable element is obtainable by shortening a plasmid by at least one base pair, and wherein the plasmid is selected from the group consisting of:
 pT;
 pT2;
 a plasmid having a DNA sequence which is at least 90% identical to the DNA sequence of pT;
 a plasmid having a DNA sequence which is at least 90% identical to the DNA sequence of pT2; and
 any other plasmid which is suitable as a donor plasmid for transposable elements.
28. The use according to any one of items 22 to 27, wherein the total length of said DNA encoding the transposable element is not more than 3.0 kb, preferably not more than 2.0 kb greater than the length of said expression cassette.
29. The use according to any one of items 22 to 28, wherein the total length of said DNA encoding the transposable element is not more than 1.5 kb greater than the length of said expression cassette.
30. The use according to any one of items 22 to 29, wherein the total length of said DNA encoding the transposable element is not more than 1.0 kb greater than the length of said expression cassette.
31. The use according to any one of items 22 to 30, wherein the DNA encoding the transposable element is a minicircle DNA as used in any one of items 1 to 21.
32. The use according to any one of items 22 to 31, wherein the transgene is a T-cell receptor or chimeric antigen receptor as defined in any one of items 14 to 17, and wherein the mammalian cell is a human T lymphocyte.
33. The use according to any one of items 22 to 31, wherein the transgene is an a/b or g/d T-cell receptor, a cytokine, a suicide gene, or a transduction marker.
34. The use according to any one of items 22 to 33, wherein the use is an in vitro use.
35. The use according to any one of items 22 to 34, wherein the source of the transposase is as defined in any one of items 2-6, 8 or 21.
36. The use according to any one of items 22 to 31 and 33 to 35, wherein the mammalian cell is as defined in any one of items 9 to 14.
37. The use according to any one of the preceding items, wherein the mammalian cell is a primary cell, preferably a primary human cell.
38. The use according to any one of the preceding items, wherein the use is a non-viral use.
39. A method for obtaining a recombinant mammalian cell containing a stably integrated transposable element, the method comprising:
 introducing a combination of a minicircle DNA encoding the transposable element and a nucleic acid encoding a transposase into a mammalian cell,
 thereby obtaining the recombinant mammalian cell.
40. The method according to item 39, wherein the nucleic acid encoding the transposase is as defined in any one of items 3-6, 8 or 21.
41. The method according to any one of the preceding items, wherein the transposase is SB100X.
42. The method according to any one of the preceding items, wherein the mammalian cell is a mammalian lymphocyte.
43. The method according to item 42, wherein the mammalian lymphocyte is a human lymphocyte.

44. The method according to item 42 or 43, wherein the lymphocyte is a T lymphocyte.
45. The method according to any one of items 39 to 41, wherein the mammalian cell is a CD8+ killer T cell, a CD4+ helper T cell, a naive T cell, a memory T cell, a central memory T cell, an effector memory T cell, a memory stem T cell, an invariant T cell, an NKT cell, a cytokine induced killer T cell, a g/d T cell, a B lymphocyte, a natural killer cell, a monocyte, a macrophage, a dendritic cell, or a granulocyte.
46. The method according to any one of the preceding items, wherein the mammalian cell is a CD8+ killer T cell or a CD4+ helper T cell.
47. The method according to any one of the preceding items, wherein the transposable element contains the genetic information for the expression of a T-cell receptor or chimeric antigen receptor, and wherein the mammalian cell is a human T lymphocyte.
48. The method according to item 47, wherein the T-cell receptor or chimeric antigen receptor is tumor-reactive, and wherein the human T lymphocyte obtained by the method is a tumor-reactive human T lymphocyte suitable for use in the adoptive immunotherapy of cancer.
49. The method according to item 47 or 48, wherein the transposable element contains the genetic information for a chimeric antigen receptor.
50. The method according to item 49, wherein the chimeric antigen receptor is specific for CD19, CD20, CD22, CD33, CD44v6, CD123, CD135, EpCAM, EGFR, an EGFR variant, GD2, ROR1, ROR2, CD269, CD319, CD38, or CD138.
51. The method according to any one of the preceding items, wherein the minicircle DNA encoding the transposable element encodes an a/b or g/d T-cell receptor, a cytokine, a suicide gene, or a transduction marker.
52. The method according to any of the preceding items, wherein the method is an in vitro method.
53. The method according to any one of the preceding items, wherein the nucleic acid encoding the transposase and the DNA minicircle encoding the transposable element are introduced into the cell by electrotransfer, such as electroporation, nucleofection; chemotransfer, calcium phosphate; or nanoparticles.
54. The method according to any one of items 39-41 or 43-53, wherein the transposase mediating transposition of the transposable element into the genome is Sleeping Beauty, PiggyBac, Frog Prince, Himarl, Passport, Minos, hAT, Tol1, Tol2, AciDs, PIF, Harbinger, Harbinger3-DR, and Hsmar1, or a derivative thereof having transposition activity.
55. The method or use of any one of the preceding items, wherein the combination of the minicircle DNA encoding the transposable element and the nucleic acid encoding the transposase are introduced together into the mammalian cell.
56. The method or use of item 54, wherein the minicircle DNA encoding the transposable element and the nucleic acid encoding the transposase are the same minicircle DNA.
57. The method according to any of the preceding items, wherein the nucleic acid encoding the transposase and the minicircle DNA encoding the transposable element are introduced into the mammalian cell in a molar ratio of 1:1 or more, preferably in a molar ratio of 2:1 to 10:1, more preferably in a molar ratio of 3:1 to 9:1, still more preferably in a molar ratio of 4:1 to 8:1.
58. A method for obtaining a recombinant mammalian cell containing a stably integrated transposable element, the method comprising:
    introducing a combination of:
        a DNA encoding a transposable element containing an expression cassette for a transgene and
        a nucleic acid encoding a transposase
    into a mammalian cell,
    thereby obtaining the recombinant mammalian cell,
    wherein the DNA encoding the transposable element lacks an origin of replication and/or lacks an antibiotic resistance gene.
59. The method according to item 58, wherein the DNA encoding the transposable element lacks an origin of replication.
60. The method according to item 58 or 59, wherein the DNA encoding the transposable element lacks an antibiotic resistance gene.
61. The method according to any one of items 58 to 60, wherein the DNA encoding the transposable element lacks an origin of replication and lacks an antibiotic resistance gene.
62. The method according to any one of items 58 to 61, wherein the DNA encoding the transposable element is obtainable by deleting said origin of replication and/or said antibiotic resistance gene from a plasmid selected from the group consisting of:
    pT;
    pT2;
    a plasmid having a DNA sequence which is at least 90% identical to the DNA sequence of pT;
    a plasmid having a DNA sequence which is at least 90% identical to the DNA sequence of pT2; and
    any other plasmid which is suitable as a donor plasmid for transposable elements.
63. A method for obtaining a recombinant mammalian cell containing a stably integrated transposable element, the method comprising:
    introducing a combination of:
        a DNA encoding a transposable element containing an expression cassette for a transgene and
        a nucleic acid encoding a transposase
    into a mammalian cell,
    thereby obtaining the recombinant mammalian cell,
    wherein the DNA encoding the transposable element is obtainable by shortening a plasmid by at least one base pair, and wherein the plasmid is selected from the group consisting of:
    pT,
    pT2;
    a plasmid having a DNA sequence which is at least 90% identical to the DNA sequence of pT;
    a plasmid having a DNA sequence which is at least 90% identical to the DNA sequence of pT2; and
    any other plasmid which is suitable as a donor plasmid for transposable elements.
64. The method according to any one of items 58 to 63, wherein the total length of said DNA encoding the transposable element is not more than 3.0 kb, preferably not more than 2.0 kb greater than the length of said expression cassette.
65. The method according to any one of items 58 to 64, wherein the total length of said DNA encoding the transposable element is not more than 1.5 kb greater than the length of said expression cassette.
66. The method according to any one of items 58 to 65, wherein the total length of said DNA encoding the transposable element is not more than 1.0 kb greater than the length of said expression cassette.

67. The method according to any one of items 58 to 66, wherein the DNA encoding the transposable element is a minicircle DNA as used in any one of items 1 to 21.

68. The method according to any one of items 58 to 67, wherein the transgene is a T-cell receptor or chimeric antigen receptor as defined in any one of items 14 to 17, and wherein the mammalian cell is a human T lymphocyte.

69. The method according to any one of items 58 to 67, wherein the transgene is an a/b or g/d T-cell receptor, a cytokine, a suicide gene, or a transduction marker.

70. The method according to any one of items 58 to 69, wherein the method is an in vitro method.

71. The method according to any one of items 58 to 70, wherein the nucleic acid encoding the transposase is as defined in item 40.

72. The method according to any one of items 58 to 67 and 69 to 71, wherein the mammalian cell is as defined in any one of items 9 to 14.

73. The method according to any one of the preceding items, wherein the mammalian cell is a primary cell, preferably a primary human cell.

74. The method according to any one of the preceding items, wherein the method is a non-viral method.

75. The method according to any one of the preceding items, wherein said combination is introduced by introducing
the DNA or minicircle DNA encoding the transposable element and
the nucleic acid encoding the transposase
simultaneously.

76. The method according to item 75, wherein
said DNA or minicircle DNA encoding the transposable element and
said nucleic acid encoding the transposase
is the same DNA minicircle.

77. The method according to any one of items 39 to 54 and 56 to 74, wherein said combination is introduced by introducing
said nucleic acid encoding the transposase
and said DNA or minicircle DNA encoding the transposable element
sequentially.

78. The method according to any one of items 39 to 54 and 56 to 74, wherein said combination is introduced by introducing
said DNA or minicircle DNA encoding the transposable element
and said nucleic acid encoding the transposase
sequentially.

79. The method or use according to any one of the preceding items, wherein the minicircle DNA encoding the transposable element is a linearized DNA or a circular DNA.

80. The method or use according to any one of the preceding items, wherein the source of the transposase, or the nucleic acid encoding the transposase, is a minicircle DNA encoding the transposase, which is a linearized minicircle DNA or a circular minicircle DNA.

81. The method according to any of the preceding items, wherein the nucleic acid encoding the transposase and the DNA or minicircle DNA encoding the transposable element are introduced into the mammalian cell in a weight ratio of 1:1 or more, preferably in a weight ratio of 2:1 to 10:1, more preferably in a weight ratio of 3:1 to 9:1, still more preferably in a weight ratio of 4:1 to 8:1.

82. A recombinant mammalian cell obtainable by the method according to any one of the preceding items.

83. A recombinant human T-cell containing at least one copy of a transposable element containing an expression cassette for a transgene.

84. The recombinant cell of item 82 or 83, wherein the copy number of the transposable element in said cell is at least 1, at least 2, at least 3, at least 4, at least 5, at least 6, at least 7, at least 8, at least 9 or at least 10.

85. The recombinant cell of item 82 or 83, wherein the copy number of the transposable element in said cell is at least 3, at least 4, at least 5, at least 6, at least 7, at least 8, at least 9 or at least 10.

86. The recombinant cell according to any one of the preceding items, wherein 0% to 5% of the copies of the transposable element in the chromosomal genome of the recombinant cell are integrated in genomic chromosomal regions which satisfy all of the following criteria:
(i) not ultraconserved,
(ii) more than 300 kb away from miRNA genes,
(iii) more than 50 kb away from transcriptional start sites,
(iv) more than 300 kb away from genes involved in cancer, and
(v) outside transcription units.

87. The recombinant cell according to any one of the preceding items, wherein at least 5% of the copies of the transposable element in the chromosomal genome of the recombinant cell are integrated in genomic chromosomal regions which satisfy all of the following criteria:
(i) not ultraconserved,
(ii) more than 300 kb away from miRNA genes,
(iii) more than 50 kb away from transcriptional start sites,
(iv) more than 300 kb away from genes involved in cancer, and
(v) outside transcription units.

88. The recombinant cell according to any one of the preceding items, wherein at least 10% of the copies of the transposable element in the chromosomal genome of the recombinant cell are integrated in genomic chromosomal regions which satisfy all of the following criteria:
(i) not ultraconserved,
(ii) more than 300 kb away from miRNA genes,
(iii) more than 50 kb away from transcriptional start sites,
(iv) more than 300 kb away from genes involved in cancer, and
(v) outside transcription units.

89. The recombinant cell according to any one of the preceding items, wherein at least 15% of the copies of the transposable element in the chromosomal genome of the recombinant cell are integrated in genomic chromosomal regions which satisfy all of the following criteria:
(i) not ultraconserved,
(ii) more than 300 kb away from miRNA genes,
(iii) more than 50 kb away from transcriptional start sites,
(iv) more than 300 kb away from genes involved in cancer, and (v) outside transcription units.

90. The recombinant cell according to any one of the preceding items, wherein at least 20% of the copies of the transposable element in the chromosomal genome of the recombinant cell are integrated in genomic chromosomal regions which satisfy all of the following criteria:
(i) not ultraconserved,
(ii) more than 300 kb away from miRNA genes,
(iii) more than 50 kb away from transcriptional start sites,
(iv) more than 300 kb away from genes involved in cancer, and
(v) outside transcription units.

91. The recombinant cell according to any one of the preceding items, wherein at least 40% of the copies of the transposable element in the chromosomal genome of the recombinant cell are integrated in genomic chromosomal regions which satisfy the following criterion:
(v) outside transcription units.

92. The recombinant cell according to any one of the preceding items, wherein at least one, preferably all copies of the transposable element in the chromosomal genome of the recombinant cell are integrated in genomic chromosomal regions which satisfy at least any one of the following criteria:
(i) not ultraconserved,
(ii) more than 300 kb away from miRNA genes,
(iii) more than 50 kb away from transcriptional start sites,
(iv) more than 300 kb away from genes involved in cancer, and
(v) outside transcription units.

93. The recombinant cell according to any one of the preceding items, wherein at least one, preferably all copies of the transposable element in the chromosomal genome of the recombinant cell are integrated in genomic chromosomal regions which satisfy at least any two of the following criteria:
(i) not ultraconserved,
(ii) more than 300 kb away from miRNA genes,
(iii) more than 50 kb away from transcriptional start sites,
(iv) more than 300 kb away from genes involved in cancer, and
(v) outside transcription units.

94. The recombinant cell according to any one of the preceding items, wherein at least one, preferably all copies of the transposable element in the chromosomal genome of the recombinant cell are integrated in genomic chromosomal regions which satisfy at least any three of the following criteria:
(i) not ultraconserved,
(ii) more than 300 kb away from miRNA genes,
(iii) more than 50 kb away from transcriptional start sites,
(iv) more than 300 kb away from genes involved in cancer, and
(v) outside transcription units.

95. The recombinant cell according to any one of the preceding items, wherein at least one, preferably all copies of the transposable element in the chromosomal genome of the recombinant cell are integrated in genomic chromosomal regions which satisfy at least any four of the following criteria:
(i) not ultraconserved,
(ii) more than 300 kb away from miRNA genes,
(iii) more than 50 kb away from transcriptional start sites,
(iv) more than 300 kb away from genes involved in cancer, and
(v) outside transcription units.

96. The recombinant cell according to any one of the preceding items, wherein the copy number of the transposable element in the chromosomal genome of the recombinant cell is at least 1, at least 2, at least 3, at least 4, at least 5, at least 6, at least 7, at least 8, at least 9 or at least 10.

97. The recombinant cell according to any one of items 81 to 94, wherein the copy number of transient copies of the transposable element in the recombinant cell is at least 1, at least 2, at least 3, at least 4, at least 5, at least 6, at least 7, at least 8, at least 9 or at least 10.

98. A recombinant cell according to any of the preceding items, for use in medicine.

99. A recombinant cell according to any of items 82 to 97, for use in the treatment of cancer.

100. The recombinant cell according to any of items 98 or 99 for the use according to any of items 97 or 98, wherein the use is a use in immunotherapy.

101. The recombinant cell according to item 100 for the use according to item 100, wherein the use in immunotherapy is a use for the treatment of an autoimmune disease.

102. The recombinant cell according to item 100 for the use according to item 100, wherein the use in immunotherapy is a use for the treatment of an infectious disease.

103. The recombinant cell according to item 102 for the use according to item 102, wherein the infectious disease is a bacterial infection, a viral infection or a fungal infection.

104. The recombinant cell according to any one of items 98 to 103 for the use according to any one of items 98 to 103, wherein the recombinant cell is a T cell.

105. A recombinant cell according to any of items 82 to 97, for use in gene therapy.

106. A composition comprising a minicircle DNA encoding a transposable element and a nucleic acid encoding the transposase.

107. The composition according to item 106, wherein the nucleic acid encoding the transposase is as defined in any one of items 3-6, 8 or 21.

108. The composition according to item 106 or 107, wherein the transposable element is as defined in any one of items 14-18.

109. The use or method according to any one of items 1-18, 20-33, 35-51, 53-69, or 71-81, wherein the use or method is an in vivo use or an in vivo method, 110. The use or method according to item 109, wherein the use or method is a use in gene therapy or a method for gene therapy.

The present invention is exemplified by the following non-limiting examples:

EXAMPLES

Example 1: Preparation of CAR-Modified Human CD8+ and CD4+ T Cells Using Sleeping Beauty-Mediated Transposition with mRNA-Encoded Hyperactive Sleeping Beauty Transposase 100X (SB100X) and Minicircle DNA-Encoded eGFP or CD19-CAR Transgenes Materials and Methods:

Human Subjects

Blood samples were obtained from healthy donors who provided written informed consent to participate in research protocols approved by the Institutional Review Board of the University of Würzburg (Universitätsklinikum Würzburg, UKW). Peripheral blood mononuclear cells (PBMC) were isolated by centrifugation over Ficoll-Hypaque (Sigma, St. Louis, MO).

Cell Lines 293T cells (ATCC: CRL-11268, American Type Culture Collection, Manassas, VA) were cultured in Dulbecco's modified Eagle's medium supplemented with 10% fetal calf serum and 100 U/ml penicillin/streptomycin. K562 (ATCC: CCL-243), K562/ROR1, K562/CD19, Raji (ATCC: CCL-86), JeKo-1 (ATCC: CRL-3006), and JeKo-1-ffluc cells were cultured in RPMI 1640 medium supplemented with 10% fetal calf serum and 100 U/ml penicillin/streptomycin (all cell culture media and supplements: GIBCO, Carlsbad, CA).

Immunophenotyping

PBMC and T cell lines were stained with one or more of the following conjugated mAb: CD3, CD4, CD8, CD25, CD45, CD45RA, CD45RO, CD62L, CD69 and matched isotype controls (BD Biosciences, San Jose, CA). Transduced T cell lines were stained with biotin-conjugated anti-EGFR antibody (ImClone Systems Incorporated, Branchburg, NJ) and streptavidin-PE (BD Biosciences, San Jose, CA)[Ref. 27]. Staining with 7-AAD (BD Biosciences) was performed for live/dead cell discrimination as directed by the manufacturer. Flow analyses were done on a FACSCanto, sort-purifications on a FACSAriaII (Becton Dickinson, Franklin Lakes, NJ) and data analyzed using FlowJo software (Treestar, Ashland, OR).

Lentiviral Vector Construction, Preparation of Lentivirus, and Generation of CAR-T Cells The construction of epHIV7 lentiviral vectors containing CD19-specific CARs with a short spacer and a 4-1BB costimulatory domain has been described (Hudecek *Clin Cancer Res* 2013). All CAR constructs encoded a truncated epidermal growth factor receptor (EGFRt; also known as tEGFR) sequence (Wang *Blood* 2011) downstream of the CAR. The genes were linked by a T2A ribosomal skip element.

CAR/EGFRt and ffluc/eGFP-encoding lentivirus supernatants were produced in 293T cells co-transfected with each of the lentiviral vector plasmids and the packaging vectors pCHGP-2, pCMV-Rev2 and pCMV-G using Calphos transfection reagent (Clontech, Mountain View, CA). Medium was changed 16 h after transfection, and lentivirus collected after 24, 48 and 72 h. CAR-T cells were generated as described (Hudecek *Clin Cancer Res* 2013). In brief, CD8+ bulk T cells, CD8+ $T_{CM}$ and CD4+ bulk T cells were sorted from PBMC of healthy donors, activated with anti-CD3/CD28 beads (Life Technologies), and transduced with lentiviral supernatant. Lentiviral transduction was performed on day 1 by spinoculation, and T cells propagated in RPMI-1640 with 10% human serum, glutamin, 100 U/mL penicillin-streptomycin and 50 U/mL IL-2. Trypan blue staining was performed to quantify viable T cells. After expansion, EGFRt$^+$ T cells were enriched and stimulated with irradiated B-LCL.

Transposon Vector Construction

The transposon vector pT2/HB (Addgen #26557) was obtained from Addgene. To derive a transposon vector encoding enhanced green fluorescent protein (pT2/HB: eGFP), a codon optimized gene encoding a HindIII restriction site, an EF1/HTLV hybrid promotor, a NheI restriction site upstream of a Kozak sequence and a sequence encoding enhanced GFP (eGFP) followed by a Stop codon, as well as NotI and BamHI restriction sites was synthesized and subcloned into pT2/HB using the HindIII and BamHI sites using commercial vendors (GeneArt, Regensburg). To derive a transposon vector encoding a CD19-specific CAR (pT2/HB:CD19-CAR), the CD19-CAR_tEGFR gene described above (Section: lentiviral vector construction) was obtained from the lentiviral vector by restriction digest and subcloned into pT2/HB:eGFP using the NheI and NotI restriction sites to replace the eGFP transgene. The vector encoding hyperactive sleeping beauty 100X (SB100X) transposase was obtained from Addgene (Addgene #34879: pCMV(CAT)T7-SB100).

Preparation of DNA Minicircles and SB100X mRNA

DNA minicircles were produced by Plasmid Factory (Bielefeld) using a proprietary protocol: i) pT2/HB: eGFP→MC-GFP; ii) pT2/HB:CD19-CAR→MC-CD19 CAR; and iii) pCMV(CAT)T7-SB100→MC-SB100X. Minicircles were purified by affinity chromatography. SB100X mRNA was produced by in vitro transcription (IVT) using standard protocols at EUFETS (Idar-Oberstein), or produced in-house using the mMessage mMachine kit (Ambion).

Generation of GFP- and CAR-Expressing T Cells Through SB Transposition

CD8+ bulk T cells, CD8+ $T_{CM}$ and/or CD4+ bulk T cells were sorted from PBMC of healthy donors, activated with anti-CD3/CD28 beads (Life Technologies), and nucleofected in a 4D nucleofector device according to the manufacturer's instructions (Lonza, Köln) in nucleofection buffer/supplement containing plasmid DNA, minicircle DNA and/or mRNA using a protocol optimized for activated human T lymphocytes. T cells were maintained and propagated in T-cell medium (RPMI/10% human serum/glutamin/pen-strep). Phenotypic analysis was performed at regular intervals following nucleofection to determine the proportion of T cells expressing the introduced transgene. Cell counting with trypan blue staining was performed to determine the number of viable cells in the cell culture at distinct time point after nucleofection and during expansion.

Cytotoxicity, Cytokine Secretion, and CFSE Proliferation Assays

Target cells stably expressing firefly luciferase were incubated in triplicate at $5\times10^3$ cells/well with effector T cells at various effector to target (E:T) ratios. After a four-hour incubation luciferin substrate was added to the co-culture and the decrease in luminescence signal in wells that contained target cells and T cells, compared to target cells alone, measured using a luminometer (Tecan). Specific lysis was calculated using the standard formula[Ref. 31]. For analysis of cytokine secretion, $50\times10^3$ T cells were plated in triplicate wells with target cells at a ratio of 1:1 (K562/CD64), 2:1 (Raji), or 4:1 (K562/CD19 and K562), and IFN-γ, TNF-α, and IL-2 measured by multiplex cytokine immunoassay (Luminex) or ELISA (Biolegend) in supernatant removed after a 24-hour incubation. For analysis of proliferation, $50\times10^3$ T cells were labeled with 0.2 μM carboxyfluorescein succinimidyl ester (CFSE, Invitrogen), washed and plated in triplicate wells with target cells at a ratio of 2:1 (Raji) or 4:1 (K562/CD19, K562/ROR1 and K562) in CTL medium without exogenous cytokines. After 72 h of incubation, cells were labeled with anti-CD3 or anti-CD4 or anti-CD8 mAb and 7-AAD to exclude dead cells from analysis. Samples were analyzed by flow cytometry and cell division of live T cells assessed by CFSE dilution. The proliferation index was calculated using FlowJo software.

Adoptive Transfer of T Cells in NOD/SCID/$\gamma c^{-/-}$ (NSG) Mice

The UKW Institutional Animal Care and Use Committee approved all mouse experiments. Six- to eight-week old female NSG mice were obtained from the Charles River Laboratory or bred in-house. Six- to eight-week old female NSG mice were inoculated with $5\times10^5$ firefly luciferase expressing Raji tumor cells by tail vein injection on day 0. On day 7, groups of n=5 mice received i.v. injections of $5\times10^6$ CAR-modified or unmodified control T cells (containing equal proportions of $CD8^+$ and $CD4^+$ T cells). Bioluminescence imaging was performed to determine tumor burden and distribution, and Kaplan-Meier analyses done to measure survival.

Copy Number Determination of Transposon Insertions in T Cell Clones

T cell clones were prepared by limiting dilution at least one month post-transfection with SB100X mRNA and CD19-CAR MC and their genomic DNA digested with FspBI and DpnI restriction enzymes. Two-step nested PCR was performed (details: see below) and the PCR-product analyzed by gel electrophoresis.

More particularly, genomic DNA was isolated from $EGFRt^+$ T cell clones at least one month post-transfection of SB100X mRNA and MC transposon. 1 μg of DNA per clone was digested with FspBI (Thermo) and DpnI (NEB). The latter digest was applied to fragment parental MC, which could otherwise disturb the copy number determination. The digested DNA was column purified, and eluted in 20 μl. 5 μl was ligated with 50 pmol of FspBI overhang-specific linkers overnight at 16° C. Linkers were created by annealing the 100-100 pmol of the oligonucleotides L(+) and L(−)FspBI in 10 mMTris-CI pH8, 50 mM NaCl, 0.5 mM EDTA. 1 μl of the ligation reaction was used as the template for the first PCR reaction with the primers Linker (specific for the ligated linker) and T-Bal-rev (specific for the 5' terminal inverted repeat of the transposons) using following conditions: 94° C. 3 min; 10 cycles of: 94° C. 30 s, ramp to 63° C. (1° C./s), 30 s, 72° C. 1 min; 25 cycles of: 94° C. 30 s, ramp to 61° C. (1° C./s) 30 s, 72° C. 1 min; 72° C. 10 min. 1 μl of 100-times diluted PCR reaction was used in the nested PCR with the primers Nested and T-Bal with these conditions: 94° C. 3 min; 10 cycles of: 94° C. 30 s, ramp to 65° C. (1° C./s), 30 s, 72° C. 1 min; 25 cycles of: 94° C. 30 s, ramp to 63° C. (1° C./s) 30 s, 72° C. 1 min; 72° C. 10 min. 5 μl of the nested PCR reaction was loaded on a 1% agarose gel to visualize the bands, which correspond to the insertion sites with flanking genomic DNA.

Construction of the SB Insertion Library and Sequencing

Genomic DNA was isolated from CD8+ CAR T cell lines of n=3 donors, sheared using an ultra-solicitor and the genomic region around each integration site amplified by three-step PCR (details: see below). The final PCR product was run on a 1% agarose gel, the 200-500 bp smear purified and sequenced (IlluminaHiSeq, BeckmanCoulter Genomics).

More particularly, genomic DNA of $CD8^+$ $EGFRt^+$ T cells of three donors were isolated at least one month post-transfection. 2 μg DNA was sheared with a Covaris M220 ultra-solicitor device to an average fragment size of 600 bp in Screw-Cap microTUBEs in 50 μl, using the following settings: peak incident power 50 W, duty factor 20%, cycles per burst 200, treatment 28 s. 1.2 μg of the sheared DNA was blunted and 5'-phosphorylated using the NEBNext End Repair Module (NEB), and 3'-A-tailed with NEBNext dA-Tailing Module (NEB) following the recommendations of the manufacturer. The DNA was purified with the Clean and Concentrator Kit (Zymo) and eluted in 8 μl 10 mM Tris pH8 (EB) for ligation with 50 pmol of T-linker (see below) with T4 ligase (NEB) in 20 μl volume, at 16° C., overnight. T-linkers were created by annealing the 100-100 pmol of the oligonucleotides Linker_TruSeq_T+ and Linker_TruSeq_T− in 10 mMTris-Cl pH8, 50 mM NaCl, 0.5 mM EDTA. After heat-inactivation, ligation products enclosing fragments of non-integrated transposon donor plasmid DNA were digested with DpnI (NEB) in 50 μl for 3 hours and the DNA was column-purified and eluted in 20 μl EB. 6 μl eluate was used for the PCR 1 with 25 pmol of the primers specific for the linker and for the transposon inverted repeat: Linker and T-Bal-Long, respectively, with the conditions: 98° C. 30 s; 10 cycles of: 98° C. 10 s, 72° C. 30 s; 15 cycles of: 98° C. 10 s, ramp to 62° C. (1° C./s) 30 s, 72° C. 30 s, 72° C. 5 min. All PCR reactions were performed with NEBNext High-Fidelity 2× PCR Master Mix (for PCR primer sequences see table below). The PCR was column purified eluted in 20 μl EB and 10 μl used for PCR II with the primers: Nested and LAM-SB-50, with the following program: 98° C. 30 s; 12 cycles of: 98° C. 10 s, ramp to 65° C. (1° C./s) 30 s, 72° C. 30 s, 72° C. 5 min. One third of the column-purified PCR II was used for PCR III with the primers PE-nest-ind-N and SB-20-bc-ill-N (where N is the number of the Illumina TrueSeq indexes for barcoding the samples of different T-cell donors just to track them after Illumina sequencing) for barcoding the samples of different T cell donors, using the following PCR program: 98° C. 30 s; 12 cycles of: 98° C. 10 s, ramp to 64° C. (1° C./s) 30 s, 72° C. 30 s, 72° C. 5 min. The final PCR products were separated on a 1% agarose gel and the smears of 200-500 bp were gel-isolated and purified. The libraries were sequenced on an Illumina HiSeq instrument at Beckman Coulter Genomics on a rapid flow-cell using single-end 100 nucleotide sequencing setup.

| Primer name | Sequence |
|---|---|
| L(+) | GTAATACGACTCACTATAGGGCTCCGCTTAAGGGAC (SEQ ID NO: 1) |
| L(-)FspBI | TAGTCCCTTAAGCGGAG-AMINO (SEQ ID NO: 2) |
| Nested | AGGGCTCCGCTTAAGGGAC (SEQ ID NO: 3) |
| Linker | GTAATACGACTCACTATAGGGC (SEQ ID NO: 4) |
| T_Bal rev | GAATTGTGATACAGTGAATTATAAGTG (SEQ ID NO: 5) |
| T_Bal | CTTGTGTCATGCACAAAGTAGATGTCC (SEQ ID NO: 6) |
| T_Bal_long | CTTGTGTCATGCACAAAGTAGATGTCCTAACTGACT |

-continued

| Primer name | Sequence |
|---|---|
| | (SEQ ID NO: 7) |
| LAM_SB_50 | AGTTTTAATGACTCCAACTTAAGTG (SEQ ID NO: 8) |
| SB20h-bc-ill-N | AATGATACGGCGACCACCGAGATCTACACTCTTTCCCT ACACGACGCTCTTCCGATCT-TRUSEQ-ILLUMINA-INDEX-CTTAAGTGTATGTAAACTTCCGACT (SEQ ID NO: 9) |
| PE-nest-ind1-N | CAAGCAGAAGACGGCATACGAGAT-REVERSE-COMPLEMENT-OF-TRUSEQ-ILLUMINA-INDEX-GTGACTGGAGTTCAGACGTGTGCTCTTCCGATCT (SEQ ID NO: 10) |
| Linker_TruSeq_T+ | GTAATACGACTCACTATAGGGCTCCGCTTAAGGGACTC AGACGTGTGCTCTTCCGATCT (SEQ ID NO: 11) |
| Linker_TruSeq_T- | GATCGGAAGAGCACACG-AMINO (SEQ ID NO: 12) |
| PE_NEST_IND6 | CAAGCAGAAGACGGCATACGAGATATTGGCGTGACTGGAGTTC AGACGTGTGCTCTTCCGATCT (SEQ ID NO: 13) |
| PE_NEST_IND7 | CAAGCAGAAGACGGCATACGAGATAGTCTGGTGACTGGAGTTC AGACGTGTGCTCTTCCGATCT (SEQ ID NO: 14) |
| PE_NEST_IND8 | CAAGCAGAAGACGGCATACGAGATTCAAGTGTGACTGGAGTTC AGACGTGTGCTCTTCCGATCT (SEQ ID NO: 15) |

Bioinformatic Analysis

Reads were allocated to each donor using barcodes, trimmed using the Shortread tool in R software[Ref. 51] and the remaining sequences quality-trimmed as soon as 2 of 5 nucleotides had a phred score less than 20. The resulting reads were uniquely mapped to the hg19 human genome assembly with Bowtie[Ref. 52]. Any SB insertion site was considered valid if there were at least 10 independent reads supporting it. Nucleotide compositions of SB insertion sites were calculated and plotted using the SeqLogo tool in R software.

We used BEDtools v2.17.0[Ref. 53] for annotating the insertion sites or a set of computationally generated 10.000 random genomic positions in annotated human genomic features (http://genome.ucsc.edu). The set of cancer-related genes was obtained from http://www.bushmanlab.org/links/genelists[Ref. 39]. The category non-genic was created by subtracting the coordinates of all annotated transcripts from the chromosome lengths of the hg19 genome assembly. For relating insertion site frequencies of SB and HIV to gene expression levels, the inventors used published gene expression data of activated human T cells[Ref. 37].

BED files of ChIP-Seq data obtained on activated human T cells were retrieved from http://dir.nhlbi.nih.gov/papers/lmi/epigenomes/hgtcell.aspx[Ref. 54] and the MACS ChIP-Seq peak-calling algorithm[Ref. 55] "macs14 -t*.bed -g hs --nomodel --nolambda --space=30".

Genomic coordinates of ultraconserved elements were obtained[Ref. 56] and all human miRNA genes downloaded (http://www.mirbase.org/ftp.shtml). The 'genomic safe harbor' coordinates were obtained by intersecting all coordinates of all safe harbor subcategories for the hg19 human genome assembly.

Statistics

Statistical analyses were performed using Prism software (GraphPad). Results with $p<0.05$ were considered significant.

Results

Figure 1:
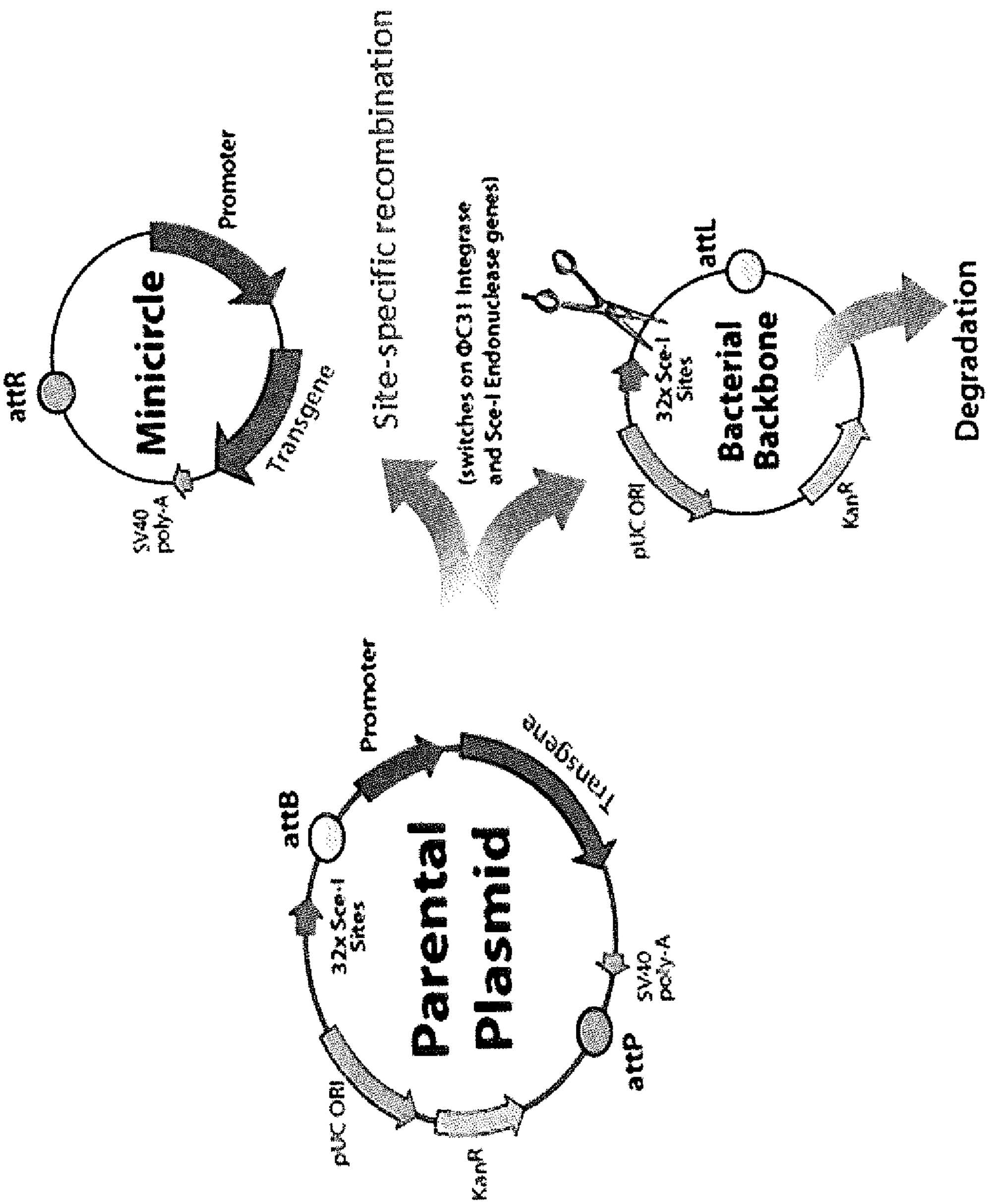
FIG. 1. Minicircle DNA and SB100X mRNA.
Figure 1:
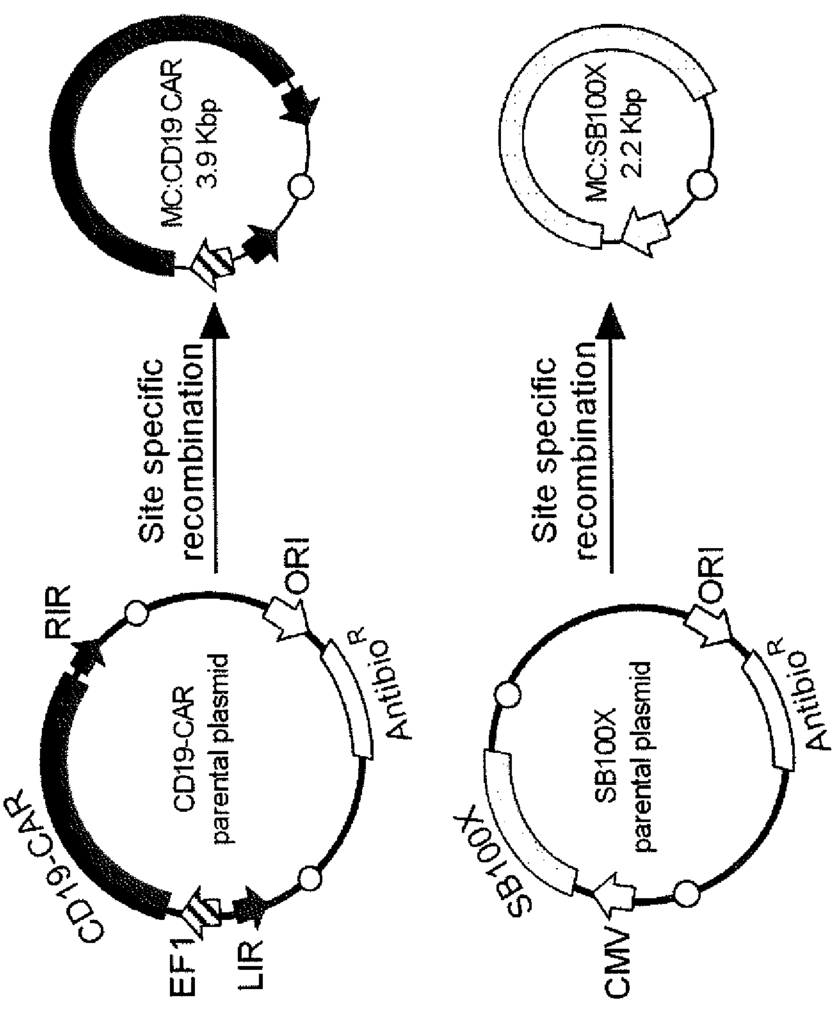
Figure 1:
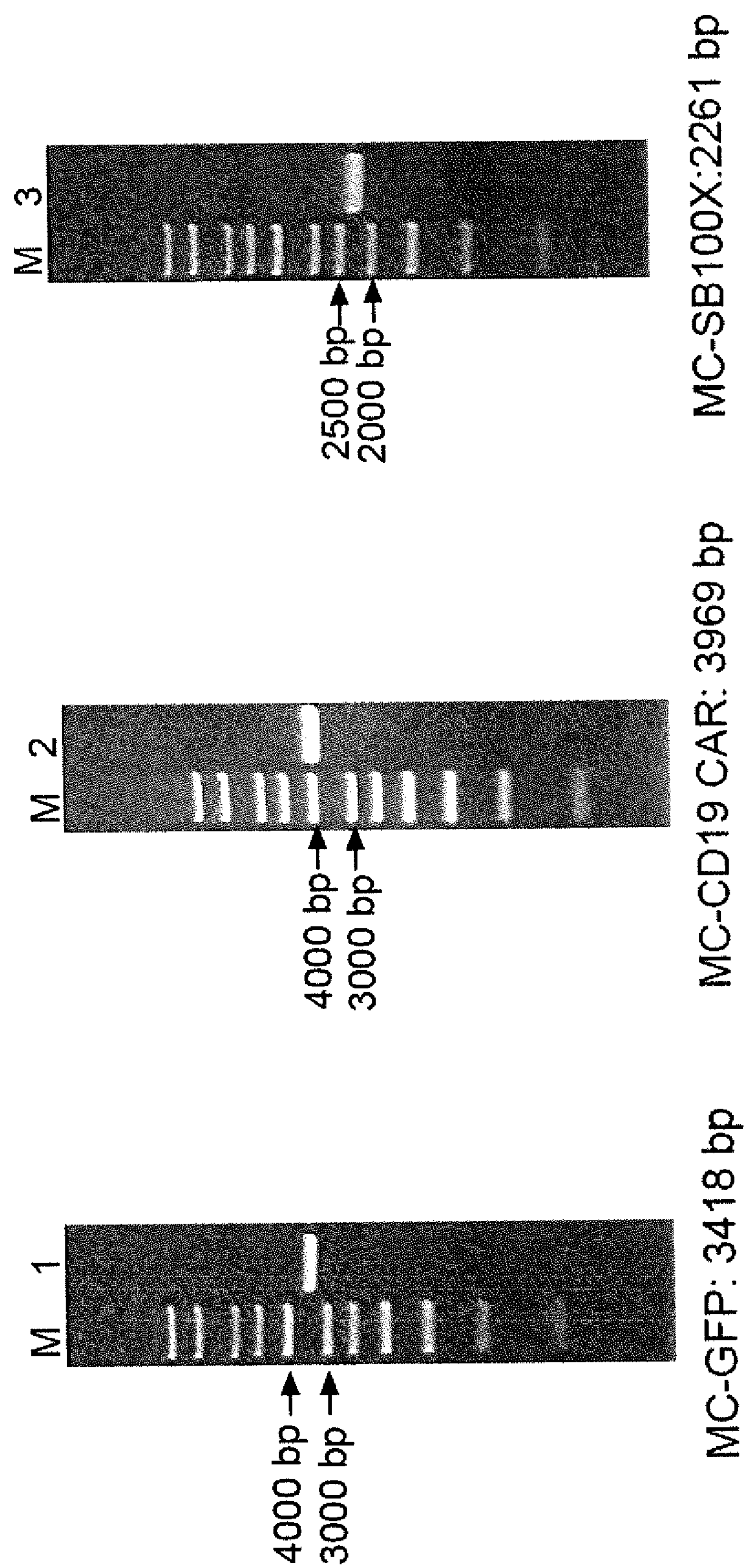
Figure 1:
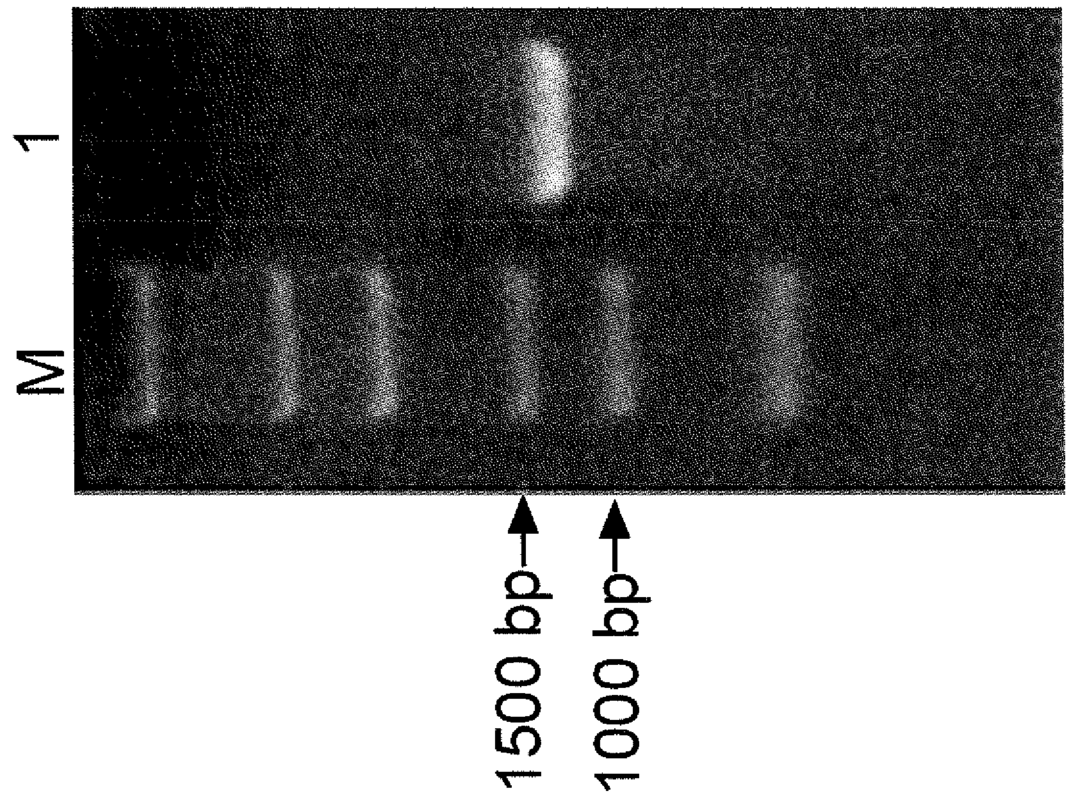

Transposition Using MC-Encoded Transposase and Transposon Enables High Level Stable Gene Transfer and Reduces Toxicity Associated with DNA Transfection MCs were prepared from a set of parental pT2 transposon donor vectors expressing an optimized CD19-CAR in cis with an EGFRt transduction marker[Ref. 27,28] or eGFP, and from a plasmid encoding hyperactive SB100X transposase (FIG. 1B). Then, transfections were performed into $CD8^+$ T cells of healthy donors and compared transposition rate and stability of transgene expression that could be accomplished when transposon and transposase were delivered as MCs (MC-MC) or plasmids (P-P). In all experiments, equal amounts of transposon and transposase vector, and equimolar amounts of MCs and their corresponding plasmids were transfected. Significantly higher transposition rates were found in T cells that were modified with the MC combination at all analyzed time points after transfection. On day 14, the mean percentage of CAR-modified (i.e. $EGFRt^+$) T cells was 49.8% with MCs but only 12.8% with plasmids, and thus on average 4.4-fold higher after transfection of MC—rather than plasmid-encoded SB100X transposase and CAR transposon (n=7, $p<0.0001$). The percentage of $EGFRt^+$ T cells remained stable after day 14 and even moderately increased over time in resting T cells, potentially due to intrinsic signaling of the CD19-CAR[33] (FIG. 3B). T cells that were selected for EGFRt and expanded with $CD19^+$ feeder cells showed stable transgene expression over multiple expansion cycles and for at least another 6 weeks in culture. Similar data on transposition efficacy were obtained with eGFP in $CD8^+$ T cells (FIG. 8A, B), and with both CD19-CAR and eGFP in $CD4^+$ T cells from multiple donors, confirming the present observation that MCs are superior to conventional plasmids in mediating transposition (FIG. 9).

The rapid manufacture of therapeutically relevant numbers of gene-modified T cells by SB transposition has been limited by severe toxicity following electrotransfection of plasmid DNA. The inventors found that, in addition to mediating superior transposition, MCs were also less toxic to T cells. The percentage of viable T cells 48 hours after transfection was on average 1.4-fold (CD19-CAR) and 3.2-fold (eGFP) higher in $CD8^+$ T cells modified with MCs compared to plasmids (both: n=3, p<0.05) (FIG. 2D; FIG. 3B; FIG. 8C). The higher transposition rate and lower toxicity of MCs translated into an approx. 6-fold higher yield of CD19-CAR T cells that could be obtained within 14 days of culture, even without antigen-dependent expansion (n=4, p<0.05) (FIG. 3E). Collectively, these data demonstrate that the use of MCs as transposon and transposase donor vectors is feasible, highly efficient and superior to plasmid DNA in mediating transposition in human T cells.

Transposition from MCs Using mRNA-Encoded SB Transposase

Next, it was investigated whether providing SB100X as mRNA instead of MC DNA was sufficient for accomplishing transposition from MC transposon donor vectors. Titration experiments were performed to determine the optimal ratio of SB100X mRNA and MC (1:1, 2:1, 4:1, 8:1), and analyzed EGFRt expression by flow cytometry on day 14 post-transfection. Superior transposition rates were found with the mRNA-MC combination compared to plasmids at all ratios (FIG. 2B, C). The highest transposition rate was achieved when SB100X mRNA and CD19-CAR MC were used at a 4:1 ratio, which yielded a 3.7-fold higher gene transfer rate than the plasmid combination (P-P) (n=3; p<0.001), and no substantial difference compared to the MC combination (FIG. 2B, C). A further increase in the amount of SB100X mRNA (8:1 ratio) resulted in a decline of transposition efficacy, potentially due to an overproduction inhibition effect[Ref. 34]. Also the use of SB100X mRNA in combination with MC transposons was associated with a significantly higher proportion of viable T cells 48 hours post-transfection compared to plasmids (1.4-fold higher; n=3; p<0.05). This again translated into a substantially higher yield of gene-modified T cells at the end of a 14-day culture period (mean 3.6-fold higher; n=4) (FIG. 3B). Importantly, the transposition rate that the inventors accomplished with the optimal SB100X mRNA and CD19-CAR MC combination (4:1 ratio) was similarly high in purified naïve, central memory and effector memory $CD8^+$ T cells (FIG. 10), indicating that this gene transfer strategy would not introduce a bias into which of these phenotypically and functionally distinct subsets was modified with the CD19-CAR in a bulk $CD8^+$ T cell population. Collectively, these data demonstrate that providing SB100X as relatively short-lived mRNA is sufficient to accomplish transposition from MC transposon donor vectors, with superior levels of stable gene transfer and enhanced T cell viability compared to plasmids.

MC Transposition Confers Potent Anti-Tumor Functions of CD19-CAR T Cells In Vitro and In Vivo Next, the function of T cells that were CAR-modified by SB transposition from MCs and plasmids was analyzed, and their potency was compared to T cells that were modified with the same CD19-CAR construct by LV transduction. Sets of CAR-modified and control untransduced $CD8^+$ and $CD4^+$ T cell lines were prepared from n=3 donors, and CAR-expressing T cells were enriched to >90% purity using the EGFRt marker (FIG. 4A). First, cytolytic activity was evaluated using K562 cells stably expressing CD19, and Raji and JeKo-1 lymphoma as target cells. The various $CD8^+$ CD19-CAR T cell lines modified by mRNA-MC, MC-MC and P-P transposition conferred similarly potent and specific lysis, at levels that were equivalent to that observed with CAR T cells generated by LV transduction (FIG. 4B). Quantitative cytokine analysis after co-culture with $CD19^+$ lymphoma also showed comparable production of IFN-γ and IL-2 in all $CD8^+$ and $CD4^+$ CD19-CAR T cell lines (FIG. 4C). Further, similarly productive proliferation (≥3 cell divisions in 72 hours) was found in all $CD8^+$ and $CD4^+$ CD19-CAR T cell lines by CFSE dilution, regardless whether they had been gene-modified by SB transposition or LV transduction (FIG. 4D, E).

Next, anti-tumor efficacy was analyzed in a systemic $CD19^+$ lymphoma xenograft model (NSG/Raji-ffLuc), and the analysis was focused on CAR T cells that were modified with SB100X mRNA and CD19-CAR MC, as this would be the most relevant combination for clinical translation. The experiments confirmed a potent anti-tumor effect that was mediated by a single dose of SB-modified $CD8^+$ and $CD4^+$ CD19-CAR T cells, resulting in rapid lymphoma eradication in all treated mice (n=5 or n=4, respectively), whereas mice receiving control T cells showed progressive, deleterious lymphoma (FIG. 5A, B). SB-modified CAR T cells could be detected in the peripheral blood at the peak of response and persisted in the bone marrow of all mice after lymphoma clearance (FIG. 5D). Complete lymphoma eradication from bone marrow was confirmed by flow cytometry (FIG. 5E). Kaplan-Meier analysis showed survival of the entire SB CD19-CAR treatment group at the end of the observation period, equivalent to mice that had been treated with LV-transduced CD19-CAR T cells for comparison (FIG. 5C). Collectively, these data demonstrate that CD19-CAR T cells generated through SB transposition from MC transposon donor vectors are highly potent in vitro and in vivo and mediate equally effective anti-tumor responses as CD19-CAR T cells generated by LV transduction.

Transposon Insertion Site Analysis Reveals a Close-to-Random Genomic Integration Pattern To address issues related to safety, genomic DNA for gene copy number and insertion site analyses was prepared from T cells that had been modified with SB100X mRNA and CD19-CAR MC. An average of n=5 (range 3-8 and 3-11, respectively) CD19-CAR transposon copies in $CD8^+$ T cell clones, and n=6 (range 3-12) transposon copies in $CD4^+$ T cell clones obtained by limiting dilution was found (FIG. 6B, C). Then an insertion site library from polyclonal $CD8^+$ CD19-CAR T cells was constructed for massive parallel sequencing on the Illumina MySeq platform. 26,834 unique insertion sites of the MC-derived CAR transposon were mapped and characterized. A database of LV integration sites in human $CD4^+$ T cells served as a reference and for comparison[Ref. 35]. Analysis of nucleotide frequencies in a 20-kbp window around the transposon insertion sites revealed that transposition from the MC had occurred into regions with close to random nucleotide frequency, while LV insertions were biased towards GC-rich chromosomal segments (FIG. 11 A, B). However, in a smaller, 1.5-kbp window around the insertion sites, both vector systems exhibited a preference for AT-rich DNA (FIG. 11 C, D). The palindromic ATATATAT motif was detected, which contains the TA dinucleotide target sequence of SB adjacent to all of the present MC-derived transposons, similarly to what has been found for transposons mobilized from conventional donor plasmids[Ref. 36] (FIG. 12).

Then it was analyzed whether there was a preference of CD19-CAR transposon insertions into distinct sites of the genome, e.g. exons and introns, genes and cancer related genes. It was found that transpositions from MCs had occurred with only a modest, yet statistically significant (p<0.001) bias towards genic categories; however, in all evaluated categories this preference was substantially smaller than what was found for LV integrations (FIG. 7A).

Importantly, transposon insertions showed only 1.15-fold enrichment in genes and 1.29-fold enrichment in cancer-related genes relative to the expected random frequency, whereas there was a 2.11-fold and 2.64-fold enrichment of LV-associated insertions in these categories, respectively ($p<0.01$ and $p<0.05$). Concordantly, CD19-CAR transposons were also inserted into non-genic regions in a close to random manner (0.89-fold compared to random), while LV transgenes were found to be underrepresented in these regions (0.23-fold compared to random) (FIG. 7A).

Further, it was determined whether there was an association between intragenic transposon insertion frequency and gene expression level. Available transcriptome profiles for activated human T cells[Ref. 37] were used, genes were clustered according to their expression levels into ten groups of equal size and transposon and LV insertions in each group were counted. The data show that MC-derived transposons were integrated into both low and highly-expressed genes in a close to random manner, and only displayed a minute preference for highly-expressed genes (FIG. 7B). In contrast, LV showed a strong preference for integration into highly-expressed genes, and there was an exponential correlation between insertion frequency and expression level of the respective gene ($R^2$ 0.976) (FIG. 7B). The inventors also found a strong enrichment of LV insertions in chromosome regions with H3K36- and H3K79-trimethylation and RNA polymerase II tags, all of them being chromatin marks for highly-expressed genes. LV insertions were underrepresented in transcriptionally-inactive and heterochromatic chromosomal segments, signified by H4K20-, H3K27-, and H3K9-trimethylation (FIG. 13). In contrast, transposon insertions showed only a slight affinity towards markers of active transcription and equally favored integrating into transcriptionally-silenced chromatin domains (FIG. 13). Collectively, these data show that SB transposons mobilized from MCs display a near-random integration pattern in the genome of human T cells, and in contrast to LVs do not have a preference for highly expressed or transcriptionally active genes.

CD19-CAR Transposons Mobilized from MCs are Effectively Integrated into Genomic Safe Harbors Ideally, transposition would occur into genomic regions where insertion of the CAR transgene would not compromise the transcriptional integrity of the gene-modified T cell. Thus, criteria were applied that have been established to define such genomic safe harbors (GSH)[Ref. 38,39] to our insertion site library of MC-modified CD19-CAR T cells, and compared them to the LV insertion site dataset. Computer-generated random positions in the genome map to GSHs at a frequency of 28%. It was found that 20.8% of CD19-CAR transposon insertion sites but only 3% of the LV integration sites satisfied all of the 5 GSH criteria (FIG. 7C). In particular, a significantly higher proportion of transposon insertion sites compared to LV was located >300 kbp outside of cancer related genes (59% vs. 38%) and outside of genes (48% vs. 12%) which constitute the two paramount criteria (FIG. 7C). In the present analysis, none of the SB transposon and LV insertions occurred in known oncogenes[Ref. 39], and no insertion occurred in ultra-conserved genomic regions which constitute only a minor fraction of the genome. In summary, the inventors demonstrated that functional recombinant mammalian cells such as CAR T cells can be generated by transposition such as SB-mediated transposition from MC DNA. MC-derived transposons possess a highly favorable genomic integration profile.

Thus, according to the invention, the enhanced transposition strategy of the invention provides a safety advantage over known viral gene transfer such as LV-based gene transfer.

Example 2: Sleeping Beauty-Mediated Transposition with mRNA-Encoded Hyperactive Sleeping Beauty Transposase 100X (SB100X) and Minicircle DNA-Encoded CD19-CAR Transgenes in Non-Activated T Cells Materials and Methods:

Human Subjects

Peripheral blood was obtained from healthy donors after written informed consent to participate in research protocols approved by the Institutional Review Board of the University of Würzburg.

Construction of Transposon and Lentiviral Vectors

A cassette with EF1/HTLV hybrid promotor, Kozak and eGFP sequence followed by a Stop codon was synthesized (GeneArt) and subcloned into the pT2/HB transposon donor vector (Addgene, #26557). Then, eGFP was replaced with a gene encoding a CD19-CAR (FMC63 targeting domain, IgG4-Fc Hinge spacer, CD3zeta and 4-1BB costimulation) in cis with a T2A element and truncated epidermal growth factor receptor (EGFRt), derived from the previously described lentiviral vector epHIV7[Ref. 27, 28]. The pCMV (CAT)T7-SB100X vector was obtained from Addgene (#34879).

Preparation of Minicircle DNA and SB100X mRNA

MCs encoding eGFP and CD19-CAR_EGFRt transposons, and SB100X were generated from parental pT2 plasmids by PlasmidFactory (Bielefeld) using site-specific recombination and purified by affinity chromatography. Poly (A)-tailed ARCA-capped SB100X mRNA was produced in-house using the mMessage mMachine kit (Ambion), or at EUFETS (Idar-Oberstein).

Generation and In Vitro Analysis of Gene-Modified T-Cells

Peripheral blood mononuclear cells were obtained from peripheral blood of by centrifugation over Ficoll-Hypaque. $CD8^+$ and $CD4^+$ T-cells were purified from PBMC by negative isolation using immunomagnetic beads (Miltenyi). Transfection of SB100X transposase mRNA and CD19-CAR-encoding MC (weight ratio: 4:1) was performed either immediately after isolation or after overnight culture in RPMI-1640 with 10% human serum, glutamin, 100 U/mL penicillin-streptomycin (T-cell medium) and 50 U/mL IL-2. Transfections were performed into $1\times10^6$ T-cells on a 4D-Nucleofector according to the manufacturer's instructions (Lonza). Following transfection, T-cells were propagated in T-cell medium supplemented with 50 U/mL IL-2. Trypan blue staining was performed to quantify viable T-cells. T-cells were stained with the following conjugated mAbs: CD3, CD4, CD8, CD45RA, CD45RO, CD62L; and 7-AAD for live/dead cell discrimination (BD Biosciences). $CAR^+$ (i.e. $EGFRt^+$) T-cells were detected by staining with biotin-conjugated anti-EGFR antibody (ImClone Systems Inc.) and streptavidin-PE. Flow analyses were done on a FACSCanto (BD) and data analyzed using FlowJo software (Treestar). In some experiments, T cells were expanded with irradiated $CD19^+$ feeder cells for 7 days prior to functional testing, and functional analysis performed as described[Ref. 29-31].

Cytotoxicity, Cytokine Secretion, and CFSE Proliferation Assays

Target cells expressing firefly luciferase were incubated in triplicate at $5\times10^3$ cells/well with effector T-cells at various effector to target (E:T) ratios. After a 4-hour incubation luciferin substrate was added to the co-culture and the decrease in luminescence signal in wells that contained target cells and T-cells was measured using a luminometer (Tecan) and compared to target cells alone. Specific lysis was calculated using the standard formula. For analysis of cytokine secretion, $50\times10^3$ T-cells were plated in triplicate wells with target cells at a ratio of 2:1 (Raji and Jeko-1), or 4:1 (K562/CD19 and K562), and IFN-γ and IL-2 production measured by ELISA (Biolegend) in supernatant removed after a 24-hour incubation. For analysis of proliferation, $50\times10^3$ T-cells were labeled with 0.2 μM carboxyfluorescein succinimidyl ester (CFSE, Thermo), washed and plated in triplicate wells with target cells at a ratio of 4:1 (K562/CD19 and K562) in medium without exogenous cytokines. After 72-hour incubation, cells were labeled with anti-CD8/CD4 mAb and 7-AAD to exclude dead cells from analysis. Samples were analyzed by flow cytometry and division of live T-cells assessed by CFSE dilution. The proliferation index was calculated using FlowJo software.

Results:

$CD8^+$ T cells were isolated from PBMC and transfected with SB100X-encoding mRNA and CD19-CAR-encoding MC (weight ratio 4:1). Following transfection, T cells were rested overnight in T-cell medium in the presence of recombinant IL-2 (50 U/ml). T cells were then stimulated with irradiated $CD19^+$ Raji lymphoma cells (effector:target ratio=1:7) and expanded. Control T cells were mock-transfected, rested overnight in the presence of recombinant IL-2 (50 U/ml) and then stimulated with anti-CD3/anti-CD28 beads (Dynal) and expanded. Flow cytometric analysis of EGFRt expression was performed on day 14 after transfection and showed a high rate of stable gene-transfer into T-cells that were transfected with SB100X mRNA and CD19-CAR MC (FIG. 14A), but not mock-transduced T cells (FIG. 14B). Functional analyses confirmed high-level specific cytolytic activity, cytokine secretion (IFN-g, IL-2, TNF-a), and specific productive proliferation of CD19-CAR T cells.

In another experiment, $CD8^+$ T cells were stimulated following transfection with irradiated $CD19^+$ TM EBV-LCL (Epstein-Barr Virus-transformed lymphoblastoid cell lines) instead of Raji lymphoma cells (effector:target ratio=1:7) and expanded. Flow cytometric analysis of EGFRt expression on day 14 after nucleofection showed a high rate of stable CD19-CAR gene-transfer (FIG. 15A). Functional analyses confirmed that CD19-CAR T cells conferred high-level specific cytolytic activity against $CD19^+$ target cells (FIG. 15B), produced cytokines and underwent productive proliferation after stimulation with $CD19^+$ target cells.

In another experiment, $CD8^+$ T cells were maintained following transfection in T-cell medium that had been supplemented with 50 U/mL IL-2. Flow cytometric analysis of EGFRt expression performed on day 14 after nucleofection showed a high rate of stable CD19-CAR gene-transfer (FIG. 16A). Functional analyses confirmed high-level specific cytolytic activity (FIG. 16B), cytokine secretion (IFN-g, IL-2, TNF-a), and specific productive proliferation of CD19-CAR T cells after stimulation with $CD19^+$ target cells.

Example 3: Sleeping Beauty-Mediated Transposition with Minicircle DNA-Encoded Hyperactive Sleeping Beauty Transposase 100X (SB100X) and Minicircle DNA-Encoded CD19-CAR Transgenes in Non-Activated T Cells Materials and Methods:

Human Subjects

Peripheral blood was obtained from healthy donors after written informed consent to participate in research protocols approved by the Institutional Review Board of the University of Würzburg.

Construction of Transposon and Lentiviral Vectors

A cassette with EF1/HTLV hybrid promotor, Kozak and eGFP sequence followed by a Stop codon was synthesized (GeneArt) and subcloned into the pT2/HB transposon donor vector (Addgene, #26557). Then, eGFP was replaced with a gene encoding a CD19-CAR (FMC63 targeting domain, IgG4-Fc Hinge spacer, CD3zeta and 4-1BB costimulation) in cis with a T2A element and truncated epidermal growth factor receptor (EGFRt), derived from the previously described lentiviral vector epHIV7[Ref. 27, 28]. The pCMV (CAT)T7-SB100X vector was obtained from Addgene (#34879).

Preparation of Minicircle DNA and SB100X mRNA

MCs encoding eGFP and CD19-CAR_EGFRt transposons, and SB100X were generated from parental pT2 plasmids by PlasmidFactory (Bielefeld) using site-specific recombination and purified by affinity chromatography.

Generation and In Vitro Analysis of Gene-Modified T-Cells

Peripheral blood mononuclear cells were obtained from peripheral blood of by centrifugation over Ficoll-Hypaque. $CD8^+$ and $CD4^+$ T-cells were purified from PBMC by negative isolation using immunomagnetic beads (Miltenyi). Transfection of transposase and transposon donor MC vectors was performed either immediately after isolation or after overnight culture in RPMI-1640 with 10% human serum, glutamin, 100 U/mL penicillin-streptomycin and 50 U/mL IL-2. Transfections were performed into $1\times10^6$ T-cells on a 4D-Nucleofector according to the manufacturer's instructions (Lonza). Following nucleofection, T-cells were propagated in RPMI-1640 with 10% human serum, glutamin, 100 U/mL penicillin-streptomycin and 50 U/mL IL-2. Trypan blue staining was performed to quantify viable T-cells. T-cells were stained with the following conjugated mAbs: CD3, CD4, CD8, CD45RA, CD45RO, CD62L; and 7-AAD for live/dead cell discrimination (BD Biosciences). $CAR^+$ (i.e. $EGFRt^+$) T-cells were detected by staining with biotin-conjugated anti-EGFR antibody (ImClone Systems Inc.) and streptavidin-PE. Flow analyses were done on a FACSCanto (BD) and data analyzed using FlowJo software (Treestar). In some experiments, T cells were expanded with irradiated $CD19^+$ feeder cells for 7 days prior to functional testing, and functional analysis of CAR T-cells performed as described[Ref. 29-31].

Cytotoxicity, Cytokine Secretion, and CFSE Proliferation Assays

Target cells expressing firefly luciferase were incubated in triplicate at $5\times10^3$ cells/well with effector T-cells at various effector to target (E:T) ratios. After a 4-hour incubation, luciferin substrate was added to the co-culture and the decrease in luminescence signal in wells that contained target cells and T-cells was measured using a luminometer (Tecan) and compared to target cells alone. Specific lysis was calculated using the standard formula[Ref. 2]. For analysis of cytokine secretion, $50\times10^3$ T-cells were plated in triplicate wells with target cells at a ratio of 2:1 (Raji and Jeko-1), or 4:1 (K562/CD19 and K562), and IFN-γ and IL-2 production measured by ELISA (Biolegend) in supernatant removed after a 24-hour incubation. For analysis of proliferation, $50\times10^3$ T-cells were labeled with 0.2 μM carboxyfluorescein succinimidyl ester (CFSE, Thermo), washed and plated in triplicate wells with target cells at a ratio of 4:1 (K562/CD19 and K562) in medium without exogenous cytokines. After 72-hour incubation, cells were labeled with anti-CD8/CD4 mAb and 7-AAD to exclude dead cells from analysis. Samples were analyzed by flow cytometry and division of live T-cells assessed by CFSE dilution. The proliferation index was calculated using FlowJo software.

Results:

$CD4^+$ and $CD8^+$ T cells were isolated from PBMC and transfected ($CD4^+$ and $CD8^+$ T cells separately) with SB100X-encoding MC and CD19-CAR-encoding MC. Following transfection, T cells were rested overnight in T-cell medium that was supplemented with 50 U/mL IL-2. T cells were then stimulated with anti-CD3/anti-CD28 beads and expanded. Control T cells were mock-transfected, rested overnight in T-cell medium that was supplemented with 50 U/mL IL-2, then stimulated with anti-CD3/anti-CD28 beads and expanded. Flow cytometric analysis of EGFRt expression was performed on day 14 after transfection and showed a high rate of stable gene-transfer into T cells that were transfected with SB100X MC and CD19-CAR MC (FIG. 17A, B), but not mock-transduced T cells. In functional experiments, CD19-CAR transduced T cells conferred specific high-level lysis of CD19+ target cells (FIG. 17C), produced cytokines and underwent productive proliferation after stimulation with $CD19^+$ target cells.

Example 4: Sleeping Beauty-Mediated Transposition with Minicircle DNA-Encoded Hyperactive Sleeping Beauty Transposase 100X (SB100X) and Minicircle DNA-Encoded CD19-CAR Transgenes in T Cells Using a Conventional Electroporator Materials and Methods:

Human Subjects

Peripheral blood was obtained from healthy donors after written informed consent to participate in research protocols approved by the Institutional Review Board of the University of Würzburg.

Construction of Transposon and Lentiviral Vectors

A cassette with EF1/HTLV hybrid promotor, Kozak and eGFP sequence followed by a Stop codon was synthesized (GeneArt) and subcloned into the pT2/HB transposon donor vector (Addgene, #26557). Then, eGFP was replaced with a gene encoding a CD19-CAR (FMC63 targeting domain, IgG4-Fc Hinge spacer, CD3zeta and 4-1BB costimulation) in cis with a T2A element and truncated epidermal growth factor receptor (EGFRt), derived from the previously described lentiviral vector epHIV7[Ref. 27, 28]. The pCMV (CAT)T7-SB100X vector was obtained from Addgene (#34879).

Preparation of Minicircle DNA

MCs encoding eGFP and CD19-CAR_EGFRt transposons, and SB100X were generated from parental pT2 plasmids by Plasmid Factory (Bielefeld) using site-specific recombination and purified by affinity chromatography.

Generation and In Vitro Analysis of Gene-Modified T-Cells

Peripheral blood mononuclear cells were obtained from peripheral blood of by centrifugation over Ficoll-Hypaque. $CD8^+$ T-cells were purified from PBMC by negative isolation using immunomagnetic beads (Miltenyi). T cells were activated with anti-CD3/anti-CD28 beads (Dynal) for 2 days. Transfection of transposon and transposase MC vectors was performed using the Agile Pulse MAX System according to the manufacturer's instructions (BTX). Following electroporation, T cells were maintained in T-cell medium supplemented with 50 U/ml IL-2 overnight and then stimulated with anti-CD3/anti-CD28 beads (Dynal). Trypan blue staining was performed to quantify viable T-cells. T-cells were stained with the following conjugated mAbs: CD3, CD4, CD8, CD45RA, CD45RO, CD62L; and 7-AAD for live/dead cell discrimination (BD Biosciences). $CAR^+$ (i.e. $EGFRt^+$) T-cells were detected by staining with biotin-conjugated anti-EGFR antibody (ImClone Systems Inc.) and streptavidin-PE. Flow analyses were done on day 14 after electroporation on a FACSCanto (BD) and data analyzed using FlowJo software (Treestar).

Cytotoxicity, Cytokine Secretion, and CFSE Proliferation Assays

Target cells expressing firefly luciferase were incubated in triplicate at $5\times10^3$ cells/well with effector T-cells at various effector to target (E:T) ratios. After a 4-hour incubation, luciferin substrate was added to the co-culture and the decrease in luminescence signal in wells that contained target cells and T-cells was measured using a luminometer (Tecan) and compared to target cells alone. Specific lysis was calculated using the standard formula[Ref. 2]. For analysis of cytokine secretion, $50\times10^3$ T-cells were plated in triplicate wells with target cells at a ratio of 2:1 (Raji and Jeko-1), or 4:1 (K562/CD19 and K562), and IFN-γ and IL-2 production measured by ELISA (Biolegend) in supernatant removed after a 24-hour incubation. For analysis of proliferation, $50\times10^3$ T-cells were labeled with 0.2 μM carboxyfluorescein succinimidyl ester (CFSE, Thermo), washed and plated in triplicate wells with target cells at a ratio of 4:1 (K562/CD19 and K562) in medium without exogenous cytokines. After 72-hour incubation, cells were labeled with anti-CD8/CD4 mAb and 7-AAD to exclude dead cells from analysis. Samples were analyzed by flow cytometry and division of live T-cells assessed by CFSE dilution. The proliferation index was calculated using FlowJo software.

Results:

$CD8^+$ T cells were isolated from PBMC. In one example, 3.5x10e6 $CD8^+$ T cells respectively were electroporated in a 4 mm cuvette (volume: 100 μL) with 4 μg of SB100X-encoding MC and 4 μg of CD19-CAR-encoding MC (ratio 1:1). Electroporation was performed using 2 pulses, each with a 1200 V amplitude, a pulse duration of 0.1 milliseconds (ms), and a pulse interval of 0.2 ms. Following electroporation, T cells were rested overnight in T-cell medium that had been supplemented with IL-2 (50 U/ml). T cells were then stimulated with anti-CD3/anti-CD28 beads and expanded. Control T cells were mock-transfected, rested overnight in the presence of recombinant IL-2, and then stimulated with anti-CD3/anti-CD28 beads and expanded. Flow cytometric analysis of EGFRt expression was performed on day 14 after transfection and showed a high rate of stable gene-transfer into T cells that were transfected with SB100X MC and CD19-CAR MC (FIG. 18), but not mock-transduced T cells. In functional experiments, CD19-CAR transduced T cells conferred specific high-level lysis of CD19+ target cells, produced cytokines and underwent productive proliferation after stimulation with $CD19^+$ target cells.

Example 5: Titration of Transposon Copy Number in the Genome of T Cells After Sleeping Beauty-Mediated Transposition Materials and Methods:

Human Subjects

Peripheral blood was obtained from healthy donors after written informed consent to participate in research protocols approved by the Institutional Review Board of the University of Würzburg.

Construction of Transposon and Lentiviral Vectors

A cassette with EF1/HTLV hybrid promotor, Kozak and eGFP sequence followed by a Stop codon was synthesized (GeneArt) and subcloned into the pT2/HB transposon donor vector (Addgene, #26557). Then, eGFP was replaced with a gene encoding a CD19-CAR (FMC63 targeting domain, IgG4-Fc Hinge spacer, CD3zeta and 4-1BB costimulation) in cis with a T2A element and truncated epidermal growth factor receptor (EGFRt), derived from the previously described lentiviral vector epHIV7[Ref. 27, 28]. The pCMV (CAT)T7-SB100X vector was obtained from Addgene (#34879).

Preparation of Minicircle DNA

MCs encoding eGFP and CD19-CAR_EGFRt transposons, and SB100X were generated from parental pT2 plasmids by PlasmidFactory (Bielefeld) using site-specific recombination and purified by affinity chromatography.

Generation and In Vitro Analysis of Gene-Modified T-Cells

Peripheral blood mononuclear cells were obtained from peripheral blood of by centrifugation over Ficoll-Hypaque. $CD8^+$ and $CD4^+$ T-cells were purified from PBMC by negative isolation using immunomagnetic beads (Miltenyi) and stimulated with anti-CD3/anti-CD28 beads (Dynal). Transfection of transposase and transposon minicircle vectors was performed on day 2. Transfections were performed into $1\times10^6$ T-cells on a 4D-Nucleofector according to the manufacturer's instructions (Lonza). Following nucleofection, T-cells were propagated in RPMI-1640 with 10% human serum, glutamin, 100 U/mL penicillin-streptomycin and 50 U/mL IL-2. Trypan blue staining was performed to quantify viable T-cells. T-cells were stained with the following conjugated mAbs: CD3, CD4, CD8, CD45RA, CD45RO, CD62L; and 7-AAD for live/dead cell discrimination (BD Biosciences). $CAR^+$ (i.e. $EGFRt^+$) T-cells were detected by staining with biotin-conjugated anti-EGFR antibody (ImClone Systems Inc.) and streptavidin-PE. Flow analyses were done on a FACSCanto (BD) and data analyzed using FlowJo software (Treestar). In some experiments, T cells were expanded with irradiated $CD19^+$ feeder cells for 7 days prior to functional testing, and functional analysis of CAR T-cells performed as described[Ref. 29-31].

Droplet Digital PCR

Prior to droplet digital PCR (ddPCR), 300 ng of samples were digested with 1 μL the enzyme DpnI (20,000 U/mL) that cleaves only methylated, non-integrated vectors in 3 μL of NEB 3.1 buffer at a final volume of 30 μL at 37° C. DpnI digested samples were then fragmented with 1 μL of CviQI (10,000 U/mL), adding 0.5 μL of NEB 3.1 Buffer and 3.5 μL of $H_2O$, giving a final volume of 35 μL for 2 hours at 25° C.

For droplet generation, primers (600 nM), probes (200 nM) and digested template (17 ng of each) were added to the ready-to-used ddPCR Supermix (Bio-Rad) at the final volume of 25 μL at room temperature. 20 μL of the PCR mixture was added to a specific well in a DG8 Cartridges. Then 70 μL of Droplet Generation Oil was added to each well and incubated for 2 min at room temperature. Wells were covered and put in a QX100 Droplet Generator. After a couple of minutes, approximately 20,000 droplets were generated per well. 40 μL of generated droplets were transferred into a 96-well PCR plate and sealed with a single sealing foil in the PX1 PCR Plate Sealer (Bio-Rad). The PCR reaction was performed in a cycler with 2° C./sec ramp rate using following conditions: 95° C. 10 min, 94° C. 30 s, 40 cycles of: 60° C. 60 s, 98° C. 10 min.

Fluorescence measurements for each droplet was performed by a QX100 Droplet Reader, whereas ribonuclease P/MRP 30 subunit (RPP30) was used as the copy number reference (2 copies per genome). Analysis was performed using QuantaSoft software. The following Primers and oligos used for droplet digital PCR copy number analysis:

| Primer name | Sequence (5'→3') |
|---|---|
| CAR-Fwd | ATCTGGATGTCGGGGATCAG (SEQ ID NO: 16) |
| CAR-probe | FAM-AGCAGCATGGTGGCGGCGCT-BH1 (SEQ ID NO: 17) |
| CAR-Rev | GCTTGCTCAACTCTACGTCT (SEQ ID NO: 18) |
| MC-Fwd | CCGACCTTAATGCGCCTC (SEQ ID NO: 19) |
| MC-probe | FAM-GCGCTGTAGCCTCACGCCCACATATGT-BH1 (SEQ ID NO: 20) |
| MC-Rev | AGGATTAAATGTCAGGAATTGTGAA (SEQ ID NO: 21) |
| RPP30-Fwd | GGTTAACTACAGCTCCCAGC (SEQ ID NO: 22) |
| RPP30-probe | HEX-TGGACCTGCGAGCGGGTTCTGACC-BH1 (SEQ ID NO: 23) |
| RPP30-Rev | CTGTCTCCACAAGTCCGC (SEQ ID NO: 24) |

Results:

Transfections were performed using SB100X-encoding MC and CD19-CAR-encoding MC. We titrated the amount of SB100X MC and CD19-CAR MC vectors that were transfected into T cells to determine the influence on gene-transfer rate and gene-copy number (i.e. transposon copy number) in the genome of T cells. We used serial dilutions of SB100X MC and CD19-CAR MC (2-fold serial dilutions, with SB100X MC DNA ranging from 500 ng to 31 ng, and CD19-CAR MC DNA ranging from 600 ng to 37.5 ng) (FIG. 19A). On day 14 after transfection, the percentage of gene-modified T cells was determined by flow cytometry using the EGFRt marker (FIG. 19B). We found higher gene transfer rates when higher amounts of MC vectors were transfected, and lower gene transfer rates when lower amounts of MC vectors were transfected (FIG. 19A, B). Also, we found higher levels of MFI by flow cytometry for expression of the EGFRt marker when higher amounts of MC vectors were transfected, and lower levels of MFI by flow cytometry when lower amounts of MC vectors were transfected (FIG. 19A, B).

We then FACS-sorted $EGFRt^+$ T cells to a purity of >90% using a gating strategy that included all $EGFRt^+$ T cells (low, intermediate and high EGFRt expressers), and isolated genomic DNA for subsequent copy number analysis using ddPCR. We found a correlation between the amount of MC DNA vector that had been transfected and the CD19-CAR transposon copy number, i.e. when higher amounts of MC vectors were transfected, a higher transposon copy number was obtained, and when lower amounts of MC vectors were transfected, a lower transposon copy number was obtained (FIG. 19C). The average transposon copy number in the genome of T cells was 11.3 when 500 ng of SB100X MC DNA and 600 ng of CD19-CAR MC DNA vectors were transfected. The average transposon copy number in the genome of T cells decreased to 2.8 when 31 ng of SB100X MC DNA and 37.5 ng of CD19-CAR MC DNA of MC-DNA vectors were transfected (FIG. 19C).

In summary, these data demonstrate that the amount of MC-encoded SB100X and MC-encoded CD19-CAR that is transfected into T cells can be titrated to obtain a desired gene-transfer rate, a desired transgene expression level and a desired gene copy number. This is useful to fine-tune the gene copy number (i.e. transposon copy number) to a desired number—e.g. to lower the gene copy number to reduce the number of genomic insertions, and thus the risk for genotoxicity and insertional mutagenesis; to increase the gene copy number to increase the level of transgene expression; to lower or increase transgene expression to obtain optimal functional output—e.g. to lower or increase CAR expression to obtain optimal functional output of CAR-modified T cells.

Example 6: Sleeping Beauty-Mediated Gene Transfer into Leukocyte Subsets Other than CD4$^+$ Helper and CD8$^+$ Killer T Cells Using MC Transposons Materials and Methods:

Human Subjects

Peripheral blood was obtained from healthy donors after written informed consent to participate in research protocols approved by the Institutional Review Board of the University of Würzburg.

Construction of Transposon and Lentiviral Vectors

A cassette with EF1/HTLV hybrid promotor, Kozak and eGFP sequence followed by a Stop codon was synthesized (GeneArt) and subcloned into the pT2/HB transposon donor vector (Addgene, #26557). Then, eGFP was replaced with a gene encoding a CD19-CAR (FMC63 targeting domain, IgG4-Fc Hinge spacer, CD3zeta and 4-1BB costimulation) in cis with a T2A element and truncated epidermal growth factor receptor (EGFRt), derived from the previously described lentiviral vector epHIV7[Ref. 27, 28]. The pCMV (CAT)T7-SB100X vector was obtained from Addgene (#34879).

Preparation of Minicircle DNA

MCs encoding eGFP and CD19-CAR_EGFRt transposons, and SB100X were generated from parental pT2 plasmids by PlasmidFactory (Bielefeld) using site-specific recombination and purified by affinity chromatography.

Generation and In Vitro Analysis of Gene-Modified Leukocytes

Peripheral blood mononuclear cells were obtained from peripheral blood of by centrifugation over Ficoll-Hypaque and transfection of transposase and transposon minicircle vectors performed after overnight culture in RPMI-1640 with 10% human serum, glutamin, 100 U/mL penicillin-streptomycin and supplemented with 50 U/mL IL-2 and zoledronate to a final concentration of 5 μM. Transfections were performed into $10\times10^6$ PBMC on a 4D-Nucleofector according to the manufacturer's instructions (Lonza). Following nucleofection, PBMC were propagated in RPMI-1640 with 10% human serum, glutamin, 100 U/mL penicillin-streptomycin, 50 U/mL IL-2 and zoledronate (f.c. 5 μM). On day 9 after transfection, trypan blue staining was performed to quantify viable cells and staining performed with the following conjugated mAbs: Vγ9Vδ2, CD3, CD4, CD8, CD19, CD45RA, CD45RO, CD56, CD62L; and 7-AAD for live/dead cell discrimination (BD Biosciences). CAR$^+$ (i.e. EGFRt$^+$) cells were detected by staining with biotin-conjugated anti-EGFR antibody (ImClone Systems Inc.) and streptavidin-PE. Flow analyses were done on a FACSCanto (BD) and data analyzed using FlowJo software (Treestar). In some experiments, T cells were isolated using immunomagnetic beads and expanded with irradiated CD19$^+$ feeder cells prior to functional testing, and functional analysis of CAR T-cells performed as described[Ref. 29-31].

Results:

Transfection of SB100X MC and CD19-CAR MC was performed into bulk PBMC. IL-2 was added to the culture medium to support expansion of T cell, NKT cells and NK cells. Zoledronate was added to the culture medium to support expansion of γδ (gamma delta) T cells. Flow cytometric analysis of EGFRt expression was performed on day 9 after transfection and showed a high rate of stable gene-transfer into Vγ9Vδ2 γδ T cells (FIG. 20A). γδ T cells were then stimulated with CD19+ EBV-LCL (Epstein-Barr Virus transformed lymphoblastoid cell lines) and propagated in T-cell medium that was supplemented with IL-2 and Zoledronate. At the end of the expansion cycle, flow cytometric analysis of EGFRt expression was performed and showed that the percentage of CD19-CAR expressing γδ T cells had further increased (FIG. 20B). Specific recognition of CD19+ target cells by CD19-CAR modified γδ T cells was confirmed in cytotoxicity assays and cytokine secretion assays (FIG. 20C, D). In another experiment, transfection of SB100X MC and CD19-CAR MC was performed into bulk PBMC and IL-2 was added to the culture medium to support expansion of T cell, NKT cells and NK cells, and Zoledronate was added to the culture medium to support expansion of γδ (gamma delta) T cells. Flow cytometric analysis of EGFRt expression was performed on day 9 after transfection and showed a high rate of stable gene-transfer into Vγ9Vδ2 γδ T cells (CD3+ Vγ9Vδ2+), NKT cells (CD3+, CD56+), NK cells (CD3−, CD56+), and B cells (CD3−, CD19+) (FIG. 21).

REFERENCES

1. Davila M L, Riviere I, Wang X, et al. Efficacy and toxicity management of 19-28z CAR T cell therapy in B cell acute lymphoblastic leukemia. *Sci Transl Med.* 2014; 6(224):224ra225.
2. Maude S L, Frey N, Shaw P A, et al. Chimeric antigen receptor T cells for sustained remissions in leukemia. *N Engl J Med.* 2014; 371(16):1507-1517.
3. Kochenderfer J N, Dudley M E, Kassim S H, et al. Chemotherapy-refractory diffuse large B-cell lymphoma and indolent B-cell malignancies can be effectively treated with autologous T cells expressing an anti-CD19 chimeric antigen receptor. *J Clin Oncol.* 2015; 33(6):540-549.
4. Izsvak Z, Hackett P B, Cooper L J, Ivies Z. Translating Sleeping Beauty transposition into cellular therapies: victories and challenges. *Bioessays.* 2010; 32(9):756-767.
5. Ivies Z, Izsvak Z. Nonviral gene delivery with the sleeping beauty transposon system. *Hum Gene Ther.* 2011; 22(9):1043-1051.
6. Aronovich E L, McIvor R S, Hackett P B. The Sleeping Beauty transposon system: a non-viral vector for gene therapy. *Hum Mol Genet.* 2011; 20(R1):R14-20.
7. Swierczek M, Izsvak Z, Ivies Z. The Sleeping Beauty transposon system for clinical applications. *Expert Opin Biol Ther.* 2012; 12(2):139-153.

8. Ivies Z, Hackett P B, Plasterk R H, Izsvak Z. Molecular reconstruction of Sleeping Beauty, a Tc1-like transposon from fish, and its transposition in human cells. *Cell.* 1997; 91(4):501-510.

9. Mates L, Chuah M K, Belay E, et al. Molecular evolution of a novel hyperactive Sleeping Beauty transposase enables robust stable gene transfer in vertebrates. *Nat Genet.* 2009; 41(6):753-761.

10. Peng P D, Cohen C J, Yang S, et al. Efficient nonviral Sleeping Beauty transposon-based TCR gene transfer to peripheral blood lymphocytes confers antigen-specific antitumor reactivity. *Gene Ther.* 2009; 16(8):1042-1049.

11. Field A C, Vink C, Gabriel R, et al. Comparison of lentiviral and sleeping beauty mediated alphabeta T cell receptor gene transfer. *PLoS One.* 2013; 8(6):e68201.

12. Huang X, Guo H, Kang J, et al. Sleeping Beauty transposon-mediated engineering of human primary T cells for therapy of CD19+ lymphoid malignancies. *Mol Ther.* 2008; 16(3):580-589.

13. Jin Z, Maiti S, Huls H, et al. The hyperactive Sleeping Beauty transposase SB100X improves the genetic modification of T cells to express a chimeric antigen receptor. *Gene Ther.* 2011; 18(9):849-856.

14. Singh H, Manuri P R, Olivares S, et al. Redirecting specificity of T-cell populations for CD19 using the Sleeping Beauty system. *Cancer Res.* 2008; 68(8): 2961-2971.

15. Singh H, Huls H, Kebriaei P, Cooper L J. A new approach to gene therapy using Sleeping Beauty to genetically modify clinical-grade T cells to target CD19. *Immunol Rev.* 2014; 257(1):181-190.

16. Singh H, Figliola M J, Dawson M J, et al. Manufacture of clinical-grade CD19-specific T cells stably expressing chimeric antigen receptor using Sleeping Beauty system and artificial antigen presenting cells. *PLoS One.* 2013; 8(5):e64138.

17. June C H, Riddell S R, Schumacher T N. Adoptive cellular therapy: a race to the finish line. *Sci Transl Med.* 2015; 7(280):280ps287.

18. Ramos C A, Savoldo B, Dotti G. CD19-CAR trials. *Cancer J.* 2014; 20(2):112-118.

19. Mayrhofer P, Schleef M, Jechlinger W. Use of minicircle plasmids for gene therapy. *Methods Mol Biol.* 2009; 542:87-104.

20. Chen Z Y, He C Y, Ehrhardt A, Kay M A. Minicircle DNA vectors devoid of bacterial DNA result in persistent and high-level transgene expression in vivo. *Mol Ther.* 2003; 8(3):495-500.

21. Kay M A, He C Y, Chen Z Y. A robust system for production of minicircle DNA vectors. *Nat Biotechnol.* 2010; 28(12):1287-1289.

22. Mayrhofer P, Blaesen M, Schleef M, Jechlinger W. Minicircle-DNA production by site specific recombination and protein-DNA interaction chromatography. *J Gene Med.* 2008; 10(11):1253-1269.

23. Chabot S, Orio J, Schmeer M, Schleef M, Golzio M, Teissie J. Minicircle DNA electrotransfer for efficient tissue-targeted gene delivery. *Gene Ther.* 2013; 20(1): 62-68.

24. Kobelt D, Schleef M, Schmeer M, Aumann J, Schlag P M, Walther W. Performance of high quality minicircle DNA for in vitro and in vivo gene transfer. *Mol Biotechnol.* 2013; 53(1):80-89.

25. Sharma N, Cai Y, Bak R O, Jakobsen M R, Schroder L D, Mikkelsen J G. Efficient sleeping beauty DNA transposition from DNA minicircles. *Mol Ther Nucleic Acids.* 2013; 2:e74.

26. Cui Z, Geurts A M, Liu G, Kaufman C D, Hackett P B. Structure-function analysis of the inverted terminal repeats of the sleeping beauty transposon. *J Mol Biol.* 2002; 318(5):1221-1235.

27. Hudecek M, Sommermeyer D, Kosasih P L, et al. The nonsignaling extracellular spacer domain of chimeric antigen receptors is decisive for in vivo antitumor activity. *Cancer Immunol Res.* 2015; 3(2):125-135.

28. Wang X, Chang W C, Wong C W, et al. A transgene-encoded cell surface polypeptide for selection, in vivo tracking, and ablation of engineered cells. *Blood.* 2011; 118(5):1255-1263.

29. Hudecek M, Lupo-Stanghellini M T, Kosasih F L, et al. Receptor affinity and extracellular domain modifications affect tumor recognition by ROR1-specific chimeric antigen receptor T cells. *Clin Cancer Res.* 2013; 19(12):3153-3164.

30. Hudecek M, Schmitt T M, Baskar S, et al. The B-cell tumor-associated antigen ROR1 can be targeted with T cells modified to express a ROR1-specific chimeric antigen receptor. *Blood.* 2010; 116(22):4532-4541.

31. Brown C E, Wright C L, Naranjo A, et al. Biophotonic cytotoxicity assay for high-throughput screening of cytolytic killing. *J Immunol Methods.* 2005; 297(1-2): 39-52.

32. Sommermeyer D, Hudecek M, Kosasih P L, et al. Chimeric antigen receptor-modified T cells derived from defined CD8 and CD4 subsets confer superior antitumor reactivity in vivo. *Leukemia.* 2015.

33. Frigault M J, Lee J, Basil M C, et al. identification of chimeric antigen receptors that mediate constitutive or inducible proliferation of T cells. *Cancer Immunol Res.* 2015; 3(4):356-367.

34. Zayed H, Izsvak Z, Walisko O, Ivies Z. Development of hyperactive sleeping beauty transposon vectors by mutational analysis. *Mol Ther.* 2004; 9(2):292-304.

35. Wang G P, Levine B L, Binder G K, et al. Analysis of lentiviral vector integration in HIV+ study subjects receiving autologous infusions of gene modified CD4+ T cells. *Mol Ther.* 2009; 17(5):844-850.

36. Vigdal T J, Kaufman C D, Izsvak Z, Voytas D F, Ivics Z. Common physical properties of DNA affecting target site selection of sleeping beauty and other Tc1/mariner transposable elements. *J Mol Biol.* 2002; 323(3):441-452.

37. Schones D E, Cui K, Cuddapah S, et al. Dynamic regulation of nucleosome positioning in the human genome. *Cell.* 2008; 132(5):887-898.

38. Papapetrou E P, Lee G, Malani N, et al. Genomic safe harbors permit high beta-globin transgene expression in thalassemia induced pluripotent stem cells. *Nat Biotechnol.* 2011; 29(1):73-78.

39. Sadelain M, Papapetrou E P, Bushman F D. Safe harbours for the integration of new DNA in the human genome. *Nat Rev Cancer.* 2012; 12(1):51-58.

40. Izsvak Z, Ivics Z, Plasterk R H. Sleeping Beauty, a wide host-range transposon vector for genetic transformation in vertebrates. *J Mol Biol.* 2000; 302(1):93-102.

41. Lukacs G L, Haggie P, Seksek O, Lechardeur D, Freedman N, Verkman A S. Size-dependent DNA mobility in cytoplasm and nucleus. *J Biol Chem.* 2000; 275(3):1625-1629.

42. Wilber A, Frandsen J L, Geurts J L, Largaespada D A, Hackett P B, McIvor R S. RNA as a source of transposase for Sleeping Beauty-mediated gene insertion and expression in somatic cells and tissues. *Mol Ther.* 2006; 13(3):625-630.

43. Hacein-Bey-Abina S, Von Kalle C, Schmidt M, et al. LMO2-associated clonal T cell proliferation in two patients after gene therapy for SCID-X1. *Science.* 2003; 302(5644):415-419.

44. Yant S R, Wu X, Huang Y, Garrison B, Burgess S M, Kay M A. High-resolution genome-wide mapping of transposon integration in mammals. *Mol Cell Biol.* 2005; 25(6):2085-2094.

45. de Jong J, Akhtar W, Badhai J, et al. Chromatin landscapes of retroviral and transposon integration profiles. *PLoS Genet.* 2014; 10(4):e1004250.

46. Grabundzija I, Irgang M, Mates L, et al. Comparative analysis of transposable element vector systems in human cells. *Mol Ther.* 2010; 18(6):1200-1209.

47. Huang X, Guo H, Tammana S, et al. Gene transfer efficiency and genome-wide integration profiling of Sleeping Beauty, Tol2, and piggyBac transposons in human primary T cells. *Mol Ther.* 2010; 18(10):1803-1813.

48. Maldarelli F, Wu X, Su L, et al. HIV latency. Specific HIV integration sites are linked to clonal expansion and persistence of infected cells. *Science.* 2014; 345(6193):179-183.

49. Voigt K, Gogol-Doring A, Miskey C, et al. Retargeting sleeping beauty transposon insertions by engineered zinc finger DNA-binding domains. *Mol Ther.* 2012; 20(10):1852-1862.

50. Ivies Z, Katzer A, Stuwe E E, Fiedler D, Knespel S, Izsvak Z. Targeted Sleeping Beauty transposition in human cells. *Mol Ther.* 2007; 15(6):1137-1144.

51. Morgan M, Anders S, Lawrence M, Aboyoun P, Pages H, Gentleman R. ShortRead: a bioconductor package for input, quality assessment and exploration of high-throughput sequence data. *Bioinformatics.* 2009; 25(19):2607-2608.

52. Langmead B, Trapnell C, Pop M, Salzberg S L. Ultrafast and memory-efficient alignment of short DNA sequences to the human genome. *Genome Biol.* 2009; 10(3):R25.

53. Quinlan A R, Hall I M. BEDTools: a flexible suite of utilities for comparing genomic features. *Bioinformatics.* 2010; 26(6):841-842.

54. Barski A, Cuddapah S, Cui K, et al. High-resolution profiling of histone methylations in the human genome. *Cell.* 2007; 129(4):823-837.

55. Zhang Y, Liu T, Meyer C A, et al. Model-based analysis of ChIP-Seq (MACS). *Genome Biol.* 2008; 9(9):R137.

56. Bejerano G, Pheasant M, Makunin I, et al. Ultraconserved elements in the human genome. *Science.* 2004; 304(5675):1321-1325.

57. Monjezi R, Miskey C, Gogishvili G, et al. Enhanced CAR T-cell engineering using non-viral Sleeping Beauty transposition from minicircle vectors. *Leukemia.* 2016 Aug. 5, DOI: 10.1038/leu.2016.180.

SEQUENCE LISTING

```
<110>  Julius-Maximilians-Universität Würzburg

<120>  A method for high level and stable gene transfer in lymphocytes

<130>  192305

<150>  EP 15002732.4

<151>  2015-09-22

<150>  EP 16153490.4

<151>  2016-01-29

<160>  24

<170>  PatentIn version 3.5

<210>  1

<211>  36

<212>  DNA

<213>  Artificial Sequence

<220>

<223>  L(+) primer

<400>  1

gtaatacgac tcactatagg gctccgctta agggac            36

<210>  2

<211>  17

<212>  DNA
```

-continued

SEQUENCE LISTING

<213> Artificial Sequence

<220>

<223> L(-)FspBI primer

<220>

<221> misc_feature

<222> (17)..(17)

<223> n is g-AMINO

<400> 2
tagtccctta agcggan 17

<210> 3

<211> 19

<212> DNA

<213> Artificial Sequence

<220>

<223> Nested primer

<400> 3
agggctccgc ttaagggac 19

<210> 4

<211> 22

<212> DNA

<213> Artificial Sequence

<220>

<223> Linker primer

<400> 4
gtaatacgac tcactatagg gc 22

<210> 5

<211> 27

<212> DNA

<213> Artificial Sequence

<220>

<223> T_Bal rev primer

<400> 5
gaattgtgat acagtgaatt ataagtg 27

<210> 6

<211> 27

<212> DNA

<213> Artificial Sequence

<220>

<223> T_Bal primer

-continued

SEQUENCE LISTING

<400> 6
cttgtgtcat gcacaaagta gatgtcc 27

<210> 7

<211> 36

<212> DNA

<213> Artificial Sequence

<220>

<223> T_Bal_long primer

<400> 7
cttgtgtcat gcacaaagta gatgtcctaa ctgact 36

<210> 8

<211> 25

<212> DNA

<213> Artificial Sequence

<220>

<223> LAM_SB_50 primer

<400> 8
agttttaatg actccaactt aagtg 25

<210> 9

<211> 89

<212> DNA

<213> Artificial Sequence

<220>

<223> SB20h-bc-ill-N primer

<220>

<221> misc_feature

<222> (59)..(64)

<223> nnnnnn is a TRUSEQ-ILLUMINA-INDEX barcode DNA sequence

<400> 9
aatgatacgg cgaccaccga gatctacact ctttccctac acgacgctct tccgatctnn 60
nnnncttaag tgtatgtaaa cttccgact 89

<210> 10

<211> 64

<212> DNA

<213> Artificial Sequence

<220>

<223> PE-nest-ind1-N primer

<220>

-continued

SEQUENCE LISTING

<221> misc_feature

<222> (25)..(30)

<223> nnnnnn is a reverse complement DNA sequence of a TRUSEQ-ILLUM1NA-INDEX sequence

<400> 10
caagcagaag acggcatacg agatnnnnnn gtgactggag ttcagacgtg tgctcttccg 60
atct 64

<210> 11

<211> 59

<212> DNA

<213> Artificial Sequence

<220>

<223> Linker_TruSeq_T+ primer

<400> 11
gtaatacgac tcactatagg gctccgctta agggactcag acgtgtgctc ttccgatct 59

<210> 12

<211> 17

<212> DNA

<213> Artificial Sequence

<220>

<223> Linker_TruSeq_T- primer

<220>

<221> misc_feature

<222> (17)..(17)

<223> n is g-AMINO

<400> 12
gatcggaaga gcacacn 17

<210> 13

<211> 64

<212> DNA

<213> Artificial Sequence

<220>

<223> PE_NEST_IND6 primer

<400> 13
caagcagaag acggcatacg agatattggc gtgactggag ttcagacgtg tgctcttccg 60
atct 64

<210> 14

<211> 64

<212> DNA

-continued

SEQUENCE LISTING

<213> Artificial Sequence

<220>

<223> PE_NEST_IND7 primer

<400> 14
caagcagaag acggcatacg agatagtctg gtgactggag ttcagacgtg tgctcttccg 60
atct 64

<210> 15

<211> 64

<212> DNA

<213> Artificial Sequence

<220>

<223> PE_NEST_IND8 primer

<400> 15
caagcagaag acggcatacg agattcaagt gtgactggag ttcagacgtg tgctcttccg 60
atct 64

<210> 16

<211> 20

<212> DNA

<213> Artificial Sequence

<220>

<223> CAR-Fwd primer

<400> 16
atctggatgt cggggatcag 20

<210> 17

<211> 20

<212> DNA

<213> Artificial Sequence

<220>

<223> CAR-probe oligonucleotide

<220>

<221> miscjeature

<222> (1)..(1)

<223> n is FAM-A

<220>

<221> misc_feature

<222> (20)..(20)

<223> n is T-BH1

<400> 17
ngcagcatgg tggcggcgcn 20

-continued

SEQUENCE LISTING

<210> 18
<211> 20
<212> DNA
<213> Artificial Sequence
<220>
<223> CAR-Rev primer
<400> 18
gcttgctcaa ctctacgtct 20

<210> 19
<211> 18
<212> DNA
<213> Artificial Sequence
<220>
<223> MC-Fwd primer
<400> 19
ccgaccttaa tgcgcctc 18

<210> 20
<211> 27
<212> DNA
<213> Artificial Sequence
<220>
<223> MC-probe oligonucleotide
<220>
<221> misc_feature
<222> (1)..(1)
<223> n is FAM-G
<220>
<221> misc_feature
<222> (27)..(27)
<223> n is T-BH1
<400> 20
ncgctgtagc ctcacgccca catatgn 27

<210> 21
<211> 25
<212> DNA
<213> Artificial Sequence
<220>
<223> MC-Rev primer

-continued

SEQUENCE LISTING

<400> 21
aggattaaat gtcaggaatt gtgaa 25

<210> 22

<211> 20

<212> DNA

<213> Artificial Sequence

<220>

<223> RPP30-Fwd primer

<400> 22
ggttaactac agctcccagc 20

<210> 23

<211> 24

<212> DNA

<213> Artificial Sequence

<220>

<223> RPP30-probe oligonucleotide

<220>

<221> misc_feature

<222> (1)..(1)

<223> n is HEX-T

<220>

<221> misc_feature

<222> (24)..(24)

<223> n is C-BH1

<400> 23
nggacctgcg agcgggttct gacn 24

<210> 24

<211> 18

<212> DNA

<213> Artificial Sequence

<220>

<223> RPP30-Rev primer

<400> 24
ctgtctccac aagtccgc 18

SEQUENCE LISTING

<160> NUMBER OF SEQ ID NOS: 24

<210> SEQ ID NO 1

```
<211> LENGTH: 36
<212> TYPE: DNA
<213> ORGANISM: Artificial Sequence
<220> FEATURE:
<223> OTHER INFORMATION: L(+) primer

<400> SEQUENCE: 1

gtaatacgac tcactatagg gctccgctta agggac                                36


<210> SEQ ID NO 2
<211> LENGTH: 17
<212> TYPE: DNA
<213> ORGANISM: Artificial Sequence
<220> FEATURE:
<223> OTHER INFORMATION: L(-)FspBI primer
<220> FEATURE:
<221> NAME/KEY: misc_feature
<222> LOCATION: (17)..(17)
<223> OTHER INFORMATION: n is guanine modified with an AMINO group.

<400> SEQUENCE: 2

tagtccctta agcggan                                                     17


<210> SEQ ID NO 3
<211> LENGTH: 19
<212> TYPE: DNA
<213> ORGANISM: Artificial Sequence
<220> FEATURE:
<223> OTHER INFORMATION: Nested primer

<400> SEQUENCE: 3

agggctccgc ttaagggac                                                   19


<210> SEQ ID NO 4
<211> LENGTH: 22
<212> TYPE: DNA
<213> ORGANISM: Artificial Sequence
<220> FEATURE:
<223> OTHER INFORMATION: Linker primer

<400> SEQUENCE: 4

gtaatacgac tcactatagg gc                                               22


<210> SEQ ID NO 5
<211> LENGTH: 27
<212> TYPE: DNA
<213> ORGANISM: Artificial Sequence
<220> FEATURE:
<223> OTHER INFORMATION: T_Bal rev primer

<400> SEQUENCE: 5

gaattgtgat acagtgaatt ataagtg                                          27


<210> SEQ ID NO 6
<211> LENGTH: 27
<212> TYPE: DNA
<213> ORGANISM: Artificial Sequence
<220> FEATURE:
<223> OTHER INFORMATION: T_Bal primer

<400> SEQUENCE: 6

cttgtgtcat gcacaaagta gatgtcc                                          27


<210> SEQ ID NO 7
<211> LENGTH: 36
<212> TYPE: DNA
<213> ORGANISM: Artificial Sequence
```

```
<220> FEATURE:
<223> OTHER INFORMATION: T_Bal_long primer

<400> SEQUENCE: 7

cttgtgtcat gcacaaagta gatgtcctaa ctgact                                36


<210> SEQ ID NO 8
<211> LENGTH: 25
<212> TYPE: DNA
<213> ORGANISM: Artificial Sequence
<220> FEATURE:
<223> OTHER INFORMATION: LAM_SB_50 primer

<400> SEQUENCE: 8

agttttaatg actccaactt aagtg                                            25


<210> SEQ ID NO 9
<211> LENGTH: 83
<212> TYPE: DNA
<213> ORGANISM: Artificial Sequence
<220> FEATURE:
<223> OTHER INFORMATION: SB20h-bc-ill-N primer
<220> FEATURE:
<221> NAME/KEY: misc_feature
<222> LOCATION: (58)..(59)
<223> OTHER INFORMATION: A TRUSEQ-ILLUMINA-INDEX barcode DNA sequence is
      inserted between the nucleotides at positions 58 and 59.

<400> SEQUENCE: 9

aatgatacgg cgaccaccga gatctacact ctttccctac acgacgctct tccgatctct     60

taagtgtatg taaacttccg act                                              83


<210> SEQ ID NO 10
<211> LENGTH: 58
<212> TYPE: DNA
<213> ORGANISM: Artificial Sequence
<220> FEATURE:
<223> OTHER INFORMATION: PE-nest-ind1-N primer
<220> FEATURE:
<221> NAME/KEY: misc_feature
<222> LOCATION: (24)..(25)
<223> OTHER INFORMATION: A reverse complement DNA sequence of a TRUSEQ-
      ILLUMINA-INDEX sequence is inserted between the nucleotides at
      positions 24 and 25.

<400> SEQUENCE: 10

caagcagaag acggcatacg agatgtgact ggagttcaga cgtgtgctct tccgatct       58


<210> SEQ ID NO 11
<211> LENGTH: 59
<212> TYPE: DNA
<213> ORGANISM: Artificial Sequence
<220> FEATURE:
<223> OTHER INFORMATION: Linker_TruSeq_T+ primer

<400> SEQUENCE: 11

gtaatacgac tcactatagg gctccgctta agggactcag acgtgtgctc ttccgatct      59


<210> SEQ ID NO 12
<211> LENGTH: 17
<212> TYPE: DNA
<213> ORGANISM: Artificial Sequence
<220> FEATURE:
<223> OTHER INFORMATION: Linker_TruSeq_T- primer
<220> FEATURE:
<221> NAME/KEY: misc_feature
<222> LOCATION: (17)..(17)
<223> OTHER INFORMATION: n is guanine modified with an AMINO group.
```

<400> SEQUENCE: 12
gatcggaaga gcacacn 17

<210> SEQ ID NO 13
<211> LENGTH: 64
<212> TYPE: DNA
<213> ORGANISM: Artificial Sequence
<220> FEATURE:
<223> OTHER INFORMATION: PE_NEST_IND6 primer

<400> SEQUENCE: 13
caagcagaag acggcatacg agatattggc gtgactggag ttcagacgtg tgctcttccg 60
atct 64

<210> SEQ ID NO 14
<211> LENGTH: 64
<212> TYPE: DNA
<213> ORGANISM: Artificial Sequence
<220> FEATURE:
<223> OTHER INFORMATION: PE_NEST_IND7 primer

<400> SEQUENCE: 14
caagcagaag acggcatacg agatagtctg gtgactggag ttcagacgtg tgctcttccg 60
atct 64

<210> SEQ ID NO 15
<211> LENGTH: 64
<212> TYPE: DNA
<213> ORGANISM: Artificial Sequence
<220> FEATURE:
<223> OTHER INFORMATION: PE_NEST_IND8 primer

<400> SEQUENCE: 15
caagcagaag acggcatacg agattcaagt gtgactggag ttcagacgtg tgctcttccg 60
atct 64

<210> SEQ ID NO 16
<211> LENGTH: 20
<212> TYPE: DNA
<213> ORGANISM: Artificial Sequence
<220> FEATURE:
<223> OTHER INFORMATION: CAR-Fwd primer

<400> SEQUENCE: 16
atctggatgt cggggatcag 20

<210> SEQ ID NO 17
<211> LENGTH: 20
<212> TYPE: DNA
<213> ORGANISM: Artificial Sequence
<220> FEATURE:
<223> OTHER INFORMATION: CAR-probe oligonucleotide
<220> FEATURE:
<221> NAME/KEY: misc_feature
<222> LOCATION: (1)..(1)
<223> OTHER INFORMATION: n is adenine modified with a FAM group.
<220> FEATURE:
<221> NAME/KEY: misc_feature
<222> LOCATION: (20)..(20)
<223> OTHER INFORMATION: n is thymine modified with a BH1 group.

<400> SEQUENCE: 17
ngcagcatgg tggcggcgcn 20

```
<210> SEQ ID NO 18
<211> LENGTH: 20
<212> TYPE: DNA
<213> ORGANISM: Artificial Sequence
<220> FEATURE:
<223> OTHER INFORMATION: CAR-Rev primer

<400> SEQUENCE: 18

gcttgctcaa ctctacgtct                                                 20


<210> SEQ ID NO 19
<211> LENGTH: 18
<212> TYPE: DNA
<213> ORGANISM: Artificial Sequence
<220> FEATURE:
<223> OTHER INFORMATION: MC-Fwd primer

<400> SEQUENCE: 19

ccgaccttaa tgcgcctc                                                   18


<210> SEQ ID NO 20
<211> LENGTH: 27
<212> TYPE: DNA
<213> ORGANISM: Artificial Sequence
<220> FEATURE:
<223> OTHER INFORMATION: MC-probe oligonucleotide
<220> FEATURE:
<221> NAME/KEY: misc_feature
<222> LOCATION: (1)..(1)
<223> OTHER INFORMATION: n is guanine modified with a FAM group.
<220> FEATURE:
<221> NAME/KEY: misc_feature
<222> LOCATION: (27)..(27)
<223> OTHER INFORMATION: n is thymine modified with a BH1 group.

<400> SEQUENCE: 20

ncgctgtagc ctcacgccca catatgn                                         27


<210> SEQ ID NO 21
<211> LENGTH: 25
<212> TYPE: DNA
<213> ORGANISM: Artificial Sequence
<220> FEATURE:
<223> OTHER INFORMATION: MC-Rev primer

<400> SEQUENCE: 21

aggattaaat gtcaggaatt gtgaa                                           25


<210> SEQ ID NO 22
<211> LENGTH: 20
<212> TYPE: DNA
<213> ORGANISM: Artificial Sequence
<220> FEATURE:
<223> OTHER INFORMATION: RPP30-Fwd primer

<400> SEQUENCE: 22

ggttaactac agctcccagc                                                 20


<210> SEQ ID NO 23
<211> LENGTH: 24
<212> TYPE: DNA
<213> ORGANISM: Artificial Sequence
<220> FEATURE:
<223> OTHER INFORMATION: RPP30-probe oligonucleotide
<220> FEATURE:
<221> NAME/KEY: misc_feature
<222> LOCATION: (1)..(1)
<223> OTHER INFORMATION: n is thymine modified with a HEX group.
```

-continued

```
<220> FEATURE:
<221> NAME/KEY: misc_feature
<222> LOCATION: (24)..(24)
<223> OTHER INFORMATION: n is cytosine modified with a BH1 group.

<400> SEQUENCE: 23

nggacctgcg agcgggttct gacn                                    24


<210> SEQ ID NO 24
<211> LENGTH: 18
<212> TYPE: DNA
<213> ORGANISM: Artificial Sequence
<220> FEATURE:
<223> OTHER INFORMATION: RPP30-Rev primer

<400> SEQUENCE: 24

ctgtctccac aagtccgc                                           18
```

The invention claimed is:

1. A non-viral method for administering a recombinant lymphocyte that expresses an engineered T-cell receptor or chimeric antigen receptor to a subject, the method comprising:

(a) introducing (i) a DNA minicircle comprising a transposable element and (ii) an in vitro transcribed RNA encoding a transposase into a human primary lymphocyte, wherein the DNA minicircle does not comprise a selectable marker;

wherein the transposable element comprises an expression cassette comprising a promoter and a coding sequence for the engineered T-cell receptor or the chimeric antigen receptor, wherein introduction of the DNA minicircle and in vitro transcribed RNA into the human primary lymphocyte results in transposition of the transposable element into the genome of the cell and expression of the engineered T-cell receptor or chimeric antigen receptor on the human primary lymphocyte; and wherein the in vitro transcribed RNA and the DNA minicircle are introduced into the human primary lymphocyte in a weight ratio of 4:1 to 8:1

(b) administering a therapeutically effective dose of the cells produced in step (a) as an adoptive immunotherapy to a human subject that has cancer, wherein steps (a) and (b) and any steps that are performed between steps (a) and steps (b) are done without selecting for recombinant lymphocytes that express the engineered T-cell receptor or chimeric antigen receptor.

2. The method according to claim 1, wherein the engineered T-cell receptor or chimeric antigen receptor is specific for CD19, CD20, CD22, CD33, CD44v6, CD123, CD135, EpCAM, EGFR, an EGFR variant, GD2, ROR1, ROR2, CD269, CD319, CD38, or CD138.

3. The method according to claim 1, wherein:

I) the coding sequence encodes an a/b or g/d T-cell receptor;

II the introducing is done by electroporation;

III) the transposase is Sleeping Beauty, PiggyBac, Frog Prince, Himarl, Passport, Minos, hAT, Tol1, Tol2, AciDs, PIF, Harbinger, Harbinger3-DR, and Hsmar1; and/or IV) the DNA minicircle encoding the transposable element and the in vitro transcribed RNA are introduced into the human primary lymphocyte together.

4. The method of claim 1, wherein the transposase encoded by the in vitro transcribed RNA is the 100X hyperactive Sleeping Beauty transposase (SB100X).

5. The method of claim 1, wherein the lymphocyte is a T lymphocyte or natural killer (NK) cell.

6. The method of claim 1, wherein the method comprises:

transfecting a population of human primary lymphocytes with the DNA minicircle and in vitro transcribed RNA;

incubating the transfected population of human primary lymphocytes so as to provide for expression of the engineered T-cell receptor or chimeric antigen receptor on some of the human primary lymphocytes; and after the incubating step, administering the human primary lymphocytes to a subject without selecting for cells that express the engineered T-cell receptor or chimeric antigen receptor.

7. The method of claim 1, wherein the introducing is done by electrotransfer or chemotransfer.

* * * * *